US007807789B2

(12) United States Patent
Guo et al.

(10) Patent No.: US 7,807,789 B2
(45) Date of Patent: Oct. 5, 2010

(54) REAGENTS FOR THE DETECTION OF PROTEIN PHOSPHORYLATION IN EGFR-SIGNALING PATHWAYS

(75) Inventors: Ailan Guo, Burlington, MA (US); Kimberly Lee, Seattle, WA (US); Klarisa Rikova, Reading, MA (US); Charles Farnsworth, Concord, MA (US); Albrecht Moritz, Salem, MA (US); Yu Li, Andover, MA (US); Robert Polakiewicz, Lexington, MA (US)

(73) Assignee: Cell Signaling Technology, Inc., Danvers, MA (US)

( * ) Notice: Subject to any disclaimer, the term of this patent is extended or adjusted under 35 U.S.C. 154(b) by 0 days.

(21) Appl. No.: 11/821,130

(22) Filed: Jun. 21, 2007

(65) Prior Publication Data
US 2008/0108795 A1 May 8, 2008

(51) Int. Cl.
C12P 21/08 (2006.01)
C07K 16/28 (2006.01)

(52) U.S. Cl. ............ 530/387.1; 530/388.1; 530/388.22; 530/389.1; 530/391.1; 530/391.3; 424/130.1; 424/141.1; 424/143.1; 424/178.1

(58) Field of Classification Search ........................ None
See application file for complete search history.

(56) References Cited

U.S. PATENT DOCUMENTS

| 3,940,475 | A | 2/1976 | Gross et al. |
|---|---|---|---|
| 4,289,747 | A | 9/1981 | Chu et al. |
| 4,349,893 | A | 9/1982 | Wiegman et al. |
| 4,376,110 | A | 3/1983 | David et al. |
| 4,474,893 | A | 10/1984 | Reading et al. |
| 4,634,664 | A | 1/1987 | Oestberg et al. |
| 4,634,666 | A | 1/1987 | Engleman et al. |
| 4,659,678 | A | 4/1987 | Forrest et al. |
| 4,676,980 | A | 6/1987 | Segal et al. |
| 4,727,022 | A | 2/1988 | Skold et al. |
| 4,816,397 | A | 3/1989 | Boss et al. |
| 4,816,567 | A | 3/1989 | Cabilly et al. |
| 4,946,778 | A | 8/1990 | Ladner et al. |
| 5,004,692 | A | 4/1991 | Tso et al. |
| 5,092,885 | A | 3/1992 | Yamada et al. |
| 5,112,946 | A | 5/1992 | Maione et al. |
| 5,192,744 | A | 3/1993 | Bouck et al. |
| 5,202,352 | A | 4/1993 | Okada et al. |
| 5,225,539 | A | 7/1993 | Winter |
| 5,260,203 | A | 11/1993 | Ladner et al. |
| 5,530,101 | A | 6/1996 | Queen et al. |
| 5,545,806 | A | 8/1996 | Lonberg et al. |
| 5,565,332 | A | 10/1996 | Hoogenboom et al. |
| 5,585,089 | A | 12/1996 | Queen et al. |
| 5,675,063 | A | 10/1997 | Knight et al. |
| 5,677,427 | A | 10/1997 | Goldenberg et al. |
| 5,693,761 | A | 12/1997 | Queen et al. |
| 5,693,762 | A | 12/1997 | Queen et al. |
| 5,789,208 | A | 8/1998 | Sharon |
| 5,969,108 | A | 10/1999 | McCafferty et al. |
| 6,103,889 | A | 8/2000 | Whitlow et al. |
| 6,120,767 | A | 9/2000 | Reagan et al. |
| 6,150,584 | A | 11/2000 | Kucherlapati et al. |
| 6,180,370 | B1 | 1/2001 | Queen et al. |
| 6,329,508 | B1 | 12/2001 | Friden et al. |
| 6,331,415 | B1 | 12/2001 | Cabilly et al. |
| 6,335,163 | B1 | 1/2002 | Sharon et al. |
| 6,355,245 | B1 | 3/2002 | Evans et al. |
| 6,395,718 | B1 | 5/2002 | Slusher et al. |
| 6,407,213 | B1 | 6/2002 | Carter et al. |
| 6,441,140 | B1 | 8/2002 | Comb et al. |
| 6,462,075 | B1 | 10/2002 | Bowen et al. |
| 6,465,431 | B1 | 10/2002 | Thorn et al. |
| 6,475,784 | B1 | 11/2002 | Papkoff |
| 6,482,802 | B1 | 11/2002 | Hu et al. |
| 6,482,810 | B1 | 11/2002 | Brem et al. |
| 6,500,431 | B1 | 12/2002 | Gill et al. |
| 6,500,924 | B1 | 12/2002 | Brooks et al. |
| 6,518,198 | B1 | 2/2003 | Klein |
| 6,521,439 | B2 | 2/2003 | Folkman et al. |
| 6,525,019 | B2 | 2/2003 | D'Amato et al. |

(Continued)

FOREIGN PATENT DOCUMENTS

EP 0120694 3/1984

(Continued)

OTHER PUBLICATIONS

Heisermann et al, J Biol Chem 263(26): 13152-13158, 1988.*
Transduction Laboratories, 1999 cell Biology Sourcebook, pp. 242-245.*
Harlow et al, in Antibodies a Laboratory Manual, 1988, Cold Spring harbor laboratory publication, Cold Spring Harbor, NY, pp. 340-353, and 409-410.*
U.S. Appl. No. 10/408,486, filed Jul. 4, 2003, Crosby et al.
U.S. Appl. No. 10/781,047, filed Feb. 17, 2004, Gygi et al.

(Continued)

Primary Examiner—Phuong Huynh
(74) Attorney, Agent, or Firm—Nancy Chiu Wilker

(57) ABSTRACT

The invention discloses 168 novel phosphorylation sites identified in signal transduction proteins and pathways downstream of, and including, EGFR kinase, and provides phosphorylation-site specific antibodies and heavy-isotope labeled peptides (AQUA peptides) for the selective detection and quantification of these phosphorylated sites/proteins, as well as methods of using the reagents for such purpose. Among the phosphorylation sites identified are sites occurring in the following protein types: Actin Binding proteins, Adaptor/Scaffold proteins, Calcium-Binding Proteins, Cell Cycle Regulation proteins, Cytoskeletal proteins, DNA Binding and Replication Proteins, GTPase Activating proteins, Guanine Nucleotide Exchange Factor proteins, Lipid Kinases, Receptor Tyrosine Kinases, Receptor Tyrosine Kinase ligands, Protein Kinases, Receptor and Protein Phosphatases, Transcription Factor proteins, Tumor Suppressor proteins, and Vesicle proteins.

6 Claims, 8 Drawing Sheets

U.S. PATENT DOCUMENTS

| | | | |
|---|---|---|---|
| 6,538,103 | B1 | 3/2003 | Ji et al. |
| 6,544,758 | B2 | 4/2003 | O'Reilly et al. |
| 6,544,947 | B2 | 4/2003 | Holaday et al. |
| 6,548,477 | B1 | 4/2003 | Olson et al. |
| 6,548,640 | B1 | 4/2003 | Winter et al. |
| 6,559,126 | B2 | 5/2003 | Tournaire et al. |
| 6,569,845 | B1 | 5/2003 | Futamura et al. |
| 6,573,256 | B2 | 6/2003 | Bishop et al. |
| 6,783,961 | B1 | 8/2004 | Edwards et al. |
| 6,867,007 | B2 | 3/2005 | Kauvar et al. |
| 6,884,869 | B2 | 4/2005 | Senter et al. |
| 6,979,557 | B2 | 12/2005 | Isogai et al. |
| 7,060,268 | B2 | 6/2006 | Andya et al. |
| 7,109,000 | B2 | 9/2006 | Edinger et al. |
| 7,198,896 | B2 | 4/2007 | Rush et al. |
| 7,300,753 | B2 | 11/2007 | Rush et al. |

FOREIGN PATENT DOCUMENTS

| | | |
|---|---|---|
| EP | 1184665 | 9/1986 |
| EP | 0239400 | 9/1987 |
| EP | 0404097 | 12/1990 |
| WO | WO 84/03508 | 9/1984 |
| WO | WO 85/03508 | 8/1985 |
| WO | WO 86/01533 | 3/1986 |
| WO | WO 91/10741 | 7/1991 |
| WO | WO 91/17271 | 11/1991 |
| WO | WO 92/01047 | 1/1992 |
| WO | WO 93/11161 | 6/1993 |
| WO | WO 93/12227 | 6/1993 |
| WO | WO 95/20401 | 8/1995 |
| WO | WO 96/27011 | 6/1996 |
| WO | WO 02/00729 | 3/2002 |
| WO | WO 02/27017 A2 * | 4/2002 |
| WO | WO 03/016861 | 2/2003 |
| WO | WO 03/087831 A2 * | 10/2003 |
| WO | WO 03/089474 | 10/2003 |
| WO | WO 03/106644 | 12/2003 |
| WO | WO 2004/009618 | 1/2004 |
| WO | WO 2004/039963 | 5/2004 |
| WO | WO 2004/066957 | 8/2004 |
| WO | WO 2004/091658 | 10/2004 |
| WO | WO 2005/056825 | 6/2005 |
| WO | WO 2005/083444 | 9/2005 |

OTHER PUBLICATIONS

U.S. Appl. No. 10/634,581, filed May 8, 2003, Johnson et al.
U.S. Appl. No. 10/821,234, filed Jul. 4, 2004, Labat et al.
U.S. Appl. No. 11/077,717, filed Oct. 3, 2005, Lam et al.
U.S. Appl. No. 11/089,368, filed Mar. 25, 2005, Ledbetter et al.
U.S. Appl. No. 11/049,630, filed Feb. 2, 2005, McKinsey et al.
Abu-Duhier et al., "Identification of novel FLT-3 Asp835 mutations in adult acute myeloid leukemia." Br. J. Haematol. 113: 983-988 (2001).
Hardy, et al., "Clinical and Molecular Genetic Analysis of 19 Wolfram Syndrome Kindreds Demonstrating a Wide Spectrum of Mutations in WFS1", Am. J. Hum. Genet. 65:1279-1290 (1999).
Dessein, et al., "Severe Hepatic Fibrosis in Schistoma mansoni Infection Is Controlled by a Major Locus That Is Closely Linked to the Interferon-γ Receptor Gene", Am. J. Hum. Genet. 65:709-721, (1999).
Grand, et al., "p53-Binding Protein 1 Is Fused to the Platelet-Derived Growth Factor Receptor B in a Patient with a t(5;15)(q33;q22) and a Imagine-Responsive Eosinophilic Myeloproliferative Disorder", Cancer Research 64, 7216-7219, Oct. 15, 2004.
Carr, et al., "The Need for Guidelines in Publication of Peptide and Protein Identification Data", Molecular & Cellular Proteomics 3.6, 531-533, 2004.
Cell Signaling Technology, "Phospho-PLCgammal (Tyr783) Antibody" 2007 Cell Signaling Technology, Inc., Jul. 2000, 1-3.

Accili et al., "FoxOs at the Crossroads of Cellular Metabolism, Differentiation, and Transformation" Cell, vol. 117, 421-426, May 14, 2004, Copyright 2004 by Cell Press.
Chow et al., "Measurement of MAP Kinase Activation by Flow Cytometry Using Phospho-Specific Antibodies to MEK and ERK: Potential for Pharmacodynamic Monitoring of Signal Transduction Inhibitors", Cytometry (Communications in Clinical Cytometry) 46: 72-78 (2001).
Coia, et al., "Panning and selection of proteins using ribosome display", Journal of Immunological Methods 254 (2001) 191-197.
Crook, et al.,"Repressed by a NuRD", Nature Cel Biology vol. 8 No. 3 Mar. 2006, 212-214.
Cross, et al.,"Serine/Threonine Protein Kinases and Apoptosis", Experimental Cell Research 256, 34-41, 2000.
Czernik, et al.,"Production of Phosphorylation State-Specific Antibodies", Methods in Enzymology, vol. 201, 1991, 264-283.
Daley, et al, "Induction of Chronic Myelogenous Leukemia in Mice by the P210bcr/abl Gene of the Philadelphia Chromosome" Science, vol. 247, 1990, 824-830.
Denslow, et al., "The human Mi-2/NuRD complex and gene regulation", Oncogene (2007) 26, 5433-5438.
Dorahy, et al., "Capture by chemical crosslinkers provides evidence that integrin allbfl3 forms complex with protein tyrosine kinases in intact platelets" Biochem J. (1995) 389, 481-490 (Printed in Great Britain).
Druker, et al., "Imatinib as a Paradigm of Targeted Therapies", Adv. Cancer Res. 2004, 91 (): 1-30.
Edgar, et al., "Flotillin-1: gene structure c DNA cloning from human lung and the identification of alternative polyadenylation signals", The international Journal of Biochemisty & Cell Biology 33 (2001) 53-64.
Blanton, et al., "Schistosomal hepatic fibrosis and the interferon gamma receptor: a linkage analysis using single-nucleotide polymorphic markers", European Journal of Human Genetics (2005) 13, 660-668.
Song, et at., "Lamin A/C mutations associated with familial and sporadic cases of dilated cardiomyopathy in Koreans", Experimental and Molecular Medicine, vol. 39, No. 1, 114-120, Feb. 2007.
Fanger, et al., "Bispecific antibodies and targeted cellular cytotoxicity", Immunol Today, Feb. 1991;12(2):51-4.
Vadlamudi, et al., "Heregulin and HER2 signaling selectively activates c-Src phosphorylation at tyrosine 215" FEBS Letters 543 (2003) 76-80.
Yang, et al "ERK promotes tumorigenesis by inhibiting FOXO3a via MDM2-mediated degradation." Nat Cell Biol. Feb. 2008;10(2):138-48.
Fujita N. et al., "MTA3 and the Mi-2/NuRD complex regulate cell fate during B lymphocyte differentiation." (2004)Cell 119:75-86.
Fujita N. et al., "MTA3; a Mi-2/NuRD Complex Subunit, Regulates an Invasive Growth Pathway in Breast Cancer." (2003) Cell 113:207-19.
Meinhart, et al "A Structural Perspective of CTD Function." Genes Dev. Jun. 15, 2005, 19 (12) :1401-15.
Di Barletta, et al., "Different Mutations in the LMNA Gene Cause Autosomal Dominant and Autosomal Recessive Emery-Dreifuss Muscular Dystrophy", Am. J. Hum. Genet. 66:1407-1412 (2000).
Ebrahimi, et al., "Murine Gammaherpesvirus-68 Infection Causes Multi-Organ Fibrosis and Alters Leukocyte Trafficking in Interferon-γ Receptor Knockout Mice", American Journal of Pathology, vol. 158, No. 6 Jun. 2001.
Jemal, et al., "Cancer Statistics 2005", CA: A Cancer Journal for Clinicians, Aug. 26, 2008.
Pollard, et al., "Using Single-Gene Deletions to Identify Checkpoints in the Progression of Systemic Autoimmunity", Annals of the New York Academy of Sciences, Apr. 2003; 987(): 236-9.
Jaskiewicz, et al., "Expression of p53 Tumor Suppressor Gene, Oncoprotein c-erbB-2, Cellular Proliferation and Differentiation n Malignant and Benign Pancreatic Lesions", Anticancer Research 14: 1919-1922 (1994).
Agarwal, et al., "Inositol Hexaphosphate Inhibits Constitutive Activation of NF-xB in Androgen-independent Human Prostate Carcinoma DU145 Cells", Anticancer Research 23: 3855-3862 (2003).

Arias-Romero, et al., "A tale of two Paks", Biol. Cell (2008) 100, 97-108.

Bache, et al., "Phosphorylation of Hrs downstream of the epidermal growth factor receptor", Eur. J. Biochem 269, 3881-3881 (2002).

Belsches, et al., "Role of c-Src Tyrosine Kinase in EEGF-Induced Mitogenesis." Frontiers in Bioscience 2,d501-518, Oct. 15, 1997.

G-Amlak, et al., "Reguation of myeloma cell growth through Akt/Gsk3/forkhead signaling pathway", Biochemical and Biophysical Research Sommunications 297 (2002) 760-764.

Radaeva, et al., "Interferon-γ inhibits interferon-α signalling in hepatic cells: evidence for the involvement of STAT1 induction and hyperexpression of STAT1 in chronic hepatitis C", Biochem J. (2004) 379, 199-208.

Awasthi, et al., "Novel Function of Human RLIP76: ATP-Dependent Transport of Glutathione Conjugates and Doxorubicin", Biochemistry, 39: 9327-9334, 2000.

Jagani, et al., "Foxe tumor suppressors and BCR-ABL-induced leukemia: A matter of evasion of apoptosis", Biochimica et Biophysica Acta 1785 (2008) 63-84.

Hashimoto, et al., "The Breakpoint Cluster Region Gene on Chromosome 22q11 Is Associated with Bipolar Disorder", Biol Psychiatry, May 15, 2005;57(10):1097-102.

Bird, et al., "Single-Chain Antigen-Binding Proteins", Science, vol. 242: 423-426, Oct. 21, 1988.

Blood, et al., "Tumor interactions with the vasculature: angiogenesis and tumor metastasis." Biochemica et Biophysica Acta, 1032 (1990) 89-118.

Awasthi, et al., "RLIP76, a non-ABC transporter, and drug resistance in epilepsy", BMC Neuroscience, 6: 61, 2005.

Boder, et al., "Yeast surface display for screening combinatorial polypeptide libraries", Nature Biotechnology, vol. 15, 553-557, Jun. 1997.

Bordin, et al., "Band 3 is an anchor protein and a target for SHP-2 tyrosine phosphatase in human erythrocytes", Blood, vol. 100, No. 1, 276-282, Jul. 1, 2002.

Brand, et al., "Fluorescence Probes for Structure1", Annu.Rev. Biochem. 1972.41:843-868.

Brennan, et al., "Preparation of Bispecific Antibodies by Chemical Recombination of Monoclonal Immunoglobulin G1 Fragments", Science, vol. 229:81-83, Jul. 5, 1985.

Byers et al., "Rationale for clinical use of immunotoxins in cancer and autoimmune disease" Seminars in Cell Biology 2:59-70 (1991).

Calalb, et al.,"Tyrosine Phosphorylation of Focal Adhesion Kinase at Sites in the Catalytic Domain Regulates Kinase Activity: a Role for Src Family Kinases", Molecular and Cellular Biology, vol. 15, No. 2 Feb. 1995, p. 954-963.

Gerber et al., "Absolute quantification of proteins and phosphoproteins from cell lysates by tandem MS." Cell 113:207-19.

Graves et al. "protein phosphorylation and signal transduction." Pharmacol. Ther. 82: 111-21 (1999).

Griffiths et al. "Human anti-self antibodies with high specificity from phage display libraries." EMBO L., 12:725-734 (1993).

Griffiths et al. "Isolation of high affinity human antibodies directly from large synthetic repertoires." EMBO J. 13:3245-3260 (1994).

Gruber et al. "Efficient tumor cell lysis mediated by a bispecific single chain antibody expressed in Escherichia coli." J. Immunol., 152:5368 (1994).

Gu et al. "Phosphotyrosine profiling identifies the KG-1 cell line as a model for the study of FGFR1 fusions in acute myeloid leukemia." Blood First Edition Paper and supplemental table 1, pre-published online Aug. 31, 2006; DOI 10.1182/blood-2006-06-026666, see p. 3 of Table 1, litening under "Hsp70".

Hanes J. et al. "Picomolar affinity antibodies from a fully synthetic naive library selected and evolved by ribosome display." Nat. Biotechnol. 18(12):1287-92(2000).

Heessen S., Fornerod M., "The inner nuclear envelope as a transcription factor resting place." EMBO Rep. 8:914-9 (2007).

Kakumu, et al "Interferon-gamma receptors on T cells in patients with chronic liver disease." Hepatogastroenterology Aug;35(4):158-61(1988).

Hollinger et al., "Diabodies: small bivalent and bispecific antibody fragments." Proc. Natl. Acaf. Sci. USA, 90:6444-8(1993).

Burwinkel et al "Phosphorylase-kinase-deficient liver glycogenosis with an unusual biochemical phenotype in blood cells associated with a missense mutation in the beta subunit gene (PHKB)." Hum Genet Dec;101(2):170-4 (1997).

Blume-Jensen et al., "Oncogenic kinase signalling." Nature 411: 355-65 (2001).

Huse w. "Generation of a Large Combinatorial Library of the Immunoglobulin Repertoire in Phage Lambda." Science 246:1275-1281 (1989).

Ingber et al., "Inhibition of Angiogenesis Through Modulation of Collagen Metabolism." Lab. Invest., 59:44-51 (1988).

Htun Van Der Horst, et al "Tyrosine phosphorylation of PYK2 mediates heregulin-induced glioma invasion: novel heregulin/HER3-stimulated signaling pathway in glioma." Int. J Cancer Feb. 20;113(5):689-98 (2005).

Irby et al., "Role of Src expression and activation in human cancer." Oncogene 16: 5636-642 (2000).

Jullien-Flores "Bridging Ral GTPase to Rho pathways" RLIP76, a Ral effector with CDC42/Rac GTPase-activating protein activity. J Cell Chem Sep. 22, 1995;270(38):22473-7.

Hu, et al "HSF-1 interacts with Ral-binding protein 1 in a stress-responsive, multiprotein complex with HSP90 in vivo" J Cell Chem. May 9, 2003;278(19):17299-306.

Birkenkamp, et al "FOXO3a induces differentiation of Bcr-Abl-transformed cells through transcriptional down-regulation of Id1." J Biol. Chem. Jan. 26, 2007;282(4):2211-20.

Goldfinger, et al "RLIP76 (RalBP1) is an R-Ras effector that mediates adhesion-dependent Rac activation and cell migration." J Cell Biol. Sep. 11, 2006;174(6):877-88.

Dorman, et al "Viral infections in interferon-gamma receptor deficiency." The Journal of Pediatrics Nov;135(5):640-3(2006).

Kim H. et al., "Epidermal growth factor-dependent association of phosphatidylinositol 3-kinase with the erbB3 gene product" J Biol. Chem., 269(40)24747-24755(1994).

Kohler, et al "Derivation of specific antibody-producing tissue culture and tumor lines by cell fusion." Eur. J. Immunol. 6:511 (1976).

Kostelny et al., "Formation of a Bispecific Antibody by the Use of Leucine Zippers." J. Immunol., 148(5):1547-1557 (1992).

Dorman, et al "Clinical features of dominant and recessive interferon gamma receptor 1 deficiencies." Lancet Dec. 11-17, 2004;364(9451):2113-21.

Merrifield "Solid Phase Peptide Synthesis I, The Synthesis of a Tetrapeptide." J. Am. Chem. Soc. 85:21-49 (1962).

Milstein and Cuello "Hybrid hybridomas and their use in immunohistochemistry." Nature, 305:537-540(1983).

Radziwill, et al "The Bcr kinase downregulates Ras signaling by phosphorylating AF-6 and binding to its PDZ domain." Mol. Cell Biol. Jul. 2003;23(13):4663-42.

Morrison et al., "Chimeric human antibody molecules: Mouse antigen-binding domains with human constant region domains." Proc. Nat'l Acad. Sci. 81: 6851(1984).

Moses et al., "Identification of an Inhibitor of Neovascularization from cartilage." Science, 248:1408-1410 (1990).

Mullinax et al., "Identification of human antibody fragment clones specific for tetanus toxoid in a bacteriophage gamma immunoexpression library." Proc. Nat'l Acad. Sci. 87: 8095(1990).

Nakamura, Y., "Codon usage tabulated from international DNA sequence databases: status for the year 2000." Nucleic Acids Res. Jan. 1;28:292 (2000).

Nardi, et al., "Mechanisms and implications of imatinib resistance mutations in BCR-ABL." Curr. Opin. Hematol. 11:35-43(2003).

Shackleton, et al "LMNA, encoding lamin A/C, is mutated in partial lipodystrophy." Nat. Genet. Feb. 2000;24(2):153-6.

Shankaran, et al "IFN gamma and lymphocytes prevent primary tumour development and shape tumour immunogenicity." Nature Apr. 26, 2001; 410(6832): 1107-11.

Feske, et al "A mutation in Orai1 causes immune deficiency by abrogating CRAC channel function." Nature May 11, 2006;441 (7090):179-85.

Neuberger, et al "Recombinant antibodies possessing novel effector functions." Nature. Dec. 13-19, 1984; 312(5995):604-8.

Newman et al., "Primatization of Recombinant Antibodies for Immunotherapy of human Diseases: A Macaque/Human Chimeric Antibody Against Human CD4." BioTechnology, 10: 1455-1460(1992).

Nissim et al., "Antibody fragments from a 'single pot' phage display library as immunochemical reagents." EMBO J. Feb. 1, 1994;13(3):692-8.

Ostberg, et al.,"Human × (Mouse × Human) Hybridomas Stably Producing Human Antibodies", Hybridoma, vol. 2, No. 4, 1983, 361-367.

Olayioye, et al.,"The ErbB signaling network: receptor heterodimerization in development and cancer", The EMBO Journal vol. 19 No. 13 pp. 3159-3167, 2000.

Liu, et al., "Induction of prosurvival molecules by apoptotic stimuli: involvement of FOX03a and ROS", Oncogene (2005) 24, 2020-2031.

Order, et al., "Analysis, Results, and Future Prospective of the Therapeutic Use of Radiolabeled Antibody in Cancer Therapy", Monoclonal Antibodies for Cancer Detection and Therapy, Baldwin et al. (eds.), pp. 303-316 (Academic Press 1985).

Paweletz, et al., "Reverse phase protein microarrays which capture disease progression show activation of pro-survival pathways at the cancer invasion front", Oncogene (2001) 20, 1981-1989.

Pluckthun et al., "Antibodies from *Escherichia coli*" The Pharmacology of Monoclonal Antibodies, vol. 113, Rosenburg and Moore, eds. (Springer-Verlag: New York, 1994), pp. 269-315.

Prigent, et al., "Identification of c-erbB-3 binding sites for phosphatidylinositol 3'-kinase and SHC using an EGF receptor/c-erbB-3 chimera" The EMBO Journal vol. 13 No. 12 pp. 2831-2841, 1994.

Yamamoto, et al., "Activating mutation of D835 within the activation loop of FLT3 in human hematologic malignancies" Blood, Apr. 15, 2001 vol. 97, No. 8 2434-2439.

Yang, et al., "Lysine acetylation and the bromodomian: a new partnership for signaling", BioEssays, 2004, vol. 26, Iss 10, 1076-1087.

Yeatman, et at, "A Renaissance for SRC", Nature Reviews 4: 2004, 470-480.

Yeung, et al., "Quantitative Screening of Yeast Surface-Displayed Polypeptide Libraries by Magnetic Bead Capture" Biotechnol. Prog. 2002, 18(2):212-20.

Yokota, et al., "Internal tandem duplication of the FLT3 gene is preferentially seen in acute myeloid leukemia and myelodysplastic syndrome among various hematological malignancies. A study on a large series of patients and cell lines", Leukemia 1997 11: 1605-1609.

Zapata, et al., "Engineering linear F (ab')2 fragments for efficient production in *Escherichia coli* and enhanced antiproliferative activity" Protein Engineering vol. 8 No. 10 pp. 1057-1062, 1995.

Zhang, et al., "Phosphoprotein Analysis Using Antibodies Broadly Reactive against Phosphorylated Motifs" Journal of Biological Chemistry, 2002, vol. 227, pp. 39379-39387.

Binns, et al, "Phosphorylation of Tyrosine Residues in the Kinase Domain and Juxtamembrane Region Regulates the Biological and Catalytic Activities of Eph Receptors" Molecular and Cellular Biology 20 (13): 4791-4805 (2000).

Ellis, et al, "A juxtamembrane autophosphorylation site in the Eph family receptor tyrosine kinase, Sek, mediates high affinity interaction with p59fyn" Oncogene 12: 1727-1736 (1996).

Li, et al, "Phosphorylation of Caveolin by Src Tyrosine Kinases" The Journal of Biological Chemistry 271 (7): 3863-3868 (1996).

Done, et al, "Tyrosine 537 within the Na+,K+-ATPase α-Subunit Is Essential for AP-2 Binding and Clathrin-dependent Endocytosis" The Journal of Biological Chemistry 277 (19): 17108-17111 (2002).

Zrihan-Licht, et al, "RAFTK/Pyk2 tyrosine kinase mediates the association of p190 RhoGAP with RasGap and is involved in breast cancer cell invasion" Oncogene 19: 1318-1328 (2000).

Chiarugi, et al "The Low *Mr* Protein-tyrosine Phosphatase Is Involved in Rho-mediated Cytoskeleton Rearrangement after Integrin and Platelet-derived Growth Factor Stimulation" The Journal of Biological Chemistry 275 (7): 4640-4646 (2000).

Chiarugi, et al, "Low Molecular Weight Protein-tyrosine Phosphatase Controls the Rate and the Strength of NIH-3T3 Cells Adhesion through Its Phosphorylation on Tyrosine 131 or 132" The Journal of Biological Chemistry 275 (48): 37619-37627 (2000).

Bucciantini, et al "The Low *Mr* phosphotyrosine protein phosphatase behaves differently when phosphorylated at Tyr131 or Tyr132 by Src kinase" FEBS Letters 456: 73-78 (1999).

Tailor, et al, "Regulation of the Low Molecular Weight Phosphotyrosine Phosphatase by Phosphorylation and Tyrosines 131 and 132" The Journal of Biological Chemistry 272 (9): 5371-5374 (1997).

Wang, et al, "Identification of four sites of stimulated tyrosine Phosphorylation in the MUC1 cytoplasmic tail" Biochemical and Biophysical Research Communications 310: 341-346 (2003).

Kinlough, et al "MUC1 Membrane of Trafficking is Modulated by Multiple Interactions" The Journal of Biological Chemistry 279 (51): 53071-53077 (2004).

Steen, et al "Tyrosine Phosphorylation Mapping of the Epidermal Growth Factor Receptor Signaling Pathway" The Journal of Biological Chemistry 277 (2): 1031-1039 (2002).

Cao, Kan "A lamin A protein isoform over expressed in Hutchinson-Gilford progeria syndrome interferes with mitosis in progeria and normal cells" Proc. Natl. Acad. Sci U S A. Mar. 20, 2007;104(12):4949-54.

Dechat, H. "Alterations in mitosis and cell cycle progression caused by a mutant lamin A known to accelerate human aging." Proc. Natl. Acad. Sci U S A. Mar. 20, 2007;104(12):4955-60.

Hanes, J. "In vitro selection and evolution of functional proteins by using ribosome display" Proc. Natl. Acad. Sci. U. S. A. 94(10):4937-42 (1997).

Hanes, J. "Ribosome display efficiently selects and evolves high-affinity antibodies in vitro from immune libraries." Proc. Natl. Acad. Sci. U. S. A. 95(24):14130-5 (1998).

Masui, et al., "A possible association between missense polymorphism of the breakpoint cluser region gene and lithium prophylaxis in bipolar disorder", Progress in Neuro-Psychopharmacogy & Biological Psychiatry 32 ( 2008) 204-208.

Rosnet, et al.,"Hematopoietic Receptors of Class III Receptor-type Tyrosine Kinases", Critical Reviews in Ontogenesis, 4 (6): 595-613 (1993).

Schaller, et al.,"Autophosphorylation of the Focal Adhesion Kinase, pp125FAK Directs SH2-Dependent Binding of pp60src", Molecular and Cellular Biology, Mar. 1994, p. 1680-1688.

Schindler, et al., "Structural Mechanism for STI-571 Inhibition of Abelson Tyrosine Kinase", Science 289: 1938-1942 (2000).

Schreiber, et al., "Target-Oriented and Diversity-Oriented Organic Synthesis in Drug Discovery", Science 287, 1964-1969 (2000).

Castrillon, et al., "Suppression of Ovarian Follicle Activation in Mice by the Transcription Factor Foxo3a", Science 301, 215-218 2003.

Shalaby, et al., "Development of Humanized Bispecitic Antibodies Reactive with Cytotoxic Lymphocytes and Tumor Cells Overexpressing the HER2 Protooncogene", J. Exp. Med. vol. 175 Jan. 1992 217-225.

Shen, et al.,"Evidence for SH3 domain directed binding and phosphorylation of Sam68 by Src", Oncogene 18 4647-4653 (1999).

Spira, et al.,"The identification of monoclonal class switch variants by Sib Selection and an ELISA Assay", Journal of Immunological Methods, 74 (1984) 307-315.

Steplewski, et al., "Isolation and characterization of anti-monosialoganglioside monoclonal antibody 19-9 class-switch variants", Proc. Nat'l. Acad. Sci., USA vol. 82 pp. 8653-8657, Dec. 1985.

Stryer, et al., "Fluorescence Spectroscopy of Proteins" Science, vol. 162 1968 526-533.

Suresh, et al., "Bispecific monoclonal antibodies from hybrid hybridomas" Methods in Enzymology, vol. 121 1986 210-228.

Tutt, et al., "Trispecific F(ab'), Derivatives That Use Cooperative Signaling Via the TCR/CD3 Complex and CD2 to Activate and Redirect Resting Cytotoxic T Cells'" The Jouhnal of Immunology 147(1):60-9 (1991).

Upstate, et al., "Antibodies for Phosphorylation & Beyond", Internet Article, Jun. 2004, 1-16.

Vadlamudi, et al., "Heregulin and HER2 signaling selectively activates c-Src phosphorylation at tyrosine 215" Febs Letters 543. 2003, 76-80.

Vijapurkar, et al.,"Roles of mitogen- activated protein kinase and phosphoinositide 3'kinase in ErbB2/ErbB3 coreceptor-mediated heregulin signaling" Experimental Cell Research 284, 2003, 291-302.

Walker. et al., "Interaction of Human IgG Chimeric Antibodies With the Human FcRII Receptors: Requirements for Antibody-Mediated Host Cell-Target Cell Interaction" Molecular Immunology, vol. 26 No. 4, pp. 403-411 1989.

Dalva, et al "EphB Receptors Interact with NMDA Receptors and Regulate Excitatory Synapse Formation" Cell 103: 945-956 (2000).

* cited by examiner

| Protein Name | Accession Number | Protein Type | Phospho-Tyr Residue | Phosphorylation Site Sequence | Cell Lines | SEQ ID NO: |
|---|---|---|---|---|---|---|
| afadin | P55196 | Actin binding protein | Y1480 | DLQyITVSKEELSSGDSLSPDPWKR | A431, HT-29 | SEQ ID NO: 1 |
| catenin, delta-1 | O60716 | Actin binding protein | Y174 | TVQPVAMGPDGLPVDASSVSNNyIQTLGR | A431, HT-29 | SEQ ID NO: 2 |
| catenin, delta-1 | O60716 | Actin binding protein | Y213 | NFHYPPDGySR | A431, HT-29 | SEQ ID NO: 3 |
| catenin, delta-1 | O60716 | Actin binding protein | Y248 | YRPSMEGyR | A431, HT-29 | SEQ ID NO: 4 |
| catenin, delta-1 | O60716 | Actin binding protein | Y321 | SyEDMIGEEVPSDQYYWAPLAQHER | HT-29 | SEQ ID NO: 5 |
| catenin, delta-1 | O60716 | Actin binding protein | Y335 | SYEDMIGEEVPSDQYyWAPLAQHER | A431, HT-29 | SEQ ID NO: 6 |
| Lnsp-1 | Q14847 | Actin binding protein | Y122 | TQDQISNIKyHEEFEK | A549 | SEQ ID NO: 7 |
| caveolin-1 | Q03135 | Adaptor/scaffold | Y6 | yVDSEGHLYTVPIR | BxPC-3 | SEQ ID NO: 8 |
| Cbl | P22681 | Adaptor/scaffold | Y455 | QGAEGAPSPNyDDDDDERADDTLFMMK | DU145, H460, HT-29, LNCaP | SEQ ID NO: 9 |
| DLG3 | Q92796 | Adaptor/scaffold | Y673 | RDNEVQGQDyHFVVSR | A431, BxPC-3, HT-29, LNCaP | SEQ ID NO: 10 |
| Hrs | O14964 | Adaptor/scaffold | Y308 | AEPMPSASSAPPASSLySSPVNSSAPLAEDIDPELAR | H460, HCT116 | SEQ ID NO: 11 |
| HSH2 | Q96JZ2 | Adaptor/scaffold | Y265 | GSQDHSGDPTSGDRGyTDPCVATSLK | BxPC-3, LNCaP | SEQ ID NO: 12 |
| IRS-2 | Q8Y4H2 | Adaptor/scaffold | Y653 | SSSSNLGADDGyMPMTPGAALAGSGSGSCR | H460 | SEQ ID NO: 13 |
| IRS-2 | Q8Y4H2 | Adaptor/scaffold | Y675 | SDDyMPMSPASVSAPK | H460 | SEQ ID NO: 14 |
| IRS-2 | Q8Y4H2 | Adaptor/scaffold | Y823 | SYKAPYTCGGDSDQyVLMSSPVGR | H460, HCT116 | SEQ ID NO: 15 |
| liprin beta 1 iso2 | Q86W92-2 | Adaptor/scaffold | Y338 | KGKDGEyEELLNSSSISSLLDAQGFSDLEK | HT-29 | SEQ ID NO: 16 |
| P130Cas | P56945 | Adaptor/scaffold | Y267 | GLLPSQYGQEVyDTPPMAVK | HT-29 | SEQ ID NO: 17 |
| P130Cas | P56945 | Adaptor/scaffold | Y387 | RPGPGTLyDVPR | BxPC-3, DU145, PANC-1 | SEQ ID NO: 18 |
| RPGRIP1 | O95KN7 | Adaptor/scaffold | Y864 | FPVLVTSDLDHyLRR | BxPC-3, HPAC, HT-29 | SEQ ID NO: 19 |
| sciellin | O95171 | Adaptor/scaffold | Y560 | QAGPQDTVVyTR | A431 | SEQ ID NO: 20 |
| sciellin | O95171 | Adaptor/scaffold | Y588 | YIQTVySTSDR | A431 | SEQ ID NO: 21 |
| SH2D4A | Q9H788 | Adaptor/scaffold | Y131 | TKSQyHDLQAPDNQQTK | A549 | SEQ ID NO: 22 |
| Shb | Q15464 | Adaptor/scaffold | Y355 | AGKGESAGyMEPYEAQR | A549, A431, DU145, H460, HT-29, MIAPACA2, PANC-1 | SEQ ID NO: 23 |
| Shb | Q15464 | Adaptor/scaffold | Y423 | LPQDDDRPADEyDQPWEWNR | A431, BxPC-3, HT-29 | SEQ ID NO: 24 |
| STAM1 | Q92783 | Adaptor/scaffold | Y198 | QQSTTLSTLyPSTSSLLTNHQHEGR | A549, HCT116 | SEQ ID NO: 25 |
| STAM2 | O75886 | Adaptor/scaffold | Y192 | SLyPSSEIQLNNK | H460, HT-29, LNCaP | SEQ ID NO: 26 |
| syntenin | O00560 | Adaptor/scaffold | Y46 | VIQAQTAFSANPANPAILSEASAPIPHDGNLyPR | BxPC-3 | SEQ ID NO: 27 |
| TEM6 | Q5IZW7 | Adaptor/scaffold | Y333 | WDSYENLSADGEVLHTQGPVDGSLYAK | A549 | SEQ ID NO: 28 |
| TEM6 | Q5IZW7 | Adaptor/scaffold | Y354 | WDSYENLSADGEVLHTQGPVDGSLyAK | A549 | SEQ ID NO: 29 |
| TEM6 | Q5IZW7 | Adaptor/scaffold | Y584 | KPSVSAQMQAYGQSSySTQTWVR | A549 | SEQ ID NO: 30 |
| TEM6 | Q5IZW7 | Adaptor/scaffold | Y601 | QQQMVVAHQySFAPDGEAR | A549, MIAPACA2 | SEQ ID NO: 31 |
| TEM6 | Q5IZW7 | Adaptor/scaffold | Y780 | KLSLGQyDNDAGGQLPFSK | H460, HT-29, PANC-1 | SEQ ID NO: 32 |
| TEM6 | Q5IZW7 | Adaptor/scaffold | Y802 | AGVGDyAPNLPFPPSPADVK | A549 | SEQ ID NO: 33 |
| ZO1 | Q07157 | Adaptor/scaffold | Y1054 | YESSSyTDQFSR | A431, HT-29 | SEQ ID NO: 34 |
| ZO1 | Q07157 | Adaptor/scaffold | Y1343 | SNHYDPEEDEEyRK | A431 | SEQ ID NO: 35 |
| ZO2 | Q9UDY2 | Adaptor/scaffold | Y911 | MSYLTAMGADyLSCDSR | A431 | SEQ ID NO: 36 |
| Spry3 | O43610 | Adaptor/scaffold; Inhibitor protein | Y27 | STHASNDyVERPPAPCK | H460, LNCaP | SEQ ID NO: 37 |
| DCBLD2 | Q96PD2 | Adhesion | Y621 | EVTTVLQADSAEyAQPLVGGIVGTLHQR | A431, HT-29 | SEQ ID NO: 38 |
| DCBLD2 | Q96PD2 | Adhesion | Y750 | AGKPGLPAPDELVyQVPQSTQEVSGAGR | HT-29 | SEQ ID NO: 39 |
| Erbin | Q96RT1 | Adhesion | Y684 | SHSITNMEIGGLKIyDILSDNGPQQPSTTVK | A431 | SEQ ID NO: 40 |
| mucin 1 | P15941 | Adhesion | Y1209 | DTYHPMSEyPTYHTHGR | A431 | SEQ ID NO: 41 |
| mucin 1 | P15941 | Adhesion | Y1212 | DTYHPMSEYPTyHTHGR | A431 | SEQ ID NO: 42 |
| mucin 1 | P15941 | Adhesion | Y1243 | VSAGNGGSSLSyTNPAVAATSANL | A431 | SEQ ID NO: 43 |
| nectin 1 | Q15223 | Adhesion | Y468 | YDEDACKRPyFTVDEAEAR | BxPC-3 | SEQ ID NO: 44 |
| Ptakophilin 2 | Q99959 | Adhesion | Y166 | AHYTHSDyQYSQR | HT-29 | SEQ ID NO: 45 |
| Ptakophilin 2 | Q99959 | Adhesion | Y168 | AHYTHSDYQySQR | A431 | SEQ ID NO: 46 |
| Ptakophilin 2 | Q99959 | Adhesion | Y845 | AASVLLySLWAHTELHHAYKKAQFK | HCT116 | SEQ ID NO: 47 |
| Ptakophilin 3 | Q9Y446 | Adhesion | Y176 | ADyDTLSLR | A431, BxPC-3, HT-29 | SEQ ID NO: 48 |
| Ptakophilin 3 | Q9Y446 | Adhesion | Y195 | LGPGGLDDRySLVSEQLEPAATSTYR | A549, BxPC-3, HT-29 | SEQ ID NO: 49 |
| Ptakophilin 4 | Q99569 | Adhesion | Y1168 | STTNyVDFYSTK | A549, BxPC-3, HCT116, HT-29 | SEQ ID NO: 50 |
| Ptakophilin 4 | Q99569 | Adhesion | Y157 | SSTQMNSYSDSGyQEAGSFHNSQNVSK | A549 | SEQ ID NO: 51 |
| Ptakophilin 4 | Q99569 | Adhesion | Y372 | TVHDMEQFGQQQYDIyER | LNCaP | SEQ ID NO: 52 |
| Ptakophilin 4 | Q99569 | Adhesion | Y470 | NNyALNTTATYAEPYRPIQYR | BxPC-3, HPAC, HT-29 | SEQ ID NO: 53 |
| URP2 | Q86UX7 | Adhesion | Y11 | TASGDyIDSSWELR | BxPC-3 | SEQ ID NO: 54 |
| zyxin | Q15942 | Adhesion | Y316 | LGHPEALSAGTGSPQPPSFTyAQQR | A431 | SEQ ID NO: 55 |
| desmoglein 2 | Q14126 | Adhesion; Calcium-binding protein | Y1012 | VIQPHGGGSNPLEGTQHLQDVPyVMVR | A431 | SEQ ID NO: 56 |
| Alix | Q8WUM4 | Apoptosis | Y727 | EPSAPSIPTPAyQSSPAGGHAPTPPTPAPR | A549, HT-29 | SEQ ID NO: 57 |
| SLITRK6 | Q9H5Y7 | Axon guidance; Cell surface | Y814 | ANLHAEPDyLEVLEQQT | HT-29 | SEQ ID NO: 58 |
| annexin A2 | P07355 | Calcium-binding protein | Y29 | AyTNFOAERDALNIETAIK | A549, A431, HT-29 | SEQ ID NO: 59 |
| annexin A4 | P09525 | Calcium-binding protein | Y164 | VLVSLSAGGRDEGNyLDDALVR | A549 | SEQ ID NO: 60 |
| Ov/Br regulation | Q9Y5W4 | Cell cycle regulation | Y260 | NEKAPVDFGyVGIDSILEQMR | HT-29 | SEQ ID NO: 61 |
| CDCP1 | Q96OU7 | Cell surface | Y606 | LATEEPPPRSPPESESEPyTFSHPNNGDVSSK | DU145 | SEQ ID NO: 62 |
| TSRC1 | Q6UY14 | Cell surface | Y159 | SRLRDPIKPGMFGyGR | HCT116 | SEQ ID NO: 63 |
| TBCB | Q99426 | Chaperone; Cytoskeletal protein | Y239 | YGAFVKPAVVTVGDFPEEDyGLDEI | A549 | SEQ ID NO: 64 |
| actinin, alpha 1 | P12814 | Cytoskeletal protein | Y246 | AIMTYVSSFyHAFSGAQK | A549, PANC-1 | SEQ ID NO: 65 |
| claudin 3 | O15551 | Cytoskeletal protein | Y214 | STGPGASLGTGyDR | HT-29 | SEQ ID NO: 66 |
| claudin 4 | O14493 | Cytoskeletal protein | Y208 | SAAASNyV | BxPC-3 | SEQ ID NO: 67 |
| Cytokeratin 18 | P05783 | Cytoskeletal protein | Y23 | SLGSVQAPSyGARPVSSAASVYAGAGGSGSR | A549, HCT116, HT-29 | SEQ ID NO: 68 |
| Cytokeratin 19 | P08727 | Cytoskeletal protein | Y391 | SLLEGQEDHyNNLSASK | A431 | SEQ ID NO: 69 |
| Cytokeratin 7 | P08729 | Cytoskeletal protein | Y39 | LSSARPGGLGSSSLyGLGASRPR | A549, A431, BxPC-3, DU145, HPAC | SEQ ID NO: 70 |
| Cytokeratin 8 | P05787 | Cytoskeletal protein | Y436 | ITTSGYAGGLSSAYGGLTSPGLSySLGSSFGSGAGSSSFSH | HT-29 | SEQ ID NO: 71 |
| EHM2 iso2 | Q9H329-2 | Cytoskeletal protein | Y479 | ASASGDDSHFDyVHDQNQK | LNCaP | SEQ ID NO: 72 |
| ELMO2 | Q96JJ3 | Cytoskeletal protein | Y49 | EVCDGWSLPNPEYyTLR | A549 | SEQ ID NO: 73 |
| keratin, hair, basic 1 | Q14533 | Cytoskeletal protein | Y282 | AQyDDIVTR | A549 | SEQ ID NO: 74 |
| plectin 1 | Q15149 | Cytoskeletal protein | Y4611 | GyYSPYSVSGSGSTAGSR | A431, BxPC-3 | SEQ ID NO: 75 |
| SM22-alpha | P37802 | Cytoskeletal protein | Y192 | GASQAGMTGyGMPR | HT-29 | SEQ ID NO: 76 |
| talin 1 | Q9Y490 | Cytoskeletal protein | Y26 | TMQFEPSTMVyDACR | H460 | SEQ ID NO: 77 |
| cortactin | Q14247 | Cytoskeletal protein; Actin binding protein | Y154 | HASQKDySSGFGGK | A431 | SEQ ID NO: 78 |
| desmoplakin 3 | P14923 | Cytoskeletal protein; Adhesion | Y19 | VTEWQQTyTYDSGIHSGANTCVPSVSSK | A431 | SEQ ID NO: 79 |
| desmoplakin 3 | P14923 | Cytoskeletal protein; Adhesion | Y73 | KTTTYTQGVPPSCGDLEyQMSTTAR | BxPC-3 | SEQ ID NO: 80 |
| ZFP42 | Q8WXE2 | DNA binding protein | Y146 | ELPQKIVGENSLEYSEyMTGK | H460 | SEQ ID NO: 81 |
| ZNF185 | Q15231 | DNA binding protein | Y349 | GILFVKEyVNASEVSSGKPVSAR | A431 | SEQ ID NO: 82 |
| Nuf2 | Q9BZD4 | DNA replication | Y433 | TALEKyHDGIEKAAEDSYAKIDEKTAELK | HCT116 | SEQ ID NO: 83 |
| Smc5 | O96SB9 | DNA replication | Y246 | yKQDVERFYERK | H460 | SEQ ID NO: 84 |
| G6PD | P11413 | Enzyme, cellular metabolism | Y111 | NSYVAGQyDDAASYQR | A549 | SEQ ID NO: 85 |
| G6PD | P11413 | Enzyme, cellular metabolism | Y502 | RVGFQyEGTYK | A549, H460 | SEQ ID NO: 86 |
| G6PD | P11413 | Enzyme, cellular metabolism | Y506 | VGFQYEGTyK | A549, BxPC-3, H460 | SEQ ID NO: 87 |
| MIG-6 | Q9UJM3 | GTPase activating protein, Rac/Rho | Y394 | KVSSTHyYLLPERPPYLDKYEK | A431, MIAPACA2, PANC-1 | SEQ ID NO: 88 |
| MIG-6 | Q9UJM3 | GTPase activating protein, Rac/Rho | Y395 | VSSTHYyLLPERPPYLDKYEK | A431, HCT116, HPAC, MIAPACA2, PANC-1 | SEQ ID NO: 89 |
| RhoGAP p190B | Q13017 | GTPase activating protein, Rac/Rho | Y1108 | GYSDEIyVPDDSQNR | A549, BxPC-3, DU145 | SEQ ID NO: 90 |
| ARHGEF5 | Q12774 | Guanine nucleotide exchange factor, Rac/Rho | Y19 | LINSSQLLyQEYSDVVLNK | HT-29 | SEQ ID NO: 91 |
| BCAR3 | O75815 | Guanine nucleotide exchange factor, Ras | Y266 | CLEEHyGTSPGQAR | MIAPACA2 | SEQ ID NO: 92 |
| BST1 | Q10588 | Hydrolase | Y134 | FMPLSDVLyGRVADFLSWCR | H460 | SEQ ID NO: 93 |
| Na,K-ATPase 1 | P05023 | Hydrolase, non-esterase | Y260 | GIVVyTGDRTVMGR | H460 | SEQ ID NO: 94 |
| NEPH1 | Q7Z696 | Immunoglobulin superfamily | Y520 | GPASDYGPEPTPPGPAAPAGTDTTSQLSyENYEK | MIAPACA2 | SEQ ID NO: 95 |
| NEPH1 | Q7Z696 | Immunoglobulin superfamily | Y523 | GPASDYGPEPTPPGPAAPAGTDTTSQLSYENyEK | MIAPACA2 | SEQ ID NO: 96 |
| SLAMF7 | Q9NY08 | Immunoglobulin superfamily | Y284 | ETPNICPHSGENTEyDTIPHTNR | A431 | SEQ ID NO: 97 |
| PI3K C2beta | O00750 | Kinase, lipid | Y228 | LLGSVDyQGINDAITR | H460, HT-29, LNCaP | SEQ ID NO: 98 |

| | A | B | C | D | E | F | G |
|---|---|---|---|---|---|---|---|
| 100 | PI3K p85-beta | O00459 | Kinase, lipid | Y467 | SREYDQLYEEyTR | LNCaP | SEQ ID NO: 99 |
| 101 | PI3K p85-beta | O00459 | Kinase, lipid | Y605 | NETEDQyALMEDEDDLPHHEER | HCT116, LNCaP | SEQ ID NO: 100 |
| 102 | ephrin-B1 | P98172 | Ligand, receptor tyrosine kinase | Y313 | TTENNyCPHYEK | BxPC-3, HT-29 | SEQ ID NO: 101 |
| 103 | ephrin-B1 | P98172 | Ligand, receptor tyrosine kinase | Y317 | TTENNYCPHyEK | BxPC-3, HT-29 | SEQ ID NO: 102 |
| 104 | PLEKHA5 | Q9HAU0 | Lipid binding protein | Y366 | LNSLPSEYESGSACPAQTVHyRPINLSSSENK | A431 | SEQ ID NO: 103 |
| 105 | PLEKHA5 | Q9HAU0 | Lipid binding protein | Y436 | GVISyQTLPR | A431 | SEQ ID NO: 104 |
| 106 | PLEKHA6 | Q9Y2H5 | Lipid binding protein | Y493 | SEDIyADPAAYVMR | HT-29 | SEQ ID NO: 105 |
| 107 | Myosin VI | Q9UM54 | Motor protein | Y1114 | SVTDyDFAPFLNNSPQQNPAAQIPAR | A431, HPAC, LNCaP | SEQ ID NO: 106 |
| 108 | Myosin VI | Q9UM54 | Motor protein | Y1159 | IPFIRPADQyKDPQSK | LNCaP | SEQ ID NO: 107 |
| 109 | ARL-1 | O60218 | Oxidoreductase | Y315 | ACNVLQSSHLEDYPFDAEy | A549 | SEQ ID NO: 108 |
| 110 | meltrin gamma | O13443 | Protease (non-proteasomal) | Y615 | VSSQGNLIPARPAPAPPLySSLT | A431 | SEQ ID NO: 109 |
| 111 | USP34 | Q70CQ2 | Protease (non-proteasomal) | Y1288 | LLyALEIIFALGKPNR | HCT116 | SEQ ID NO: 110 |
| 112 | BRSK1 | Q8TDC3 | Protein kinase, Ser/Thr (non-receptor), CAMK group, CAMKL family, BRSK subfamily | Y121 | KyLYLVLEHVSGGELFDYLVKK | A431 | SEQ ID NO: 111 |
| 113 | BRSK1 | Q8TDC3 | Protein kinase, Ser/Thr (non-receptor), CAMK group, CAMKL family, BRSK subfamily | Y123 | KYLyLVLEHVSGGELFDYLVKK | A431 | SEQ ID NO: 112 |
| 114 | p38-delta | O15264 | Protein kinase, Ser/Thr (non-receptor), CMGC group, MAPK family, p38 subfamily | Y182 | HADAEMTGyVVTR | HT-29 | SEQ ID NO: 113 |
| 115 | STLK3 | Q9UEW8 | Protein kinase, Ser/Thr (non-receptor), STE group, STE20 family, FRAY subfamily | Y65 | DAyELQEVIGSGATAVVQAALCKPRQER | H460 | SEQ ID NO: 114 |
| 116 | MINK | Q8N4C8 | Protein kinase, Ser/Thr (non-receptor), STE group, STE20 family, MSN subfamily | Y906 | NLLHADSNGyTNLPDVVQPSHSPTENSK | BxPC-3, DU145, HT-29 | SEQ ID NO: 115 |
| 117 | FRK | P42685 | Protein kinase, tyrosine (non-receptor), TK group, Src family, N/A subfamily | Y46 | HGHyFVALFDYQAR | A431 | SEQ ID NO: 116 |
| 118 | Fyn | P06241 | Protein kinase, tyrosine (non-receptor), TK group, Src family, N/A subfamily | Y212 | KLDNGGyYIITTR | MIAPACA2 | SEQ ID NO: 117 |
| 119 | SHP-2 | Q06124 | Protein phosphatase, tyrosine (non-receptor) | Y63 | IQNTGDYyDLYGGEK | A431, BxPC-3, DU145, HCT116, HPAC, HT-29 | SEQ ID NO: 118 |
| 120 | acid phosphatase 1 | P24666 | Protein phosphatase, tyrosine (non-receptor); Phosphatase (non-protein) | Y131 | QLIIEDPyYGNDSDFETVYQQCVR | A431 | SEQ ID NO: 119 |
| 121 | PTP-kappa | Q15262 | Receptor protein phosphatase, tyrosine | Y858 | YLCEGTESPyQTGQLHPAIR | HT-29 | SEQ ID NO: 120 |
| 122 | similar to PTPRO | XP_291991 | Receptor protein phosphatase, tyrosine | Y830 | AKVKKLTLGMDyMFQVKKVKGKGYSVSVMKKVPIK | A549 | SEQ ID NO: 121 |
| 123 | EGFR | P00533 | Receptor tyrosine kinase, TK group, EGFR family, N/A subfamily | Y998 | MHLPSPTDSNFyR | A549, BxPC-3, DU145, HT-29, LNCaP | SEQ ID NO: 122 |
| 124 | HER2 | P04626 | Receptor tyrosine kinase, TK group, EGFR family, N/A subfamily | Y923 | FTHQSDVWSYGVTVWELMTFGAKPyDGIPAR | HT-29 | SEQ ID NO: 123 |
| 125 | HER3 | P21860 | Receptor tyrosine kinase, TK group, EGFR family, N/A subfamily | Y1307 | AFQGPGHQAPHVHyAR | A431 | SEQ ID NO: 124 |
| 126 | HER3 | P21860 | Receptor tyrosine kinase, TK group, EGFR family, N/A subfamily | Y1328 | SLEATDSAFDNPDyWHSR | HT-29 | SEQ ID NO: 125 |
| 127 | EphA2 | P29317 | Receptor tyrosine kinase, TK group, Eph family, N/A subfamily | Y575 | QSPEDVyFSKSEQLKPLK | BxPC-3 | SEQ ID NO: 126 |
| 128 | EphA2 | P29317 | Receptor tyrosine kinase, TK group, Eph family, N/A subfamily | Y588 | SEQLKPLKTyVDPHTYEDPNQAVLK | A549, BxPC-3, DU145, HCT116, PANC-1 | SEQ ID NO: 127 |
| 129 | EphA2 | P29317 | Receptor tyrosine kinase, TK group, Eph family, N/A subfamily | Y594 | SEQLKPLKTYVDPHTyEDPNQAVLK | A549, A431, BxPC-3, DU145, HCT116, HPAC, HT-29, MIAPACA2, PANC-1 | SEQ ID NO: 128 |
| 130 | EphA4 | P54764 | Receptor tyrosine kinase, TK group, Eph family, N/A subfamily | Y596 | TyVDPFTYEDPNQAVR | H460, HPAC | SEQ ID NO: 129 |
| 131 | EphA4 | P54764 | Receptor tyrosine kinase, TK group, Eph family, N/A subfamily | Y602 | TYVDPFTyEDPNQAVR | H460, HPAC | SEQ ID NO: 130 |
| 132 | EphA5 | P54756 | Receptor tyrosine kinase, TK group, Eph family, N/A subfamily | Y650 | TyIDPHTYEDPNQAVHEFAK | H460 | SEQ ID NO: 131 |
| 133 | EphA5 | P54756 | Receptor tyrosine kinase, TK group, Eph family, N/A subfamily | Y656 | TYIDPHTyEDPNQAVHEFAK | H460 | SEQ ID NO: 132 |
| 134 | EphA7 | Q15375 | Receptor tyrosine kinase, TK group, Eph family, N/A subfamily | Y614 | TYIDPETyEDPNR | HPAC | SEQ ID NO: 133 |
| 135 | EphB3 | P54753 | Receptor tyrosine kinase, TK group, Eph family, N/A subfamily | Y608 | LQQYIAPGMKVyIDPFTYEDPNEAVR | HT-29 | SEQ ID NO: 134 |
| 136 | EphB3 | P54753 | Receptor tyrosine kinase, TK group, Eph family, N/A subfamily | Y792 | FLEDDPSDPTyTSSLGGK | HT-29 | SEQ ID NO: 135 |
| 137 | EphB4 | P54760 | Receptor tyrosine kinase, TK group, Eph family, N/A subfamily | Y574 | EAEySDKHGQYLIGHGTK | HT-29 | SEQ ID NO: 136 |
| 138 | EphB4 | P54760 | Receptor tyrosine kinase, TK group, Eph family, N/A subfamily | Y590 | HGQYLIGHGTKVyIDPFTYEDPNEAVR | BxPC-3 | SEQ ID NO: 137 |
| 139 | EphB4 | P54760 | Receptor tyrosine kinase, TK group, Eph family, N/A subfamily | Y596 | HGQYLIGHGTKVYIDPFTyEDPNEAVR | BxPC-3 | SEQ ID NO: 138 |
| 140 | EphB4 | P54760 | Receptor tyrosine kinase, TK group, Eph family, N/A subfamily | Y774 | FLEENSSDPTyTSSLGGK | BxPC-3, HT-29 | SEQ ID NO: 139 |
| 141 | EphB4 | P54760 | Receptor tyrosine kinase, TK group, Eph family, N/A subfamily | Y987 | SQAKPGTPGGTGGPAPQy | BxPC-3 | SEQ ID NO: 140 |
| 142 | Ron | Q04912 | Receptor tyrosine kinase, TK group, Met family, N/A subfamily | Y1238 | DILDREyYSVQOHR | BxPC-3 | SEQ ID NO: 141 |
| 143 | RAIG1 | O95357 | Receptor, GPCR | Y317 | AYSQEEITQGFEETGDTLyAPYSTHFQLQNQPPQK | A549, HPAC, MIAPACA2 | SEQ ID NO: 142 |
| 144 | RAIG1 | O95357 | Receptor, GPCR | Y320 | AYSQEEITQGFEETGDTLYAPySTHFQLQNQPPQK | A431, HT-29 | SEQ ID NO: 143 |
| 145 | LRP6 | O75581 | Receptor, misc. | Y1577 | SQyLSAEENYESCPPSPYTER | HT-29 | SEQ ID NO: 144 |
| 146 | integrin beta-4 | P16144 | Receptor, misc.; Adhesion | Y1207 | VCAYGAQGEGPySSLVSCR | BxPC-3, HPAC, HT-29 | SEQ ID NO: 145 |
| 147 | APPL2 | Q06481 | Receptor, misc.; Cell surface; DNA binding protein | Y750 | MQNHGyENPTYK | A431, BxPC-3 | SEQ ID NO: 146 |
| 148 | APP | P05067 | Receptor, misc.; Transcription factor; Cell surface; Acetyltransferase | Y762 | MQQNGYENPTyK | A431 | SEQ ID NO: 147 |
| 149 | hnRNP A2/B1 | P22626 | RNA binding protein | Y336 | NMGGPYGGGNyGPGGSGGSGGYGGR | HCT116 | SEQ ID NO: 148 |
| 150 | hnRNP G | P38159 | RNA binding protein | Y214 | DDGySTKDSYSSR | A549 | SEQ ID NO: 149 |
| 151 | RIP | P52594 | RNA binding protein | Y327 | AGLQTAOKyAALANLDNIFSAGQGGDQGSGFGTTGK | BxPC3 | SEQ ID NO: 150 |
| 152 | LISCH | Q86X29 | Transcription factor | Y324 | SSSAGGQGSyVPLLR | HPAC, HT-29 | SEQ ID NO: 151 |
| 153 | LISCH | Q86X29 | Transcription factor | Y503 | SRDPHyDDFR | A431, BxPC-3, HPAC, HT-29 | SEQ ID NO: 152 |
| 154 | STAT3 | P40763 | Transcription factor | Y539 | LLGPGVNySGCQITWAK | A549, BxPC-3, DU145, HT-29 | SEQ ID NO: 153 |
| 155 | TRIM29 | Q14134 | Transcription factor | Y93 | NSNyFSMDSMEGKR | HT-29 | SEQ ID NO: 154 |
| 156 | ZIM3 | Q96PE6 | Transcription factor | Y251 | QKSNLFCHQKMHTKEKPyQCKTCGK | PANC-1 | SEQ ID NO: 155 |
| 157 | TRIP6 | Q15654 | Transcription, coactivator/corepressor | Y123 | QAyEPPPPAYR | A431 | SEQ ID NO: 156 |
| 158 | HNK1ST | O43529 | Transferase | Y305 | EAGIDHLVSyPTIPPGITVYNRTK | DU145, HCT116 | SEQ ID NO: 157 |
| 159 | ABCA10 | Q7Z2I9 | Transporter, ABC | Y46 | YHEMVGVIFSDTFSyRLKFNWGYR | HT-29 | SEQ ID NO: 158 |
| 160 | ABCA10 | Q7Z2I9 | Transporter, ABC | Y54 | YHEMVGVIFSDTFSYRLKFNWGyR | A549 | SEQ ID NO: 159 |
| 161 | ABCB4 | P21439 | Transporter, ABC | Y279 | ELERyQKHLENAKEIGIKK | PANC-1 | SEQ ID NO: 160 |
| 162 | SLC20A2 | Q08357 | Transporter, facilitator; Receptor, misc. | Y377 | IHIDRGPEEKPAQESNyR | A431 | SEQ ID NO: 161 |
| 163 | FAT | Q14517 | Tumor suppressor | Y4244 | HIySDIPPQVPVRPISYTPSIPSDSR | HT-29 | SEQ ID NO: 162 |
| 164 | U8CE7IP3 | Q9BYM8 | Ubiquitin conjugating system | Y320 | NSQEAEVSCPFIDNTySCSGK | A549, BxPC-3, H460, HT-29, LNCaP | SEQ ID NO: 163 |
| 165 | epsin 2 | Q9Y6I9 | Vesicle protein | Y186 | GSSQPNLSTSHSEOEyGK | A549 | SEQ ID NO: 164 |
| 166 | epsin 2 iso2 | Q9Y6I9-2 | Vesicle protein | Y196 | AGGSPASyHGSTSPR | A549 | SEQ ID NO: 165 |
| 167 | SCAMP1 | O15126 | Vesicle protein | Y73 | MPNVPNTQPAIMKPTEEHPAyTQIAK | LNCaP | SEQ ID NO: 166 |
| 168 | SCAMP3 | O14828 | Vesicle protein | Y83 | HyGSYSTQASAAAATAELLK | DU145 | SEQ ID NO: 167 |
| 169 | syntaxin 4 | Q12846 | Vesicle protein | Y115 | AIEPQKEEADENvNSVNTR | BxPC-3 | SEQ ID NO: 168 |

SSSSNLGADDGpYMPmTPGAAALAGSGSGSCR

| Seq # | Seq | b | y | (+1) | | Seq # | Seq | b | y | (+2) |
|---|---|---|---|---|---|---|---|---|---|---|
| 1 | S | 88.1 | 2959.0 | 30 | | 1 | S | 44.5 | 1480.0 | 30 |
| 2 | S | 175.2 | 2871.9 | 29 | | 2 | S | 88.1 | 1436.5 | 29 |
| 3 | S | 262.2 | 2784.9 | 28 | | 3 | S | 131.6 | 1392.9 | 28 |
| 4 | S | 349.3 | 2697.8 | 27 | | 4 | S | 175.2 | 1349.4 | 27 |
| 5 | N | 463.4 | 2610.7 | 26 | | 5 | N | 232.2 | 1305.9 | 26 |
| 6 | L | 576.6 | 2496.6 | 25 | | 6 | L | 288.8 | 1248.8 | 25 |
| 7 | G | 633.6 | 2383.4 | 24 | | 7 | G | 317.3 | 1192.2 | 24 |
| 8 | A | 704.7 | 2326.4 | 23 | | 8 | A | 352.8 | 1163.7 | 23 |
| 9 | D | 819.8 | 2255.3 | 22 | | 9 | D | 410.4 | 1128.2 | 22 |
| 10 | D | 934.9 | 2140.2 | 21 | | 10 | D | 467.9 | 1070.6 | 21 |
| 11 | G | 991.9 | 2025.1 | 20 | | 11 | G | 496.5 | 1013.1 | 20 |
| 12 | Y* | 1235.1 | 1968.1 | 19 | | 12 | Y* | 618.1 | 984.5 | 19 |
| 13 | M | 1366.3 | 1724.9 | 18 | | 13 | M | 683.7 | 863.0 | 18 |
| 14 | P | 1463.4 | 1593.7 | 17 | | 14 | P | 732.2 | 797.4 | 17 |
| 15 | M# | 1610.6 | 1496.6 | 16 | | 15 | M# | 805.8 | 748.8 | 16 |
| 16 | T | 1711.7 | 1349.4 | 15 | | 16 | T | 856.4 | 675.2 | 15 |
| 17 | P | 1808.8 | 1248.3 | 14 | | 17 | P | 904.9 | 624.7 | 14 |
| 18 | G | 1865.9 | 1151.2 | 13 | | 18 | G | 933.5 | 576.1 | 13 |
| 19 | A | 1937.0 | 1094.1 | 12 | | 19 | A | 969.0 | 547.6 | 12 |
| 20 | A | 2008.1 | 1023.0 | 11 | | 20 | A | 1004.5 | 512.0 | 11 |
| 21 | L | 2121.2 | 952.0 | 10 | | 21 | L | 1061.1 | 476.5 | 10 |
| 22 | A | 2192.3 | 838.8 | 9 | | 22 | A | 1096.6 | 419.9 | 9 |
| 23 | G | 2249.3 | 767.7 | 8 | | 23 | G | 1125.2 | 384.4 | 8 |
| 24 | S | 2336.4 | 710.7 | 7 | | 24 | S | 1168.7 | 355.8 | 7 |
| 25 | G | 2393.5 | 623.6 | 6 | | 25 | G | 1197.2 | 312.3 | 6 |
| 26 | S | 2480.6 | 566.6 | 5 | | 26 | S | 1240.8 | 283.8 | 5 |
| 27 | G | 2537.6 | 479.5 | 4 | | 27 | G | 1269.3 | 240.2 | 4 |
| 28 | S | 2624.7 | 422.4 | 3 | | 28 | S | 1312.8 | 211.7 | 3 |
| 29 | C | 2784.8 | 335.3 | 2 | | 29 | C | 1392.9 | 168.2 | 2 |
| 30 | R | 2941.0 | 175.2 | 1 | | 30 | R | 1471.0 | 88.1 | 1 |

| Seq | # | b | y | (+1) |
|---|---|---|---|---|
| L | 1 | 114.2 | — | 17 |
| L | 2 | 227.3 | 1945.1 | 17 |
| G | 3 | 284.4 | 1831.9 | 16 |
| P | 4 | 381.5 | 1718.8 | 15 |
| G | 5 | 438.5 | 1661.7 | 14 |
| V | 6 | 537.7 | 1564.6 | 13 |
| N | 7 | 651.8 | 1507.6 | 12 |
| Y* | 8 | 895.0 | 1408.4 | 11 |
| S | 9 | 982.0 | 1294.3 | 10 |
| G | 10 | 1039.1 | 1051.2 | 9 |
| C | 11 | 1199.2 | 964.1 | 8 |
| C | 12 | 1327.4 | 907.0 | 7 |
| Q | 13 | 1440.5 | 746.9 | 6 |
| I | 14 | 1541.6 | 618.8 | 5 |
| T | 15 | 1727.8 | 505.6 | 4 |
| W | 16 | 1798.9 | 404.5 | 3 |
| A | 17 | 1927.1 | 218.3 | 2 |
| K | | | 147.2 | 1 |

LLGPGVNpYSGCCQITWAK

REAGENTS FOR THE DETECTION OF PROTEIN PHOSPHORYLATION IN EGFR-SIGNALING PATHWAYS

This is a National Stage Application of International Application No. PCT/US04/42940, filed Dec. 21, 2004 which is incorporated herein by reference in its entirety.

FIELD OF THE INVENTION

The invention relates generally to antibodies and peptide reagents for the detection of protein phosphorylation, and to protein phosphorylation in cancer.

BACKGROUND OF THE INVENTION

The activation of proteins by post-translational modification is an important cellular mechanism for regulating most aspects of biological organization and control, including growth, development, homeostasis, and cellular communication. Protein phosphorylation, for example, plays a critical role in the etiology of many pathological conditions and diseases, including cancer, developmental disorders, autoimmune diseases, and diabetes. Yet, in spite of the importance of protein modification, it is not yet well understood at the molecular level, due to the extraordinary complexity of signaling pathways, and the slow development of technology necessary to unravel it.

Protein phosphorylation on a proteome-wide scale is extremely complex as a result of three factors: the large number of modifying proteins, e.g. kinases, encoded in the genome, the much larger number of sites on substrate proteins that are modified by these enzymes, and the dynamic nature of protein expression during growth, development, disease states, and aging. The human genome, for example, encodes over 520 different protein kinases, making them the most abundant class of enzymes known. See Hunter, *Nature* 411: 355-65 (2001). Most kinases phosphorylate many different substrate proteins, at distinct tyrosine, serine, and/or threonine residues. Indeed, it is estimated that one-third of all proteins encoded by the human genome are phosphorylated, and many are phosphorylated at multiple sites by different kinases. See Graves et al., *Pharmacol. Ther.* 82: 111-21 (1999).

Many of these phosphorylation sites regulate critical biological processes and may prove to be important diagnostic or therapeutic targets for molecular medicine. For example, of the more than 100 dominant oncogenes identified to date, 46 are protein kinases. See Hunter, supra. Understanding which proteins are modified by these kinases will greatly expand our understanding of the molecular mechanisms underlying oncogenic transformation. Therefore, the identification of, and ability to detect, phosphorylation sites on a wide variety of cellular proteins is crucially important to understanding the key signaling proteins and pathways implicated in the progression of diseases like cancer.

An important class of signaling proteins is the receptor tyrosine kinase family (RTKs), which act as essential mediators of physiological cell functions such as proliferation, differentiation, motility or survival. On the basis of their structural characteristics RTKs can be classified into 20 subfamilies, which share a homologous domain that specifies the catalytic tyrosine kinase function (Zwick et al., 1999 *Trends in Pharmacological Sciences* 20: 408-412). The RTKs include the epidermal growth factor receptor (EGFR) family, which consists of four closely related receptors: EGFR (HER1), HER2 (ErbB2/neu), the kinase dead HER3, and HER4 (ErbB4) (Casalini et al. (2004) *J. Cell. Physiol* 200: 343-350). Signaling through EGFR is an important component of normal development, and defective signaling through this receptor early in development can be detrimental for embryogenesis and organogenesis (see Casalini et al., supra.)

Aberrant EGFR activity has been implicated in a variety of human solid tumors including lung, bladder, breast, esophageal, head and neck, and gynecological tumors (Smith et al. 2004 *Oncology Research* 14, 175-225). Over-expression of EGFR has also been shown in 53% of malignant gliomas, and a mutated form of EGFR, the type III EGFR deletion mutant (also known as EGFRvIII), is frequently found in human glioblastomas, breast tumors, and meduloblastomas (see Smith et al., supra.). EGFR overexpression in non-small cell lung cancers (NSCLC) is correlated with shorter patient survival times as compared to patients with lower or normal levels of the receptor (Veale et al., 1993 *Br. J. Cancer* 68: 162-165).

EGFR, through its extracellular domain, binds to different ligands, including epidermal growth factor (EGF), tumor growth factor-alpha (TGFalpha), betacellulin, amphiregulin, epiregulin and heregulin (Riese et al. 1998 *Bioassays* 20: 41-48). Ligand binding induces homodimerization, leading to ATP-mediated autophosphorylation or transphosphorylation (by a partner kinase) of EGFR, which in turn activates its kinase function (Russo et al., 1985 *J. Biol. Chem.* 260: 5205-5208). Within EGFR, the sites reported to be most important in terms of receptor phosphorylation and activation are Tyr 1148, Tyr1173, Tyr1068, and Tyr1086 (Downward et al. (1984) *Nature* 311: 483-485; Margolis et al. (1989) *J. Biol. Chem.* 264: 10667-10671). Phosphorylation of these distinct tyrosine residues creates binding sites for numerous proteins, typically containing Src homology 2 (SH2)- and phosphotyrosine binding (PTB)-domains, many of which are either tyrosine phosphorylated enzymes, such as Src or Phospholipase C gamma, or adaptor molecules that link receptor activation to downstream signaling pathways including MAPK-Erk1/2 and PI3K-AKT (see Zwick et al.)

Despite the identification of some of the downstream targets and effectors of EGFR, the molecular mechanisms contributing to EGFR-mediated oncogenesis in a variety of human cancers remain incompletely understood. At the same time, however, interest in EGFR as a therapeutic target has continued to increase, and targeted inhibitors of this RTK are already on the market, or in clinical trials, for a variety of cancers involving activated EGFR. For example, Herceptin®, an inhibitor of HER2/neu, is currently an approved therapy for a certain subset of breast cancer. Iressa™ (ZD1839), a small-molecule inhibitor of EGFR, has recently entered clinical trials for the treatment of breast cancer, while another small molecule inhibitor, Tarceva™ (OSI-774), is in clinical trials for the treatment of non-small cell lung carcinoma (NSCLC). However, the efficacy, mechanism of action, and clinical utility of these compounds in mediating molecular effects downstream of EGFR remain to be seen. Indeed, the limited success thus far observed with these highly specific targeted inhibitors (each targeting only a single protein) evidences that additional signaling molecules beyond just EGFR may be driving these cancers.

For example, 30-50 percent of HER2-positive breast cancers do not respond to the HER2-inhibitor, Herceptin® (see Hortobagyi (2001) *Semin Oncol* 6, Suppl 18: 43-7). These observations, along with recent studies (with Gleevec® and Rapamycin) establishing that combinations of targeted therapeutics may be more effective than single agents (see Mohi et al., *Proc Natl Acad Sci U.S.A.* (2004), 101(9): 3130-5), support the widely-accepted belief that multiple signaling molecules are in fact driving most cancers.

Accordingly, there is a continuing and pressing need to unravel the molecular mechanisms of EGFR-driven oncogenesis by identifying the downstream signaling proteins mediating cellular transformation in diseases involving activated EGFR. Identifying particular phosphorylation sites on such signaling proteins and providing new reagents, such as phospho-specific antibodies and AQUA peptides, to detect and quantify them remains particularly important to advancing our understanding of the biology of these cancers.

Presently, a handful of compounds targeting EGFR are in or entering clinical trials for the treatment of various cancers, including breast and lung. Although the activation and/or expression of EGFR itself can be detected, it is clear that other downstream effectors of EGFR signaling, having diagnostic, predictive, or therapeutic value, remain to be elucidated. Identification of downstream signaling molecules and phospho-sites involved in the progression of EGFR-driven cancers, and development of new reagents to detect and quantify these sites and proteins, may lead to improved diagnostic/prognostic markers, as well as novel drug targets, for the detection and treatment of these diseases.

SUMMARY OF THE INVENTION

The invention discloses 168 novel phosphorylation sites identified in signal transduction proteins and pathways downstream of, and including, EGFR, and provides new reagents, including phosphorylation-site specific antibodies and AQUA peptides, for the selective detection and quantification of these phosphorylated sites/proteins. Also provided are methods of using the reagents of the invention for the detection and quantification of the disclosed phosphorylation sites.

BRIEF DESCRIPTION OF THE DRAWINGS

FIG. 2—Is a table (corresponding to Table 1) enumerating the EGFR signaling protein phosphorylation sites disclosed herein: Column A=the name of the parent protein; Column B the SwissProt accession number for the protein (human sequence); Column C=the protein type/classification; Column D=the tyrosine residue (in the parent protein amino acid sequence) at which phosphorylation occurs within the phosphorylation site; Column E=the phosphorylation site sequence encompassing the phosphorylatable residue (residue at which phosphorylation occurs (and corresponding to the respective entry in Column D) appears in lowercase; and Column F=the cell type(s) in which the phosphorylation site was discovered.

DETAILED DESCRIPTION OF THE INVENTION

Figure 1:
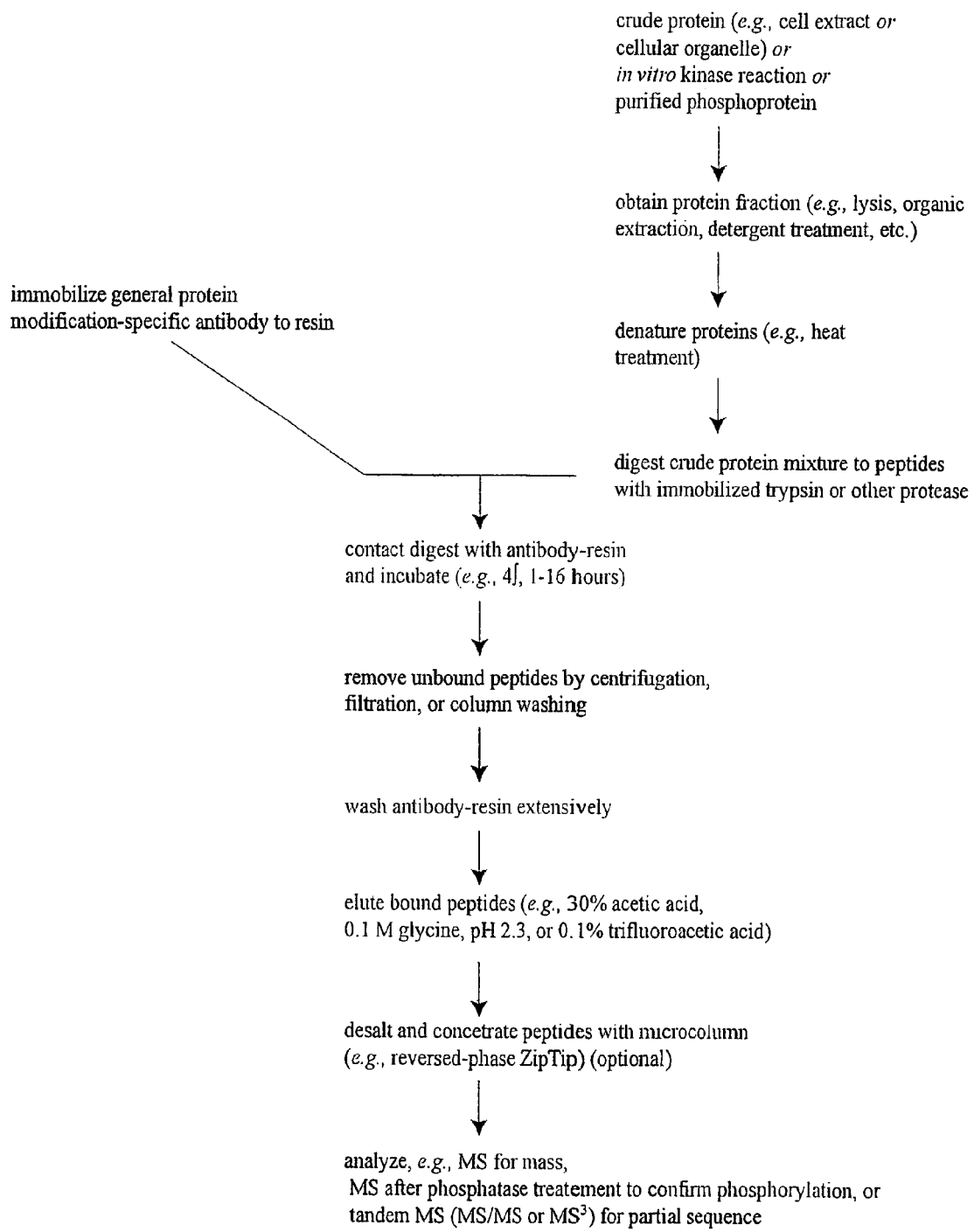
FIG. 1—Is a diagram broadly depicting the immunoaffinity isolation and mass-spectrometric characterization methodology (IAP) employed to identify the novel phosphorylation sites disclosed herein.
Figure 3:
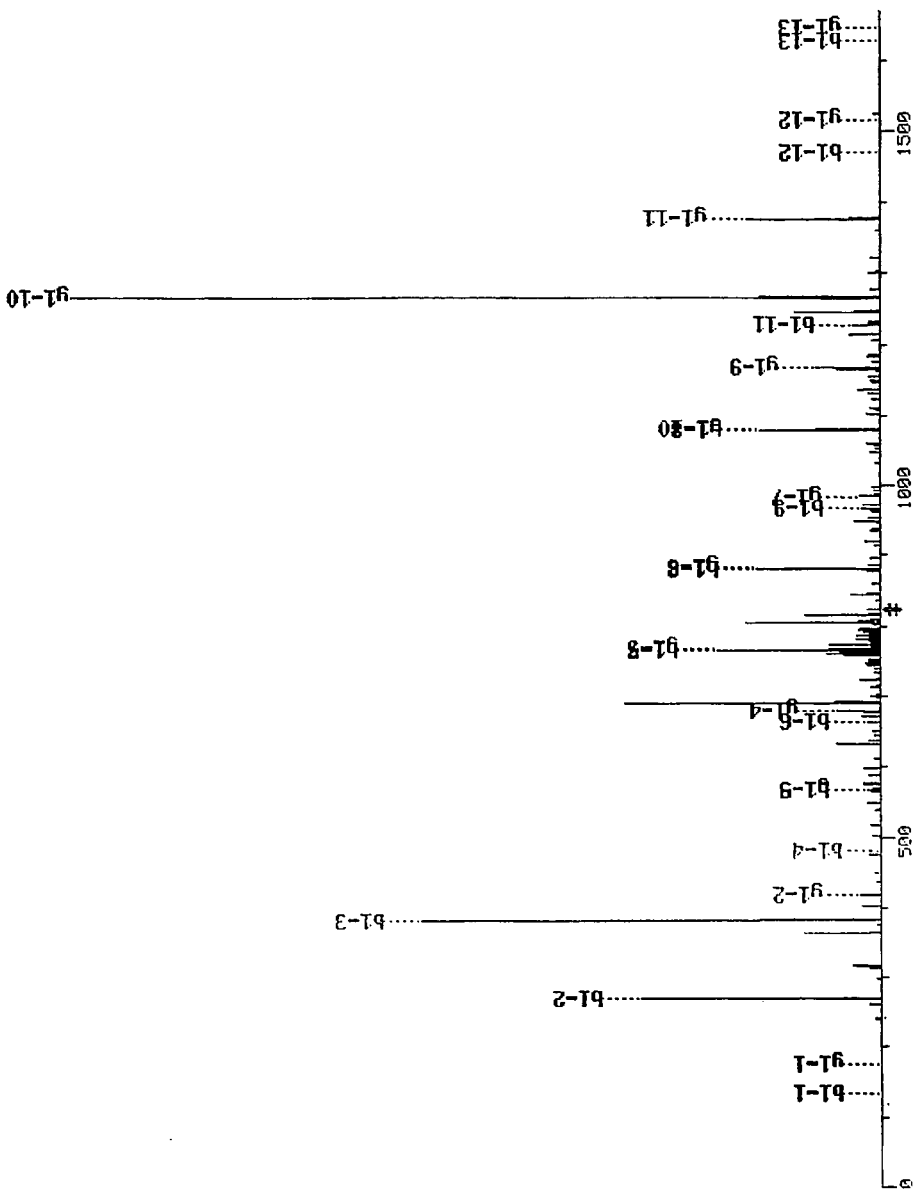
FIG. 3—is an exemplary mass spectrograph depicting the detection of the tyrosine 998 phosphorylation site in EGFR (see Row 123 in FIG. 2/Table 1), as further described in Example 1 (red and blue indicate ions detected in MS/MS spectrum); pY and Y* indicate the phosphorylated tyrosine (shown as lowercase "y" in FIG. 2).
Figure 4:
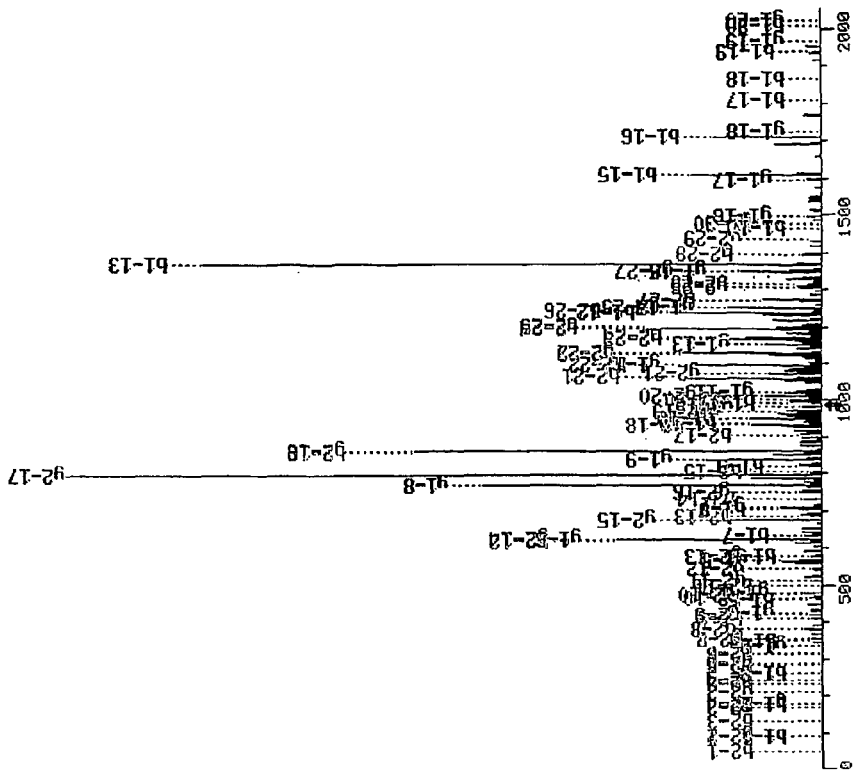
FIG. 4—is an exemplary mass spectrograph depicting the detection of the tyrosine 653 phosphorylation site in insulin receptor substrate-2 (IRS-2) (see Row 14 in FIG. 2/Table 1), as further described in Example 1 (red and blue indicate ions detected in MS/MS spectrum; the purple M# indicates an oxidized methionine residue detected); pY and Y* indicate the phosphorylated tyrosine (shown as lowercase "y" in FIG. 2).
Figure 5:
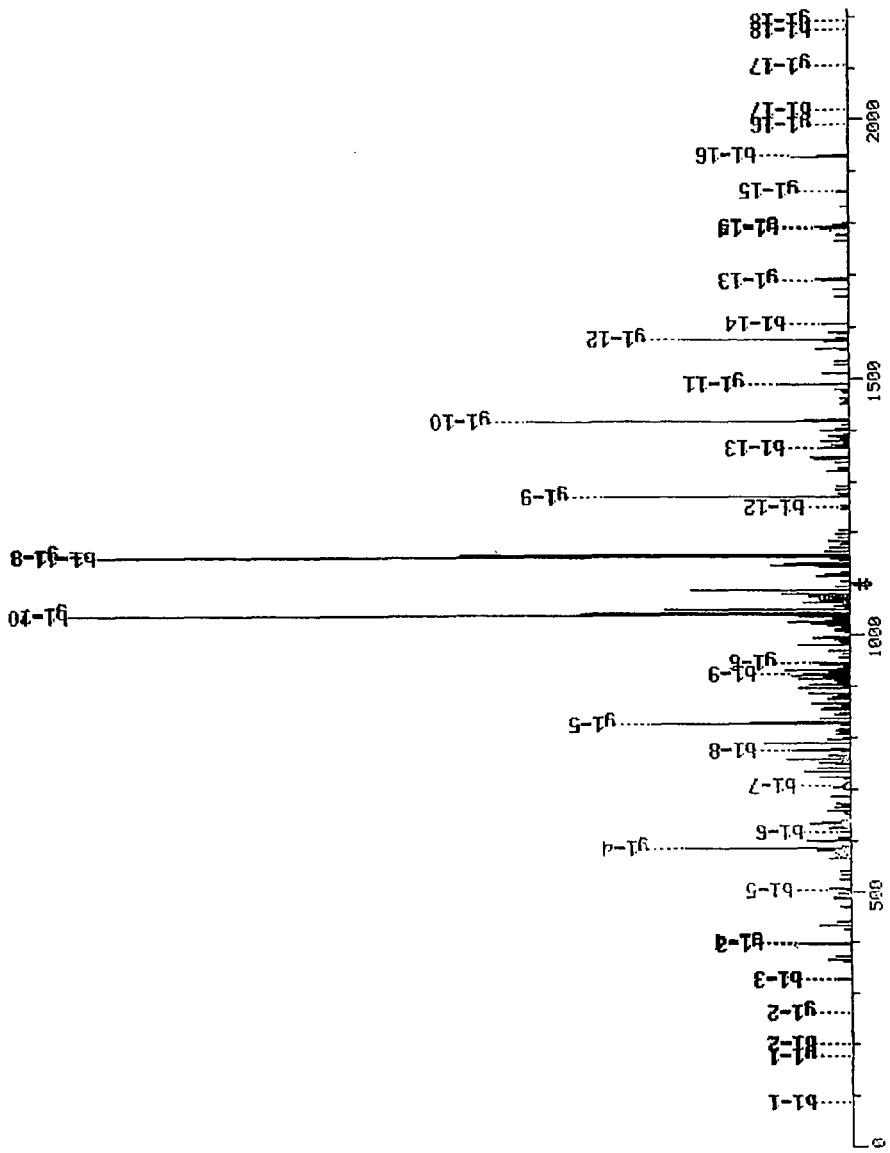
FIG. 5—is an exemplary mass spectrograph depicting the detection of the tyrosine 1328 phosphorylation site in HER-3 (see Row 126 in FIG. 2/Table 1), as further described in Example 1 (red and blue indicate ions detected in MS/MS spectrum); pY and Y* indicate the phosphorylated tyrosine (shown as lowercase "y" in FIG. 2).
Figure 6:
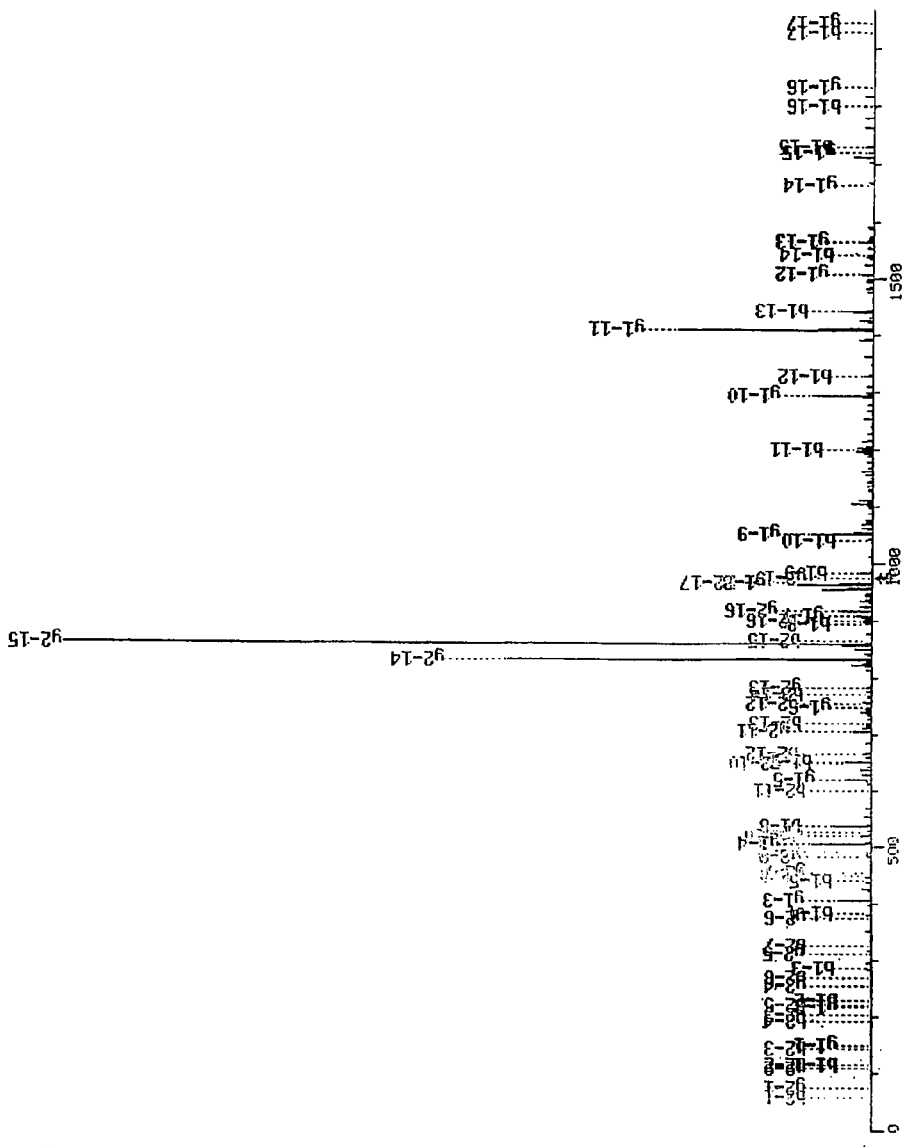
FIG. 6—is an exemplary mass spectrograph depicting the detection of the tyrosine 539 phosphorylation site in STAT-3 (see Row 154 in FIG. 2/Table 1), as further described in Example 1 (red and blue indicate ions detected in MS/MS spectrum); pY and Y* indicate the phosphorylated tyrosine (shown as lowercase "y" in FIG. 2).
Figure 7:
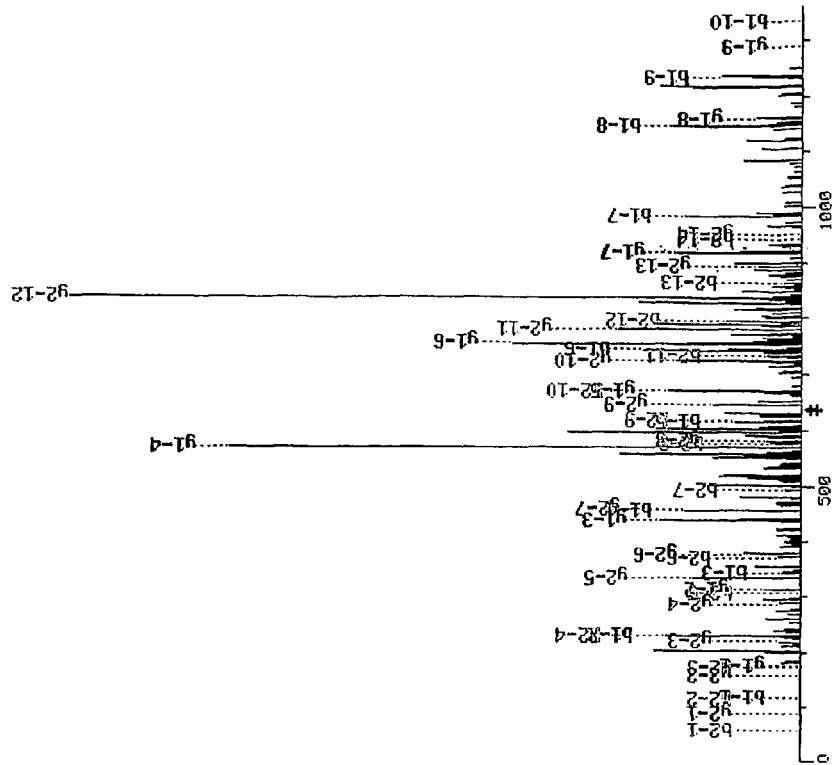
FIG. 7—is an exemplary mass spectrograph depicting the detection of the tyrosine 1238 phosphorylation site in Ron kinase (see Row 142 in FIG. 2/Table 1), as further described in Example 1 (red and blue indicate ions detected in MS/MS spectrum); pY and Y* indicate the phosphorylated tyrosine (shown as lowercase "y" in FIG. 2).

In accordance with the present invention, 168 novel protein phosphorylation sites in signaling proteins and pathways downstream of, and including, the Epidermal Growth Factor Receptor kinase (EGFR) have now been discovered. These newly described phosphorylation sites were identified by employing the techniques described in "Immunoaffinity Isolation of Modified Peptides From Complex Mixtures," U.S. Patent Publication No. 20030044848, Rush et al., using cellular extracts from a variety of tumor derived cell lines, e.g. A549 and HT-29, expressing EGFR and stimulated with EGF, as further described below. The novel phosphorylation sites, and their corresponding parent proteins, disclosed herein are listed in Table 1. These phosphorylation sites correspond to numerous different parent proteins (the full sequences of which (human) are all publicly available in SwissProt database and their Accession numbers listed in Column B of Table 1/FIG. 2), each of which fall into discrete protein type groups, for example Adaptor/Scaffold proteins, Cytoskeletal proteins, Receptor Tyrosine Kinases, and RNA Binding proteins, etc. (see Column C of Table 1), the phosphorylation of which is relevant to signal transduction activity downstream of EGFR, as disclosed herein.

The discovery of the 168 novel protein phosphorylation sites described herein enables the production, by standard methods, of new reagents, such as phosphorylation site-specific antibodies and AQUA peptides (heavy-isotope labeled peptides), capable of specifically detecting and/or quantifying these phosphorylated sites/proteins. Such reagents are highly useful, inter alia, for studying signal transduction events underlying the progression of EGFR-mediated cancers. Accordingly, the invention provides novel reagents—phospho-specific antibodies and AQUA peptides—for the specific detection and/or quantification of an EGFR-related signaling protein/polypeptide only when phosphorylated (or only when not phosphorylated) at a particular phosphorylation site disclosed herein. The invention also provides methods of detecting and/or quantifying one or more phosphorylated EGFR-related signaling proteins using the phosphorylation-site specific antibodies and AQUA peptides of the invention.

In part, the invention provides an isolated phosphorylation site-specific antibody that specifically binds a given EGFR-related signaling protein only when phosphorylated (or not phosphorylated, respectively) at a particular tyrosine enumerated in Column D of Table 1/FIG. 2 comprised within the phosphorylatable peptide site sequence enumerated in corresponding Column E. In further part, the invention provides a heavy-isotope labeled peptide (AQUA peptide) for the detection and quantification of a given EGFR-related signaling protein, the labeled peptide comprising a particular phosphorylatable peptide site/sequence enumerated in Column E of Table 1/FIG. 2 herein. For example, among the reagents provided by the invention is an isolated phosphorylation site-specific antibody that specifically binds the STAT3 transcription factor only when phosphorylated (or only when not phosphorylated) at tyrosine 539 (see Row 154 (and Columns D and E) of Table 1/FIG. 2). By way of further example, among the group of reagents provided by the invention is an AQUA peptide for the quantification of phosphorylated STAT3 protein, the AQUA peptide comprising phosphorylatable peptide sequence listed in Column E, Row 154, of Table 1/FIG. 2 (which encompasses the phosphorylatable tyrosine at position 539).

In one embodiment, the invention provides an isolated phosphorylation site-specific antibody that specifically binds a human EGFR-related signaling protein selected from Column A of Table 1 (Rows 2-169) only when phosphorylated at the tyrosine listed in corresponding Column D of Table 1, comprised within the peptide sequence listed in corresponding Column E of Table 1 (SEQ ID NOs: 1-168), wherein said antibody does not bind said signaling protein when not phosphorylated at said tyrosine. In another embodiment, the invention provides an isolated phosphorylation site-specific antibody that specifically binds an EGFR-related signaling protein selected from Column A of Table 1 only when not phosphorylated at the tyrosine listed in corresponding Column D of Table 1, comprised within the peptide sequence listed in corresponding Column E of Table 1 (SEQ ID NOs: 1-168), wherein said antibody does not bind said signaling protein when phosphorylated at said tyrosine. Such reagents enable the specific detection of phosphorylation (or non-phosphorylation) of a novel phosphorylatable site disclosed herein. The invention further provides immortalized cell lines producing such antibodies. In one preferred embodiment, the immortalized cell line is a rabbit or mouse hybridoma.

In another embodiment, the invention provides a heavy-isotope labeled peptide (AQUA peptide) for the quantification of an EGFR-related signaling protein selected from Column A of Table 1, said labeled peptide comprising the phosphorylatable peptide sequence listed in corresponding Column E of Table 1 (SEQ ID NOs: 1-168), which sequence comprises the phosphorylatable tyrosine listed in corresponding Column D of Table 1. In certain preferred embodiments, the phosphorylatable tyrosine within the labeled peptide is phosphorylated, while in other preferred embodiments, the phosphorylatable tyrosine within the labeled peptide is not phosphorylated.

Reagents (antibodies and AQUA peptides) provided by the invention may conveniently be grouped by the type of EGFR-related signaling protein in which a given phosphorylation site (for which reagents are provided) occurs. The protein types for each respective protein (in which a phosphorylation site has been discovered) are provided in Column C of Table 1/FIG. 2, and include: Actin Binding proteins, Adaptor/Scaffold proteins, Adhesion proteins, Apoptosis proteins, Axon Guidance proteins, Calcium-binding proteins, Cell Cycle Regulation proteins, Cell Surface proteins, Cellular Metabolism enzymes, Chaperones, Cytoskeletal proteins, DNA Binding proteins, DNA Replication proteins, GTPase Activating proteins, Guanine Nucleotide Exchange Factors, Hydrolases, Immunoglobulin Superfamily proteins, Lipid Kinases, Lipid Binding proteins, Motor proteins, Oxidoreductases, Proteases, Protein Kinases, Protein Phosphatases, Receptor Protein Phosphatases, Receptor Tyrosine Kinases, Receptor Tyrosine Kinase ligands, Receptors, RNA Binding proteins, Transcription Factors, Transcription Coactivator/Corepressor proteins, Transferases, Transporter proteins, Tumor Suppressor proteins, Ubitquitin Conjugating System proteins, and Vesicle proteins. Each of these distinct protein groups is considered a preferred subset of EGFR-related signal transduction protein phosphorylation sites disclosed herein, and reagents for their detection/quantification may be considered a preferred subset of reagents provided by the invention.

Particularly preferred subsets of the phosphorylation sites (and their corresponding proteins) disclosed herein are those occurring on the following protein types/groups listed in Column C of Table 1/FIG. 2: Actin Binding proteins, Adaptor/Scaffold proteins, Calcium-Binding Proteins, Cell Cycle Regulation proteins, Cytoskeletal proteins, DNA Binding and Replication Proteins, GTPase Activating proteins, Guanine Nucleotide Exchange Factor proteins, Lipid Kinases, Receptor Tyrosine Kinases, Receptor Tyrosine Kinase ligands, Protein Kinases, Receptor and Protein Phosphatases, Transcription Factor proteins, Tumor Suppressor proteins, and Vesicle proteins. Accordingly, among preferred subsets of reagents provided by the invention are isolated antibodies and AQUA peptides useful for the detection and/or quantification of the foregoing preferred protein/phosphorylation site subsets.

In one subset of preferred embodiments, there is provided:

(i) An antibody that specifically binds an Actin Binding protein selected from Column A, Rows 2-8, of Table 1 only when phosphorylated at the tyrosine listed in corresponding Column D, Rows 2-8, of Table 1, comprised within the phosphorylatable peptide sequence listed in corresponding Column E, Rows 2-8, of Table 1 (SEQ ID NOs: 1-7), wherein said antibody does not bind said protein when not phosphorylated at said tyrosine.

(ii) An equivalent antibody to (i) above that only binds the Actin Binding protein when not phosphorylated at the disclosed site (and does not bind the protein when it is phosphorylated at the site).

(iii) A heavy-isotope labeled peptide (AQUA peptide) for the quantification of an Actin Binding protein selected from Column A, Rows 2-8, said labeled peptide comprising the phosphorylatable peptide sequence listed in corresponding Column E, Rows 2-13, of Table 1 (SEQ ID NOs: 1-7), which sequence comprises the phosphorylatable tyrosine listed in corresponding Column D, Rows 2-8, of Table 1.

Among this preferred subset of reagents, antibodies and AQUA peptides for the detection/quantification of the following Actin Binding protein phosphorylation sites are particularly preferred: Catenin delta-1 (Y174, Y213, Y248, Y321, Y335) (see SEQ ID NOs: 2-6).

In a second subset of preferred embodiments there is provided:

(i) An isolated phosphorylation site-specific antibody that specifically binds a an Adaptor/Scaffold protein selected from Column A, Rows 9-38, of Table 1 only when phosphorylated at the tyrosine listed in corresponding Column D, Rows 9-38, of Table 1, comprised within the phosphorylatable peptide sequence listed in corresponding Column E, Rows 9-38, of Table 1 (SEQ ID NOs: 8-37), wherein said antibody does not bind said protein when not phosphorylated at said tyrosine.

(ii) An equivalent antibody to (i) above that only binds the Adaptor/Scaffold protein when not phosphorylated at the disclosed site (and does not bind the protein when it is phosphorylated at the site).

(iii) A heavy-isotope labeled peptide (AQUA peptide) for the quantification of a an Adaptor/Scaffold protein selected from Column A, Rows 9-38, said labeled peptide comprising the phosphorylatable peptide sequence listed in corresponding Column E, Rows 9-38, of Table 1 (SEQ ID NOs: 8-37), which sequence comprises the phosphorylatable tyrosine listed in corresponding Column D, Rows 9-38, of Table 1.

Among this preferred subset of reagents, antibodies and AQUA peptides for the detection/quantification of the following Adaptor/Scaffold protein phosphorylation sites are particularly preferred: Cbl (Y445), IRS-2 (Y653, Y675, Y823), STAM1 (Y198), and STAM2 (Y113) (see SEQ ID NOs: 9, 13-15, and 25-26).

In another subset of preferred embodiments there is provided:

(i) An isolated phosphorylation site-specific antibody that specifically binds a Calcium-Binding or Cell Cycle Regulation protein selected from Column A, Rows 60-62, of Table 1 only when phosphorylated at the tyrosine listed in corresponding Column D, Rows 60-62, of Table 1, comprised within the phosphorylatable peptide sequence listed in corresponding Column E, Rows 60-62, of Table 1 (SEQ ID NOs: 59-61), wherein said antibody does not bind said protein when not phosphorylated at said tyrosine.

(ii) An equivalent antibody to (i) above that only binds the Calcium-Binding or Cell Cycle Regulation protein when not phosphorylated at the disclosed site (and does not bind the protein when it is phosphorylated at the site).

(iii) A heavy-isotope labeled peptide (AQUA peptide) for the quantification of a Calcium-Binding or Cell Cycle Regulation protein selected from Column A, Rows 60-62, said labeled peptide comprising the phosphorylatable peptide sequence listed in corresponding Column E, Rows 60-62, of Table 1 (SEQ ID NOs: 59-61), which sequence comprises the phosphorylatable tyrosine listed in corresponding Column D, Rows 60-62, of Table 1.

Among this preferred subset of reagents, antibodies and AQUA peptides for the detection/quantification of the following Calcium-Binding or Cell Cycle Regulation protein phosphorylation sites are particularly preferred: Ov/Br Septin (Y260) (see SEQ ID NO: 61).

In another subset of preferred embodiments there is provided:

(i) An isolated phosphorylation site-specific antibody that specifically binds a Cytoskeletal protein selected from Column A, Rows 66-81, of Table 1 only when phosphorylated at the tyrosine listed in corresponding Column D, Rows 66-81, of Table 1, comprised within the phosphorylatable peptide sequence listed in corresponding Column E, Rows 66-81, of Table 1 (SEQ ID NOs: 65-80), wherein said antibody does not bind said protein when not phosphorylated at said tyrosine.

(ii) An equivalent antibody to (i) above that only binds the Cytoskeletal protein when not phosphorylated at the disclosed site (and does not bind the protein when it is phosphorylated at the site).

(iii) A heavy-isotope labeled peptide (AQUA peptide) for the quantification of a Cytoskeletal protein selected from Column A, Rows 66-81, said labeled peptide comprising the phosphorylatable peptide sequence listed in corresponding Column E, Rows 66-81, of Table 1 (SEQ ID NOs: 65-80), which sequence comprises the phosphorylatable tyrosine listed in corresponding Column D, Rows 66-81, of Table 1.

Among this preferred subset of reagents, antibodies and AQUA peptides for the detection/quantification of the following Cytoskeletal protein phosphorylation sites are particularly preferred: Talin-1 (Y26), (see SEQ ID NO: 77).

In still another subset of preferred embodiments there is provided:

(i) An isolated phosphorylation site-specific antibody that specifically binds a DNA Binding or Replication protein selected from Column A, Rows 82-85, of Table 1 only when phosphorylated at the tyrosine listed in corresponding Column D, Rows 82-85, of Table 1, comprised within the phosphorylatable peptide sequence listed in corresponding Column E, Rows 82-85, of Table 1 (SEQ ID NOs: 81-84), wherein said antibody does not bind said protein when not phosphorylated at said tyrosine.

(ii) An equivalent antibody to (i) above that only binds the DNA Binding or Replication protein when not phosphorylated at the disclosed site (and does not bind the protein when it is phosphorylated at the site).

(iii) A heavy-isotope labeled peptide (AQUA peptide) for the quantification of DNA Binding or Replication protein selected from Column A; Rows 82-85, said labeled peptide comprising the phosphorylatable peptide sequence listed in corresponding Column E, Rows 82-85, of Table 1 (SEQ ID NOs: 81-84), which sequence comprises the phosphorylatable tyrosine listed in corresponding Column D, Rows 82-85, of Table 1.

Among this preferred subset of reagents, antibodies and AQUA peptides for the detection/quantification of the following DNA Binding or Replication protein phosphorylation sites are particularly preferred: Smc5 (Y246) (see SEQ ID NO: 84).

In still another subset of preferred embodiments there is provided:

(i) An isolated phosphorylation site-specific antibody that specifically binds a GTPase Activating or Guanine Nucleotide Exchange Factor protein selected from Column A, Rows 89-93, of Table 1 only when phosphorylated at the tyrosine listed in corresponding Column D, Rows 89-93, of Table 1, comprised within the phosphorylatable peptide sequence listed in corresponding Column E, Rows 89-93, of Table 1 (SEQ ID NOs: 88-92), wherein said antibody does not bind said protein when not phosphorylated at said tyrosine.

(ii) An equivalent antibody to (i) above that only binds the GTPase Activating or Guanine Nucleotide Exchange Factor protein when not phosphorylated at the disclosed site (and does not bind the protein when it is phosphorylated at the site).

(iii) A heavy-isotope labeled peptide (AQUA peptide) for the quantification of a GTPase Activating or Guanine Nucleotide Exchange Factor protein selected from Column A, Rows 89-93, said labeled peptide comprising the phosphorylatable peptide sequence listed in corresponding Column E, Rows 89-93, of Table 1 (SEQ ID NOs: 88-92), which sequence comprises the phosphorylatable tyrosine listed in corresponding Column D, Rows 89-93, of Table 1.

Among this preferred subset of reagents, antibodies and AQUA peptides for the detection/quantification of the following GTPase Activating or Guanine Nucleotide Exchange Factor protein phosphorylation sites are particularly preferred: RhoGAP p190B (Y1108), and ARHGEF5 (Y19) (see SEQ ID NOs: 90-91).

In still another subset of preferred embodiments there is provided:

(i) An isolated phosphorylation site-specific antibody that specifically binds a Lipid Kinase selected from Column A, Rows 99-101, of Table 1 only when phosphorylated at the tyrosine listed in corresponding Column D, Rows 99-101, of Table 1, comprised within the phosphorylatable peptide sequence listed in corresponding Column E, Rows 99-101 of Table 1 (SEQ ID NOs: 98-100), wherein said antibody does not bind said protein when not phosphorylated at said tyrosine.

(ii) An equivalent antibody to (i) above that only binds the Lipid Kinase when not phosphorylated at the disclosed site (and does not bind the protein when it is phosphorylated at the site).

(iii) A heavy-isotope labeled peptide (AQUA peptide) for the quantification of a Lipid Kinase selected from Column A, Rows 99-101, said labeled peptide comprising the phosphorylatable peptide sequence listed in corresponding Column E, Rows 99-101, of Table 1 (SEQ ID NOs: 98-100), which sequence comprises the phosphorylatable tyrosine listed in corresponding Column D, Rows 99-101, of Table 1.

Among this preferred subset of reagents, antibodies and AQUA peptides for the detection/quantification of the following Lipid Kinase phosphorylation sites are particularly preferred: PI3K p85-beta (Y467, Y605) (see SEQ ID NOs: 99-100).

In yet another subset of preferred embodiments, there is provided:

(i) An isolated phosphorylation site-specific antibody that specifically binds a Receptor Tyrosine Kinase ligand protein selected from Column A, Rows 102-103, of Table 1 only when phosphorylated at the tyrosine listed in corresponding Column D, Rows 102-103, of Table 1, comprised within the phosphorylatable peptide sequence listed in corresponding Column E, Rows 102-103, of Table 1 (SEQ ID NOs: 101-102), wherein said antibody does not bind said protein when not phosphorylated at said tyrosine.

(ii) An equivalent antibody to (i) above that only binds the Receptor Tyrosine Kinase ligand protein when not phosphorylated at the disclosed site (and does not bind the protein when it is phosphorylated at the site).

(iii) A heavy-isotope labeled peptide (AQUA peptide) for the quantification of an EGFR-related signaling protein that is a Receptor Tyrosine Kinase ligand protein selected from Column A, Rows 102-103, said labeled peptide comprising the phosphorylatable peptide sequence listed in corresponding Column E, Rows 102-103, of Table 1 (SEQ ID NOs: 101-102), which sequence comprises the phosphorylatable tyrosine listed in corresponding Column D, Rows 102-103, of Table 1.

In yet another subset of preferred embodiments, there is provided:

(i) An isolated phosphorylation site-specific antibody specifically binds a Protein Kinase (non-receptor) selected from Column A, Rows 112-118, of Table 1 only when phosphorylated at the tyrosine listed in corresponding Column D, Rows 112-118, of Table 1, comprised within the phosphorylatable peptide sequence listed in corresponding Column E, Rows 112-118, of Table 1 (SEQ ID NOs: 111-117), wherein said antibody does not bind said protein when not phosphorylated at said tyrosine.

(ii) An equivalent antibody to (i) above that only binds the Protein Kinase when not phosphorylated at the disclosed site (and does not bind the protein when it is phosphorylated at the site).

(iii) A heavy-isotope labeled peptide (AQUA peptide) for the quantification of an EGFR-related signaling protein that is a Protein Kinase (non-receptor) selected from Column A, Rows 112-118, said labeled peptide comprising the phosphorylatable peptide sequence listed in corresponding Column E, Rows 112-118, of Table 1 (SEQ ID NOs: 111-117), which sequence comprises the phosphorylatable tyrosine listed in corresponding Column D, Rows 112-118, of Table 1.

Among this preferred subset of reagents, antibodies and AQUA peptides for the detection/quantification of the following Protein Kinase (non-receptor) phosphorylation sites are particularly preferred: BRSK1 (Y121, Y123), MINK (Y906), FRK (Y46), and Fyn (Y212) (see SEQ ID NOs: 111-112, and 115-117).

In yet another subset of preferred embodiments, there is provided:

(i) An isolated phosphorylation site-specific antibody that specifically binds a Protein Phosphatase selected from Column A, Rows 119-122, of Table 1 only when phosphorylated at the tyrosine listed in corresponding Column D, Rows 119-122, of Table 1, comprised within the phosphorylatable peptide sequence listed in corresponding Column E, Rows 119-122, of Table 1 (SEQ ID NOs: 118-121), wherein said antibody does not bind said protein when not phosphorylated at said tyrosine.

(ii) An equivalent antibody to (i) above that only binds the Protein Phosphatase when not phosphorylated at the disclosed site (and does not bind the protein when it is phosphorylated at the site).

(iii) A heavy-isotope labeled peptide (AQUA peptide) for the quantification of an EGFR-related signaling protein that is a Protein Phosphatase selected from Column A, Rows 119-122, said labeled peptide comprising the phosphorylatable peptide sequence listed in corresponding Column E, Rows 119-122, of Table 1 (SEQ ID NOs: 118-121), which sequence comprises the phosphorylatable tyrosine listed in corresponding Column D, Rows 119-122, of Table 1.

Among this preferred subset of reagents, antibodies and AQUA peptides for the detection/quantification of the following Protein Phosphatase phosphorylation sites are particularly preferred: PTP-kappa (Y858) (see SEQ ID NO: 120).

In still another subset of preferred embodiments, there is provided:

(i) An isolated phosphorylation site-specific antibody that specifically binds a Receptor Tyrosine Kinase selected from Column A, Rows 123-142, of Table 1 only when phosphorylated at the tyrosine listed in corresponding Column D, Rows 123-142, of Table 1, comprised within the phosphorylatable peptide sequence listed in corresponding Column E, Rows 123-142, of Table 1 (SEQ ID NOs: 122-141), wherein said antibody does not bind said protein when not phosphorylated at said tyrosine.

(ii) An equivalent antibody to (i) above that only binds the Receptor Tyrosine Kinase when not phosphorylated at the disclosed site (and does not bind the protein when it is phosphorylated at the site).

(iii) A heavy-isotope labeled peptide (AQUA peptide) for the quantification of an EGFR-related signaling protein that is a Receptor Tyrosine Kinase selected from Column A, Rows 123-142, said labeled peptide comprising the phosphorylatable peptide sequence listed in corresponding Column E, Rows 123-142, of Table 1 (SEQ ID NOs: 122-141), which sequence comprises the phosphorylatable tyrosine listed in corresponding Column C, Rows 123-142, of Table 1.

Among this preferred subset of reagents, antibodies and AQUA peptides for the detection/quantification of the following Receptor Tyrosine Kinase phosphorylation sites are particularly preferred: EGFR(Y998), HER2 (Y923), and HER3 (Y1307, Y1328) (see SEQ ID NOs: 122-125).

In still another subset of preferred embodiments, there is provided:

(i) An isolated phosphorylation site-specific antibody that specifically binds a Transcription Factor-Coactivator/Corepressor protein selected from Column A, Rows 152-157, of Table 1 only when phosphorylated at the tyrosine listed in corresponding Column D, Rows 152-157, of Table 1, comprised within the phosphorylatable peptide sequence listed in corresponding Column E, Rows 152-157, of Table 1 (SEQ ID NOs: 151-156), wherein said antibody does not bind said protein when not phosphorylated at said tyrosine.

(ii) An equivalent antibody to (i) above that only binds the Transcription Factor-Coactivator/Corepressor protein when not phosphorylated at the disclosed site (and does not bind the protein when it is phosphorylated at the site).

(iii) A heavy-isotope labeled peptide (AQUA peptide) for the quantification of an EGFR-related signaling protein that is a Transcription Factor-Coactivator/Corepressor protein selected from Column A, Rows 152-157, said labeled peptide comprising the phosphorylatable peptide sequence listed in corresponding Column E, Rows 152-157, of Table 1 (SEQ ID NOs: 151-156), which sequence comprises the phosphorylatable tyrosine listed in corresponding Column D, Rows 152-157, of Table 1.

Among this preferred subset of reagents, antibodies and AQUA peptides for the detection/quantification of the following Transcription Factor-Coactivator/Corepressor protein phosphorylation sites are particularly preferred: STAT3 (Y539) (see SEQ ID NO: 153).

In still another subset of preferred embodiments, there is provided:

(i) An isolated phosphorylation site-specific antibody that specifically binds a Vesicle protein selected from Column A, Rows 165-169, of Table 1 only when phosphorylated at the tyrosine listed in corresponding Column D, Rows 165-169, of Table 1, comprised within the phosphorylatable peptide sequence listed in corresponding Column E, Rows 165-169, of Table 1 (SEQ ID NOs: 164-168), wherein said antibody does not bind said protein when not phosphorylated at said tyrosine.

(ii) An equivalent antibody to (i) above that only binds the Vesicle protein when not phosphorylated at the disclosed site (and does not bind the protein when it is phosphorylated at the site).

(iii) A heavy-isotope labeled peptide (AQUA peptide) for the quantification of an EGFR-related signaling protein that is a Vesicle protein selected from Column A, Rows 165-169, said labeled peptide comprising the phosphorylatable peptide sequence listed in corresponding Column E, Rows 165-169, of Table 1 (SEQ ID NOs: 164-168), which sequence comprises the phosphorylatable tyrosine listed in corresponding Column D, Rows 165-169, of Table 1.

Among this preferred subset of reagents, antibodies and AQUA peptides for the detection/quantification of the following Vesicle protein phosphorylation sites are particularly preferred: Syntaxin 4 (Y115) (see SEQ ID NO: 168).

In yet a further subset of preferred embodiments, there is provided:

(i) An isolated phosphorylation site-specific antibody that specifically binds the FAT tumor suppressor protein only when phosphorylated at tyrosine 4244 (see Column D, Row 163 of Table 1), said tyrosine comprised within the phosphorylatable peptide sequence listed in corresponding Column E, Row 163 of Table 1 (SEQ ID NO: 162), wherein said antibody does not bind said protein when not phosphorylated at said tyrosine.

(ii) An equivalent antibody to (i) above that only binds the FAT tumor suppressor protein when not phosphorylated at the disclosed site (and does not bind the protein when it is phosphorylated at the site).

(iii) A heavy-isotope labeled peptide (AQUA peptide) for the quantification of the FAT tumor suppressor protein, said labeled peptide comprising the phosphorylatable peptide sequence listed in Column E, Row 163 of Table 1 (SEQ ID NO: 162), which sequence comprises the phosphorylatable tyrosine listed in corresponding Column D, Row 163 of Table 1.

The invention also provides, in part, an immortalized cell line producing an antibody of the invention, for example, a cell line producing an antibody within any of the foregoing preferred subsets of antibodies. In one preferred embodiment, the immortalized cell line is a rabbit hybridoma or a mouse hybridoma.

In certain other preferred embodiments, a heavy-isotope labeled peptide (AQUA peptide) of the invention (for example, an AQUA peptide within an of the foregoing preferred subsets of AQUA peptides) comprises a disclosed site sequence wherein the phosphorylatable tyrosine is phosphorylated. In certain other preferred embodiments, a heavy-isotope labeled peptide of the invention comprises a disclosed site sequence wherein the phosphorylatable tyrosine is not phosphorylated.

The foregoing subsets of preferred reagents of the invention should not be construed as limiting the scope of the invention, which, as noted above, includes reagents for the detection and/or quantification of disclosed phosphorylation sites on any of the other protein type/group subsets (each a preferred subset) listed in Column C of Table 1/FIG. 2.

Also provided by the invention are methods for detecting or quantifying an EGFR-related signaling protein that is tyrosine-phosphorylated, said method comprising the step of utilizing one or more of the above-described reagents of the invention to detect or quantify one or more EGFR-related signaling protein(s) selected from Column A of Table 1 only when phosphorylated at the tyrosine listed in corresponding Column D of Table 1. In certain preferred embodiments of the methods of the invention, the reagents comprise a subset of preferred reagents as described above.

The identification of the disclosed novel EGFR-related signaling protein phosphorylation sites, and the standard production and use of the reagents provided by the invention are described in further detail below and in the Examples that follow.

All cited references are hereby incorporated herein, in their entirety, by reference. The Examples are provided to further illustrate the invention, and do not in any way limit its scope, except as provided in the claims appended hereto.

TABLE 1

Newly Discovered EGFR-related Phosphorylation Sites.

| Protein Name | Accession Number | Protein Type | Phospho-Tyr Residue | Phosphorylation Site Sequence | SEQ ID NO: |
|---|---|---|---|---|---|
| afadin | P55196 | Actin binding protein | Y1480 | DLQyITVSKEELSSGDSLSPDPWKR | SEQ ID NO: 1 |
| catenin, delta-1 | O60716 | Actin binding protein | Y174 | TVQPVAMGPDGLPVDASSVSNNyIQTLGR | SEQ ID NO: 2 |
| catenin, delta-1 | O60716 | Actin binding protein | Y213 | NFHYPPDGySR | SEQ ID NO: 3 |
| catenin, delta-1 | O60716 | Actin binding protein | Y248 | YRPSMEGyR | SEQ ID NO: 4 |
| catenin, delta-1 | O60716 | Actin binding protein | Y321 | SyEDMIGEEVPSDQYYWAPLAQHER | SEQ ID NO: 5 |
| catenin, delta-1 | O60716 | Actin binding protein | Y335 | SYEDMIGEEVPSDQYyWAPLAQHER | SEQ ID NO: 6 |
| Lasp-1 | Q14847 | Actin binding protein | Y122 | TQDQISNIKyHEEFEK | SEQ ID NO: 7 |
| caveolin-1 | Q03135 | Adaptor/scaffold | Y6 | yVDSEGHLYTVPIR | SEQ ID NO: 8 |
| Cbl | P22681 | Adaptor/scaffold | Y455 | QGAEGAPSPNyDDDDDERADDTLFMMK | SEQ ID NO: 9 |
| DLG3 | Q92796 | Adaptor/scaffold | Y673 | RDNEVDGQDyHFVVSR | SEQ ID NO: 10 |
| Hrs | O14964 | Adaptor/scaffold | Y308 | AEPMPSASSAPPASSLySSPVNSSAPLAEDIDPELAR | SEQ ID NO: 11 |
| HSH2 | Q96JZ2 | Adaptor/scaffold | Y265 | GSQDHSGDPTSGDRGyTDPCVATSLK | SEQ ID NO: 12 |
| IRS-2 | Q9Y4H2 | Adaptor/scaffold | Y653 | SSSSNLGADDGyMPMTPGAALAGSGSGSCR | SEQ ID NO: 13 |
| IRS-2 | Q9Y4H2 | Adaptor/scaffold | Y675 | SDDyMPMSPASVSAPK | SEQ ID NO: 14 |
| IRS-2 | Q9Y4H2 | Adaptor/scaffold | Y823 | SYKAPYTCGGDSDQyVLMSSPVGR | SEQ ID NO: 15 |
| liprin beta 1 iso2 | Q86W92-2 | Adaptor/scaffold | Y336 | KGKDGEyEELLNSSSISSLLDAQGFSDLEK | SEQ ID NO: 16 |
| P130Cas | P56945 | Adaptor/scaffold | Y267 | GLLPSQYGQEVyDTPPMAVK | SEQ ID NO: 17 |
| P130Cas | P56945 | Adaptor/scaffold | Y387 | RPGPGTLyDVPR | SEQ ID NO: 18 |
| RPGRIP1 | Q96KN7 | Adaptor/scaffold | Y864 | FPVLVTSDLDHyLRR | SEQ ID NO: 19 |
| sciellin | O95171 | Adaptor/scaffold | Y560 | QAGPQDTVVyTR | SEQ ID NO: 20 |
| sciellin | O95171 | Adaptor/scaffold | Y588 | YIQTVySTSDR | SEQ ID NO: 21 |
| SH2D4A | Q9H788 | Adaptor/scaffold | Y131 | TKSQyHDLQAPDNQQTK | SEQ ID NO: 22 |
| Shb | Q15464 | Adaptor/scaffold | Y355 | AGKGESAGyMEPYEAQR | SEQ ID NO: 23 |
| Shb | Q15464 | Adaptor/scaffold | Y423 | LPQDDDRPADEyDQPWEWNR | SEQ ID NO: 24 |

TABLE 1-continued

Newly Discovered EGFR-related Phosphorylation Sites.

| A Protein Name | B Accession Number | C Protein Type | D Phospho-Tyr Residue | E Phosphorylation Site Sequence | G SEQ ID NO: |
|---|---|---|---|---|---|
| 26 STAM1 | Q92783 | Adaptor/scaffold | Y198 | QQSTTLSTLyPSTSSLLTNHQHEGR | SEQ ID NO: 25 |
| 27 STAM2 | O75886 | Adaptor/scaffold | Y192 | SLyPSSEIQLNNK | SEQ ID NO: 26 |
| 28 syntenin | O00560 | Adaptor/scaffold | Y46 | VIQAQTAFSANPANPAILSEASAPIPHDGNLyPR | SEQ ID NO: 27 |
| 29 TEM6 | Q8IZW7 | Adaptor/scaffold | Y333 | WDSyENLSADGEVLHTQGPVDGSLYAK | SEQ ID NO: 28 |
| 30 TEM6 | Q8IZW7 | Adaptor/scaffold | Y354 | WDSYENLSADGEVLHTQGPVDGSLyAK | SEQ ID NO: 29 |
| 31 TEM6 | Q8IZW7 | Adaptor/scaffold | Y584 | KPSVSAQMQAYGQSSySTQTWVR | SEQ ID NO: 30 |
| 32 TEM6 | Q8IZW7 | Adaptor/scaffold | Y601 | QQQMVVAHQySFAPDGEAR | SEQ ID NO: 31 |
| 33 TEM6 | Q8IZW7 | Adaptor/scaffold | Y780 | KLSLGQyDNDAGGQLPFSK | SEQ ID NO: 32 |
| 34 TEM6 | Q8IZW7 | Adaptor/scaffold | Y802 | AGVDyAPNLPPFPSPADVK | SEQ ID NO: 33 |
| 35 ZO1 | Q07157 | Adaptor/scaffold | Y1054 | YESSSyTDQFSR | SEQ ID NO: 34 |
| 36 ZO1 | Q07157 | Adaptor/scaffold | Y1343 | SNHYDPEEDEEYyRK | SEQ ID NO: 35 |
| 37 ZO2 | Q9UDY2 | Adaptor/scaffold | Y911 | MSYLTAMGADyLSCDSR | SEQ ID NO: 36 |
| 38 Spry3 | O43610 | Adaptor/scaffold; Inhibitor protein | Y27 | STHASNDyVERPPAPCK | SEQ ID NO: 37 |
| 39 DCBLD2 | Q96PD2 | Adhesion | Y621 | EVTTVLQADSAEyAQPLVGGIVGTLHQR | SEQ ID NO: 38 |
| 40 DCBLD2 | Q96PD2 | Adhesion | Y750 | AGKPGLPAPDELVyQVPQSTQEVSGAGR | SEQ ID NO: 39 |
| 41 Erbin | Q96RT1 | Adhesion | Y884 | SHSITNMEIGGLKIyDILSDNGPQQPSTTVK | SEQ ID NO: 40 |
| 42 mucin 1 | P15941 | Adhesion | Y1209 | DTYHPMSEyPTYHTHGR | SEQ ID NO: 41 |
| 43 mucin 1 | P15941 | Adhesion | Y1212 | DTYHPMSEYPTyHTHGR | SEQ ID NO: 42 |
| 44 mucin 1 | P15941 | Adhesion | Y1243 | VSAGNGGSSLSyTNPAVAATSANL | SEQ ID NO: 43 |
| 45 nectin 1 | Q15223 | Adhesion | Y468 | YDEDAKRPyFTVDEAEAR | SEQ ID NO: 44 |
| 46 Plakophilin 2 | Q99959 | Adhesion | Y166 | AHYTHSDyQYSQR | SEQ ID NO: 45 |
| 47 Plakophilin 2 | Q99959 | Adhesion | Y168 | AHYTHSDYQySQR | SEQ ID NO: 46 |
| 48 Plakophilin 2 | Q99959 | Adhesion | Y845 | AASVLLySLWAHTELHHAYKKAQFK | SEQ ID NO: 47 |
| 49 Plakophilin 3 | Q9Y446 | Adhesion | Y176 | ADyDTLSLR | SEQ ID NO: 48 |
| 50 Plakophilin 3 | Q9Y446 | Adhesion | Y195 | LGPGGLDDRySLVSEQLEPAATSTYR | SEQ ID NO: 49 |

TABLE 1-continued

Newly Discovered EGFR-related Phosphorylation Sites.

| A<br>Protein<br>Name | B<br>Accession<br>Number | C<br>Protein Type | D<br>Phospho-<br>Tyr<br>Residue | E<br>Phosphorylation Site Sequence | G<br>SEQ ID NO: |
|---|---|---|---|---|---|
| 51 Plako-<br>philin 4 | Q99569 | Adhesion | Y1168 | STTNyVDFYSTK | SEQ ID NO: 50 |
| 52 Plako-<br>philin 4 | Q99569 | Adhesion | Y157 | STQMNSYSDSGyQEAGSFHNSQNVSK | SEQ ID NO: 51 |
| 53 Plako-<br>philin 4 | Q99569 | Adhesion | Y372 | TVHDMEQFGQQQYDIyER | SEQ ID NO: 52 |
| 54 Plako-<br>philin 4 | Q99569 | Adhesion | Y470 | NNyALNTTATYAEPYRPIQYR | SEQ ID NO: 53 |
| 55 URP2 | Q86UX7 | Adhesion | Y11 | TASGDyIDSSWELR | SEQ ID NO: 54 |
| 56 zyxin | Q15942 | Adhesion | Y316 | LGHPEALSAGTGSPQPPSFTyAQQR | SEQ ID NO: 55 |
| 57 Desmo-<br>glein 2 | Q14126 | Adhesion;<br>Calcium-<br>binding<br>protein | Y1012 | VIQPHGGGSNPLEGTQHLQDVPyVMVR | SEQ ID NO: 56 |
| 58 Alix | Q8WUM4 | Apoptosis | Y727 | EPSAPSIPTPAyQSSPAGGHAPTPPTPAPR | SEQ ID NO: 57 |
| 59 SLITRK6 | Q9H5Y7 | Axon<br>guidance;<br>Cell<br>surface | Y814 | ANLHAEPDyLEVLEQQT | SEQ ID NO: 58 |
| 60 annexin<br>A2 | P07355 | Calcium-<br>binding<br>protein | Y29 | AyTNFDAERDALNIETAIK | SEQ ID NO: 59 |
| 61 annexin<br>A4 | P09525 | Calcium-<br>bindng<br>protein | Y164 | VLVSLSAGGRDEGNyLDDALVR | SEQ ID NO: 60 |
| 62 Ov/Br<br>septin | Q9Y5W4 | Cell cycle<br>regulation | Y260 | NEKAPVDFGyVGIDSILEQMR | SEQ ID NO: 61 |
| 63 CDCP1 | Q96QU7 | Cell<br>surface | Y806 | LATEEPPPRSPPESESEPyTFSHPNNGDVSSK | SEQ ID NO: 62 |
| 64 TSRC1 | Q6UY14 | Cell<br>surface | Y159 | SRLRDPIKPGMFGyGR | SEQ ID NO: 63 |
| 65 TBCB | Q99426 | Chaperone;<br>Cytoskeletal<br>protein | Y239 | YGAFVKPAVVTVGDFPEEDyGLDEI | SEQ ID NO: 64 |
| 66 actinin,<br>alpha 1 | P12814 | Cytoskeletal<br>protein | Y246 | AIMTYVSSFyHAFSGAQK | SEQ ID NO: 65 |
| 67 claudin 3 | O15551 | Cytoskeletal<br>protein | Y214 | STGPGASLGTGyDR | SEQ ID NO: 66 |
| 68 claudin 4 | O14493 | Cytoskeletal<br>protein | Y208 | SAAASNyV | SEQ ID NO: 67 |
| 69 Cyto-<br>keratin<br>18 | P05783 | Cytoskeletal<br>protein | Y23 | SLGSVQAPSyGARPVSSAASVYAGAGGSGSR | SEQ ID NO: 68 |
| 70 Cyto-<br>keratin<br>19 | P08727 | Cytoskeletal<br>protein | Y391 | SLLEGQEDHyNNLSASK | SEQ ID NO: 69 |
| 71 Cyto-<br>keratin<br>7 | P08729 | Cytoskeletal<br>protein | Y39 | LSSARPGGLGSSSLyGLGASRPR | SEQ ID NO: 70 |

TABLE 1-continued

Newly Discovered EGFR-related Phosphorylation Sites.

| A Protein Name | B Accession Number | C Protein Type | D Phospho-Tyr Residue | E Phosphorylation Site Sequence | G SEQ ID NO: |
|---|---|---|---|---|---|
| 72 Cyto-keratin 8 | P05787 | Cytoskeletal protein | Y436 | TTSGYAGGLSSAYGGLTSPGLSySLGSSFGSGAGSSSFSR | SEQ ID NO: 71 |
| 73 EHM2 iso2 | Q9H329-2 | Cytoskeletal protein | Y479 | ASASGDDSHFDyVHDQNQK | SEQ ID NO: 72 |
| 74 ELMO2 | Q96JJ3 | Cytoskeletal protein | Y49 | EVCDGSWLPNPEYyTLR | SEQ ID NO: 73 |
| 75 keratin, hair, basic 1 | Q14533 | Cytoskeletal protein | Y282 | AQyDDIVTR | SEQ ID NO: 74 |
| 76 plectin 1 | Q15149 | Cytoskeletal protein | Y4611 | GyYSPYSVSGSGSTAGSR | SEQ ID NO: 75 |
| 77 SM22-alpha | P37802 | Cytoskeletal protein | Y192 | GASQAGMTGyGMPR | SEQ ID NO: 76 |
| 78 talin 1 | Q9Y490 | Cytoskeletal protein | Y26 | TMQFEPSTMVyDACR | SEQ ID NO: 77 |
| 79 cortactin | Q14247 | Cytoskeletal protein; Actin binding protein | Y154 | HASQKDySSGFGGK | SEQ ID NO: 78 |
| 80 Desmo-plakin 3 | P14923 | Cytoskeletal protein; Adhesion | Y19 | VTEWQQTyTYDSGIHSGANTCVPSVSSK | SEQ ID NO: 79 |
| 81 Desmo-plakin 3 | P14923 | Cytoskeletal protein; Adhesion | Y73 | KTTTYTQGVPPSQGDLEyQMSTTAR | SEQ ID NO: 80 |
| 82 ZFP42 | Q8WXE2 | DNA binding protein | Y146 | ELPQKIVGENSLEYSEyMTGK | SEQ ID NO: 81 |
| 83 ZNF185 | O15231 | DNA binding protein | Y349 | GILFVKEyVNASEVSSGKPVSAR | SEQ ID NO: 82 |
| 84 Nul2 | Q9BZD4 | DNA replication | Y433 | TALEKyHDGIEKAAEDSYAKIDEKTAELK | SEQ ID NO: 83 |
| 85 Smc5 | Q96SB9 | DNA replication | Y246 | yKQDVERFYERK | SEQ ID NO: 84 |
| 86 G6PD | P11413 | Enzyme, cellular metabolism | Y111 | NSYVAGQyDDAASYQR | SEQ ID NO: 85 |
| 87 G6PD | P11413 | Enzyme, cellular metabolism | Y502 | RVGFQyEGTYK | SEQ ID NO: 86 |
| 88 G6PD | P11413 | Enzyme, cellular metabolism | Y506 | VGFQYEGTyK | SEQ ID NO: 87 |
| 89 MIG-6 | Q9UJM3 | GTPase activating protein, Rac/Rho | Y394 | KVSSTHyYLLPERPPYLDKYEK | SEQ ID NO: 88 |
| 90 MIG-6 | Q9UJM3 | GTPase activating protein, Rac/Rho | Y395 | VSSTHYyLLPERPPYLDKYEK | SEQ ID NO: 89 |

TABLE 1-continued

Newly Discovered EGFR-related Phosphorylation Sites.

| A Protein Name | B Accession Number | C Protein Type | D Phospho-Tyr Residue | E Phosphorylation Site Sequence | G SEQ ID NO: |
|---|---|---|---|---|---|
| 91 RhoGAP p190B | Q13017 | GTPase activating protein, Rac/Rho | Y1108 | GYSDEIyVVPDDSQNR | SEQ ID NO: 90 |
| 92 ARHGEF5 | Q12774 | Guanine nucleotide exchange factor, Rac/Rho | Y19 | LINSSQLLyQEYSDVVLNK | SEQ ID NO: 91 |
| 93 BCAR3 | O75815 | Guanine nucleotide exchange factor, Ras | Y266 | CLEEHyGTSPGQAR | SEQ ID NO: 92 |
| 94 BST1 | Q10588 | Hydrolase | Y134 | FMPLSDVLyGRVADFLSWCR | SEQ ID NO: 93 |
| 95 Na,K-ATPase 1 | P05023 | Hydrolase, non-esterase | Y260 | GIVVyTGDRTVMGR | SEQ ID NO: 94 |
| 96 NEPH1 | Q7Z696 | Immunoglobulin superfamily | Y520 | GPASDYGPEPTPPGPAAPAGTDTTSQLSyENYEK | SEQ ID NO: 95 |
| 97 NEPH1 | Q7Z696 | Immunoglobulin superfamily | Y523 | GPASDYGPEPTPPGPAAPAGTDTTSQLSYENyEK | SEQ ID NO: 96 |
| 98 SLAMF7 | Q9NY08 | Immunoglobulin superfamily | Y284 | ETPNICPHSGENTEyDTIPHTNR | SEQ ID NO: 97 |
| 99 PI3K C2beta | O00750 | Kinase, lipid | Y228 | LLGSVDyDGINDAITR | SEQ ID NO: 98 |
| 100 PI3K p85-beta | O00459 | Kinase, lipid | Y467 | SREYDQLYEEyTR | SEQ ID NO: 99 |
| 101 PI3K p85-beta | O00459 | Kinase, lipid | Y605 | NETEDQyALMEDEDDLPHHEER | SEQ ID NO: 100 |
| 102 ephrin-B1 | P98172 | Ligand, receptor tyrosine kinase | Y313 | TTENNyCPHYEK | SEQ ID NO: 101 |
| 103 ephrin-B1 | P98172 | Ligand, receptor tyrosine kinase | Y317 | TTENNYCPHyEK | SEQ ID NO: 102 |
| 104 PLEKHA5 | Q9HAU0 | Lipid binding protein | Y366 | LNSLPSEYESGSACPAQTVHyRPINLSSSENK | SEQ ID NO: 103 |
| 105 PLEKHA5 | Q9HAU0 | Lipid binding protein | Y436 | GVISyQTLPR | SEQ ID NO: 104 |
| 106 PLEKHA6 | Q9Y2H5 | Lipid binding protein | Y493 | DESIyADPAAYVMR | SEQ ID NO: 105 |
| 107 Myosin VI | Q9UM54 | Motor protein | Y1114 | SVTDyDFAPFLNNSPQQNPAAQIPAR | SEQ ID NO: 106 |
| 108 Myosin VI | Q9UM54 | Motor protein | Y1159 | IPFIRPADQyKDPQSK | SEQ ID NO: 107 |

TABLE 1-continued

Newly Discovered EGFR-related Phosphorylation Sites.

| A Protein Name | B Accession Number | C Protein Type | D Phospho-Tyr Residue | E Phosphorylation Site Sequence | G SEQ ID NO: |
|---|---|---|---|---|---|
| 109 ARL-1 | O60218 | Oxido-reductase | Y315 | ACNVLQSSHLEDYPFDAEy | SEQ ID NO: 108 |
| 110 meltrin gamma | Q13443 | Protease (non-proteasomal) | Y815 | VSSQGNLIPARPAPAPPLySSLT | SEQ ID NO: 109 |
| 111 USP34 | Q70CQ2 | Protease (non-proteasomal) | Y1288 | LLyALEIIEALGKPNR | SEQ ID NO: 110 |
| 112 BRSK1 | Q8TDC3 | Protein kinase, Ser/Thr (non-receptor) | Y121 | KyLYLVLEHVSGGELFDYLVKK | SEQ ID NO: 111 |
| 113 BRSK1 | Q8TDC3 | Protein kinase, Ser/Thr (non-receptor) | Y123 | KYLyLVLEHVSGGELFDYLVKK | SEQ ID NO: 112 |
| 114 p38-delta | O15264 | Protein kinase, Ser/Thr (non-receptor) | Y182 | HADAEMTGyVVTR | SEQ ID NO: 113 |
| 115 STLK3 | Q9UEW8 | Protein kinase, Ser/Thr (non-receptor) | Y65 | DAyELQEVIGSGATAVVQAALCKPRQER | SEQ ID NO: 114 |
| 116 MINK | Q8N4C8 | Protein kinase, Ser/Thr (non-receptor) | Y906 | NLLHADSNGyTNLPDVVQPSHSPTENSK | SEQ ID NO: 115 |
| 117 FRK | P42685 | Protein kinase, tyrosine (non-receptor) | Y46 | HGHyFVALFDYQAR | SEQ ID NO: 116 |
| 118 Fyn | P06241 | Protein kinase, tyrosine (non-receptor) | Y212 | KLDNGGyYITTR | SEQ ID NO: 117 |
| 119 SHP-2 | Q06124 | Protein phosphatase, tyrosine (non-receptor) | Y63 | IQNTGDYyDLYGGEK | SEQ ID NO: 118 |
| 120 acid phospha-tase 1 | P24666 | Protein phosphatase, tyrosine (non-receptor) | Y131 | QLIIEDPyYGNDSDFETVYQQCVR | SEQ ID NO: 119 |
| 121 PTP-kappa | Q15262 | Receptor protein phosphatase, tyrosine | Y858 | YLCEGTESPyQTGQLHPAIR | SEQ ID NO: 120 |

TABLE 1-continued

Newly Discovered EGFR-related Phosphorylation Sites.

| A Protein Name | B Accession Number | C Protein Type | D Phospho-Tyr Residue | E Phosphorylation Site Sequence | G SEQ ID NO: |
|---|---|---|---|---|---|
| 122 similar to PTPRQ | XP_291991 | Receptor protein phosphatase, tyrosine | Y630 | AKVKKLTLGMDyMFQVKKVKGKGYSVSVMK | SEQ ID NO: 121 |
| 123 EGFR | P00533 | Receptor tyrosine kinase | Y998 | MHLPSPTDSNFyR | SEQ ID NO: 122 |
| 124 HER2 | P04626 | Receptor tyrosine kinase | Y923 | FTHQSDVWSYGVTVWELMTFGAKPyDGIPAR | SEQ ID NO: 123 |
| 125 HER3 | P21860 | Receptor tyrosine kinase | Y1307 | AFQGPGHQAPHVHyAR | SEQ ID NO: 124 |
| 126 HER3 | P21860 | Receptor tyrosine kinase | Y1328 | SLEATDSAFDNPDyWHSR | SEQ ID NO: 125 |
| 127 EphA2 | P29317 | Receptor tyrosine kinase | Y575 | QSPEDVyFSKSEQLKPLK | SEQ ID NO: 126 |
| 128 EphA2 | P29317 | Receptor tyrosine kinase | Y588 | SEQLKPLKTyVDPHTYEDPNQAVLK | SEQ ID NO: 127 |
| 129 EphA2 | P29317 | Receptor tyrosine kinase | Y594 | SEQLKPLKTYVDPHTyEDPNQAVLK | SEQ ID NO: 128 |
| 130 EphA4 | P54764 | Receptor tyrosine kinase | Y596 | TyVDPFTYEDPNQAVR | SEQ ID NO: 129 |
| 131 EphA4 | P54764 | Receptor tyrosine kinase | Y602 | TYVDPFTyEDPNQAVR | SEQ ID NO: 130 |
| 132 EphA5 | P54756 | Receptor tyrosine kinase | Y650 | TyIDPHTYEDPNQAVHEFAK | SEQ ID NO: 131 |
| 133 EphA5 | P54756 | Receptor tyrosine kinase | Y656 | TYIDPHTyEDPNQAVHEFAK | SEQ ID NO: 132 |
| 134 EphA7 | Q15375 | Receptor tyrosine kinase | Y614 | TYIDPETyEDPNR | SEQ ID NO: 133 |
| 135 EphB3 | P54753 | Receptor tyrosine kinase | Y608 | LQQYIAPGMKVyIDPFTYEDPNEAVR | SEQ ID NO: 134 |
| 136 EphB3 | P54753 | Receptor tyrosine kinase | Y792 | FLEDDPSDPTyTSSLGGK | SEQ ID NO: 135 |
| 137 EphB4 | P54760 | Receptor tyrosine kinase | Y574 | EAEySDKHGQYLIGHGTK | SEQ ID NO: 136 |
| 138 EphB4 | P54760 | Receptor tyrosine kinase | Y590 | HGQYLIGHGTKVyIDPFTYEDPNEAVR | SEQ ID NO: 137 |
| 139 EphB4 | P54760 | Receptor tyrosine kinase | Y596 | HGQYLIGHGTKVYIDPFTyEDPNEAVR | SEQ ID NO: 138 |

TABLE 1-continued

Newly Discovered EGFR-related Phosphorylation Sites.

| A Protein Name | B Accession Number | C Protein Type | D Phospho-Tyr Residue | E Phosphorylation Site Sequence | G SEQ ID NO: |
|---|---|---|---|---|---|
| 140 EphB4 | P54760 | Receptor tyrosine kinase | Y774 | FLEENSSDPTyTSSLGGK | SEQ ID NO: 139 |
| 141 EphB4 | P54760 | Receptor tyrosine kinase | Y987 | SQAKPGTPGGTGGPAPQy | SEQ ID NO: 140 |
| 142 Ron | Q04912 | Receptor tyrosine kinase | Y1238 | DILDREySVQQHR | SEQ ID NO: 141 |
| 143 RAIG1 | O95357 | Receptor, GPCR | Y317 | AYSQEEITQGFEETGDTLyAPYSTHFQLQNQPPQK | SEQ ID NO: 142 |
| 144 RAIG1 | O95357 | Receptor, GPCR | Y320 | AYSQEEITQGFEETGDTLYAPySTHFQLQNQPPQK | SEQ ID NO: 143 |
| 145 LRP6 | O75581 | Receptor, misc. | Y1577 | SQyLSAEENYESCPPSPYTER | SEQ ID NO: 144 |
| 146 integrin beta-4 | P16144 | Receptor, misc.; Adhesion | Y1207 | VCAYGAQGEGPySSLVSCR | SEQ ID NO: 145 |
| 147 APPL2 | Q06481 | Receptor, misc.; Cell surface; DNA binding protein | Y750 | MQNHGyENPTYK | SEQ ID NO: 146 |
| 148 APP | P05067 | Receptor, misc.; Transcription factor; Cell surface; | Y762 | MQQNGYENPTyK | SEQ ID NO: 147 |
| 149 hnRNP A2/B1 | P22626 | RNA binding protein | Y336 | NMGGPYGGGNyGPGGSGGSGGYGGR | SEQ ID NO: 148 |
| 150 hnRNP G | P38159 | RNA binding protein | Y214 | DDGySTKDSYSSR | SEQ ID NO: 149 |
| 151 RIP | P52594 | RNA binding protein | Y327 | AGLQTADKyAALANLDNIFSAGQGGDQGSGFGTTGK | SEQ ID NO: 150 |
| 152 LISCH | Q86X29 | Transcription factor | Y324 | SSSAGGQGSyVPLLR | SEQ ID NO: 151 |
| 153 LISCH | Q86X29 | Transcription factor | Y503 | SRDPHyDDFR | SEQ ID NO: 152 |
| 154 STAT3 | Q9BW54 | Transcription factor | Y539 | LLGPGVNySGCQITWAK | SEQ ID NO: 153 |
| 155 TRIM29 | Q14134 | Transcription factor | Y93 | NSNyFSMDSMEGKR | SEQ ID NO: 154 |
| 156 ZIM3 | Q96PE6 | Transcription factor | Y251 | QKSNLFQHQKMHTKEKPyQCKTCGK | SEQ ID NO: 155 |
| 157 TRIP6 | Q15654 | Transcription, coactivator/corepressor | Y123 | QAyEPPPPPAYR | SEQ ID NO: 156 |
| 158 HNK1ST | O43529 | Transferase | Y305 | EAGIDHLVSyPTIPPGITVYNRTK | SEQ ID NO: 157 |
| 159 ABCA10 | Q7Z2I9 | Transporter, ABC | Y46 | YHEMVGVIFSDTFSyRLKFNWGYR | SEQ ID NO: 158 |

TABLE 1-continued

Newly Discovered EGFR-related Phosphorylation Sites.

| A<br>Protein<br>Name | B<br>Accession<br>Number | C<br>Protein Type | D<br>Phospho-<br>Tyr<br>Residue | E<br>Phosphorylation Site Sequence | G<br>SEQ ID NO: |
|---|---|---|---|---|---|
| 160 ABCA10 | Q7Z2I9 | Transporter, ABC | Y54 | YHEMVGVIFSDTFSYRLKFNWGyR | SEQ ID NO: 159 |
| 161 ABCB4 | P21439 | Transporter, ABC | Y279 | ELERyQKHLENAKEIGIKK | SEQ ID NO: 160 |
| 162 SLC20A2 | Q08357 | Transporter, facilitator; Receptor, misc. | Y377 | IHIDRGPEEKPAQESNyR | SEQ ID NO: 161 |
| 163 FAT | Q14517 | Tumor suppressor | Y4244 | NIySDIPPQVPVRPISYTPSIPSDSR | SEQ ID NO: 162 |
| 164 UBCe7IP3 | Q9BYM8 | Ubiquitin conjugating system | Y320 | NSQEAEVSCPFIDNTySCSGK | SEQ ID NO: 163 |
| 165 epsin 2 | O95208 | Vesicle protein | Y186 | GSSQPNLSTSHSEQEyGK | SEQ ID NO: 164 |
| 166 epsin 2 iso2 | O95208-2 | Vesicle protein | Y196 | AGGSPASyHGSTSPR | SEQ ID NO: 165 |
| 167 SCAMP1 | O15126 | Vesicle protein | Y73 | MPNVPNTQPAIMKPTEEHPAyTQIAK | SEQ ID NO: 166 |
| 168 SCAMP3 | O14828 | Vesicle protein | Y83 | NyGSYSTQASAAAATAELLK | SEQ ID NO: 167 |
| 169 syntaxin 4 | Q12846 | Vesicle protein | Y115 | AIEPQKEEADENyNSVNTR | SEQ ID NO: 168 |

The short name for each protein in which a phosphorylation site has presently been identified is provided in Column A, and its SwissProt accession number (human) is provided Column B. The protein type/group into which each protein falls is provided in Column C. The identified tyrosine residue at which phosphorylation occurs in a given protein is identified in Column D, and the amino acid sequence of the phosphorylation site encompassing the tyrosine residue is provided in Column E (lower case y=the tyrosine (identified in Column D)) at which phosphorylation occurs. Table 1 above is identical to FIG. 2, except that the latter includes the cell type(s) in which the particular phosphorylation site was identified (Column F).

The identification of these 168 phosphorylation sites is described in more detail in Part A below and in Example 1.

DEFINITIONS

As used herein, the following terms have the meanings indicated:

"Antibody" or "antibodies" refers to all types of immunoglobulins, including IgG, IgM, IgA, IgD, and IgE, including $F_{ab}$ or antigen-recognition fragments thereof, including chimeric, polyclonal, and monoclonal antibodies. The term "does not bind" with respect to an antibody's binding to one phospho-form of a sequence means does not substantially react with as compared to the antibody's binding to the other phospho-form of the sequence for which the antibody is specific.

"EGFR-related signaling protein" means any protein (or polypeptide derived therefrom) enumerated in Column A of Table 1/FIG. 2, which is disclosed herein as being phosphorylated in one or more EGFR-activated cell line(s). EGFR-related signaling proteins may be direct substrates of EGFR, or may be indirect substrates downstream of EGFR in signaling pathways, or may be EGFR itself. An EGFR-related signaling protein may also be phosphorylated in other cell lines harboring activated kinase activity.

"Heavy-isotope labeled peptide" (used interchangeably with AQUA peptide) means a peptide comprising at least one heavy-isotope label, which is suitable for absolute quantification or detection of a protein as described in WO/03016861, "Absolute Quantification of Proteins and Modified Forms Thereof by Multistage Mass Spectrometry" (Gygi et al.), further discussed below.

"Protein" is used interchangeably with polypeptide, and includes protein fragments and domains as well as whole protein.

"Phosphorylatable amino acid" means any amino acid that is capable of being modified by addition of a phosphate group, and includes both forms of such amino acid.

"Phosphorylatable peptide sequence" means a peptide sequence comprising a phosphorylatable amino acid.

"Phosphorylation site-specific antibody" means an antibody that specifically binds a phosphorylatable peptide sequence/epitope only when phosphorylated, or only when not phosphorylated, respectively. The term is used interchangeably with "phospho-specific" antibody.

A. Identification of Novel EGFR-Related Phosphorylation Sites.

The 168 novel EGFR-related signaling protein phosphorylation sites disclosed herein and listed in Table 1/FIG. 2 were discovered by employing the modified peptide isolation and characterization techniques described in described in "Immunoaffinity Isolation of Modified Peptides From Complex Mixtures," U.S. Patent Publication No. 20030044848, Rush et al. (the teaching of which is hereby incorporated herein by reference, in its entirety) using cellular extracts from the following stably-transfected cell lines expressing EGFR and stimulated with EGF: A431, HCT116, HPAC, MIAPACA2, PANC-1, A549, BxPC-3, DU145, HT-29, H460, and LNCaP. These cell lines are human carcinoma tumor cell lines. The isolation and identification of phosphopeptides from these EGFR-activated cell lines, using an immobilized general phosphotyrosine-specific antibody, is described in detail in Example 1 below. In addition to the 168 previously unknown protein phosphorylation sites discovered, many known phosphorylation sites were also identified (not described herein). The immunoaffinity/mass spectrometric technique described in the '848 patent Publication (the "IAP" method)—and employed as described in detail in the Examples—is briefly summarized below.

The IAP method employed generally comprises the following steps: (a) a proteinaceous preparation (e.g. a digested cell extract) comprising phosphopeptides from two or more different proteins is obtained from an organism; (b) the preparation is contacted with at least one immobilized general phosphotyrosine-specific antibody; (c) at least one phosphopeptide specifically bound by the immobilized antibody in step (b) is isolated; and (d) the modified peptide isolated in step (c) is characterized by mass spectrometry (MS) and/or tandem mass spectrometry (MS-MS). Subsequently, (e) a search program (e.g. Sequest) may be utilized to substantially match the spectra obtained for the isolated, modified peptide during the characterization of step (d) with the spectra for a known peptide sequence. A quantification step employing, e.g. SILAC or AQUA, may also be employed to quantify isolated peptides in order to compare peptide levels in a sample to a baseline.

In the IAP method as employed herein, a general phosphotyrosine-specific monoclonal antibody (commercially available from Cell Signaling Technology, Inc., Beverly, Mass., Cat #9411 (p-Tyr-100)) was used in the immunoaffinity step to isolate the widest possible number of phosphotyrosine containing peptides from the EGFR-activated cell extracts.

Extracts from the following EGFR-activated, human carcinoma tumor cells lines (carcinoma type indicated in brackets) were employed: A431 (skin), HCT116 (colon), HPAC (pancreas), MIAPACA2 (pancreas), PANC-1 (pancreas), A549 (lung), BxPC-3 (pancreas), DU145 (prostate), HT-29 (colon), H460 (lung), and LNCaP (prostate). Each of these cell lines expresses EGFR, which has been activated by stimulation with EGF, thus signaling pathways and proteins downstream of EGFR are affected.

As described in more detail in the Examples, lysates were prepared from these cells line and digested with trypsin after treatment with DTT and iodoacetamide to alkylate cysteine residues. Before the immunoaffinity step, peptides were pre-fractionated by reversed-phase solid phase extraction using Sep-Pak $C_{18}$ columns to separate peptides from other cellular components. The solid phase extraction cartridges were eluted with varying steps of acetonitrile. Each lyophilized peptide fraction was redissolved in PBS and treated with phosphotyrosine antibody (P-Tyr-100, CST #9411) immobilized on protein G-Sepharose. Immunoaffinity-purified peptides were eluted with 0.1% TFA and a portion of this fraction was concentrated with Stage tips and analyzed by LC-MS/MS, using a ThermoFinnigan LCQ Deca XP Plus ion trap mass spectrometer. Peptides were eluted from a 10 cm×75 μm reversed-phase column with a 45-min linear gradient of acetonitrile. MS/MS spectra were evaluated using the program Sequest with the NCBI human protein database.

This revealed a total of 168 novel tyrosine phosphorylation sites in signaling pathways affected by EGFR activation, including one novel site on EGFR itself. The identified phosphorylation sites and their parent proteins are enumerated in Table 1/FIG. 2. The tyrosine (human sequence) at which phosphorylation occurs is provided in Column D, and the peptide sequence encompassing the phosphorylatable tyrosine residue at the site is provided in Column E. FIG. 2 also shows the particular cell line(s) in which a particular phosphorylation site was discovered (see Column F).

As a result of the discovery of these phosphorylation sites, phospho-specific antibodies and AQUA peptides for the detection of and quantification of these sites and their parent proteins may now be produced by standard methods, described below. These new reagents will prove highly useful in, e.g., studying the signaling pathways and events underlying the progression of EGFR-mediated cancers and the identification of new biomarkers and targets for diagnosis and treatment of such diseases.

B. Antibodies and Cell Lines

Isolated phosphorylation site-specific antibodies that specifically bind an EGFR-related signaling protein disclosed in Column A of Table 1 only when phosphorylated (or only when not phosphorylated) at the corresponding amino acid and phosphorylation site listed in Columns D and E of Table 1 may now be produced by standard antibody production methods, such as anti-peptide antibody methods, using the phosphorylation site sequence information provided in Column E of Table 1. For example, two previously unknown HER3 kinase phosphorylation sites (tyrosines 1307 and 1328) (see Rows 125-126 of Table 1/FIG. 2) are presently disclosed. Thus, antibodies that specifically bind any either of these novel HER3 sites can now be produced by immunizing an animal with a peptide antigen comprising all or part of the amino acid sequence encompassing the respective phosphorylated residue (e.g. a peptide antigen comprising the sequence set forth in Row 126, Column E, of Table 1 (SEQ ID NO: 125) (which encompasses the phosphorylated tyrosine at position 1328 in HER3), to produce an antibody that only binds HER3 when phosphorylated at that site.

Polyclonal antibodies of the invention may be produced according to standard techniques by immunizing a suitable animal (e.g., rabbit, goat, etc.) with a peptide antigen corresponding to the EGFR-related phosphorylation site of interest (i.e. a phosphorylation site enumerated in Column E of Table 1, which comprises the corresponding phosphorylatable amino acid listed in Column D of Table 1), collecting immune serum from the animal, and separating the polyclonal antibodies from the immune serum, in accordance with known procedures. For example, a peptide antigen comprising the novel EGFR phosphorylation site disclosed herein (SEQ ID NO: 122=SPTDSNFyRALMDEE, encompassing phosphorylated tyrosine 998 (see Row 123 of Table 1)) may be used to produce antibodies that only bind EGFR when phosphorylated at Tyr998. Similarly, a peptide comprising any of the phosphorylation site sequences provided in Column E of Table 1 may employed as an antigen to produce an antibody that only binds the corresponding protein listed in Column A of Table 1 when phosphorylated (or when not phosphorylated) at the corresponding residue listed in Column D. If an antibody that only binds the protein when phosphorylated at the disclosed site is desired, the peptide antigen includes the phosphorylated form of the amino acid. Conversely, if an antibody that only binds the protein when not phosphorylated at the disclosed site is desired, the peptide antigen includes the non-phosphorylated form of the amino acid.

Peptide antigens suitable for producing antibodies of the invention may be designed, constructed and employed in accordance with well-known techniques. See, e.g., ANTIBODIES: A LABORATORY MANUAL, Chapter 5, p. 75-76, Harlow & Lane Eds., Cold Spring Harbor Laboratory (1988); Czernik, *Methods In Enzymology,* 201: 264-283 (1991); Merrifield, *J. Am. Chem. Soc.* 85:21-49 (1962)).

It will be appreciated by those of skill in the art that longer or shorter phosphopeptide antigens may be employed. See Id. For example, a peptide antigen may consist of the full sequence disclosed in Column E of Table 1, or it may comprise additional amino acids flanking such disclosed sequence, or may comprise of only a portion of the disclosed sequence immediately flanking the phosphorylatable amino acid (indicated in Column E by lowercase "y"). Polyclonal antibodies produced as described herein may be screened as further described below.

Monoclonal antibodies of the invention may be produced in a hybridoma cell line according to the well-known technique of Kohler and Milstein. See *Nature* 265: 495-97 (1975); Kohler and Milstein, *Eur. J. Immunol.* 6: 511 (1976); see also, CURRENT PROTOCOLS IN MOLECULAR BIOLOGY, Ausubel et al. Eds. (1989). Monoclonal antibodies so produced are highly specific, and improve the selectivity and specificity of diagnostic assay methods provided by the invention. For example, a solution containing the appropriate antigen may be injected into a mouse or other species and, after a sufficient time (in keeping with conventional techniques), the animal is sacrificed and spleen cells obtained. The spleen cells are then immortalized by fusing them with myeloma cells, typically in the presence of polyethylene glycol, to produce hybridoma cells. Rabbit fusion hybridomas, for example, may be produced as described in U.S. Pat. No. 5,675,063, C. Knight, Issued Oct. 7, 1997. The hybridoma cells are then grown in a suitable selection media, such as hypoxanthine-aminopterin-thymidine (HAT), and the supernatant screened for monoclonal antibodies having the desired specificity, as described below. The secreted antibody may be recovered from tissue culture supernatant by conventional methods such as precipitation, ion exchange or affinity chromatography, or the like.

Monoclonal Fab fragments may also be produced in *Escherichia coli* by recombinant techniques known to those skilled in the art. See, e.g., W. Huse, *Science* 246:1275-81 (1989); Mullinax et al., *Proc. Nat'l Acad. Sci.* 87:8095 (1990). If monoclonal antibodies of one isotype are preferred for a particular application, particular isotypes can be prepared directly, by selecting from the initial fusion, or prepared secondarily, from a parental hybridoma secreting a monoclonal antibody of different isotype by using the sib selection technique to isolate class-switch variants (Steplewski, et al., *Proc. Nat'l. Acad. Sci.,* 82:8653 (1985); Spira et al., *J. Immunol. Methods,* 74:307 (1984)).

The preferred epitope of a phosphorylation-site specific antibody of the invention is a peptide fragment consisting essentially of about 8 to 17 amino acids including the phosphorylatable tyrosine, wherein about 3 to 8 amino acids are positioned on each side of the phosphorylatable tyrosine (for example, the p-38-delta kinase tyrosine 182 phosphorylation site sequence disclosed in Row 114, Column E of Table 1), and antibodies of the invention thus specifically bind a target EGFR-related polypeptide comprising such epitopic sequence. Particularly preferred epitopes bound by the antibodies of the invention comprise all or part of a phosphorylatable site sequence listed in Column E of Table 1, including the phosphorylatable amino acid.

Included in the scope of the invention are equivalent non-antibody molecules, such as protein binding domains or nucleic acid aptamers, which bind, in a phospho-specific manner, to essentially the same phosphorylatable epitope to which the phospho-specific antibodies of the invention bind. See, e.g., Neuberger et al., *Nature* 312:604 (1984). Such equivalent non-antibody reagents may be suitably employed in the methods of the invention further described below.

Antibodies provided by the invention may be any type of immunoglobulins, including IgG, IgM, IgA, IgD, and IgE, including $F_{ab}$ or antigen-recognition fragments thereof. The antibodies may be monoclonal or polyclonal and may be of any species of origin, including (for example) mouse, rat, rabbit, horse, or human, or may be chimeric antibodies. See, e.g., M. Walker et al., *Molec. Immunol.* 26: 403-11 (1989); Morrision et al., *Proc. Nat'l. Acad. Sci.* 81: 6851 (1984); Neuberger et al., *Nature* 312: 604 (1984)). The antibodies may be recombinant monoclonal antibodies produced according to the methods disclosed in U.S. Pat. No. 4,474,893 (Reading) or U.S. Pat. No. 4,816,567 (Cabilly et al.) The antibodies may also be chemically constructed by specific antibodies made according to the method disclosed in U.S. Pat. No. 4,676,980 (Segel et al.)

The invention also provides immortalized cell lines that produce an antibody of the invention. For example, hybridoma clones, constructed as described above, that produce monoclonal antibodies to the EGFR-related signaling protein phosphorylation sties disclosed herein are also provided. Similarly, the invention includes recombinant cells producing an antibody of the invention, which cells may be constructed by well known techniques; for example the antigen combining site of the monoclonal antibody can be cloned by PCR and single-chain antibodies produced as phage-displayed recombinant antibodies or soluble antibodies in *E. coli* (see, e.g., ANTIBODY ENGINEERING PROTOCOLS, 1995, Humana Press, Sudhir Paul editor.)

Phosphorylation site-specific antibodies of the invention, whether polyclonal or monoclonal, may be screened for epitope and phospho-specificity according to standard techniques. See, e.g. Czernik et al., *Methods in Enzymology,* 201: 264-283 (1991). For example, the antibodies may be screened against the phospho and non-phospho peptide library by ELISA to ensure specificity for both the desired antigen (i.e. that epitope including a phosphorylation site sequence enumerated in Column E of Table 1) and for reactivity only with the phosphorylated (or non-phosphorylated) form of the antigen. Peptide competition assays may be carried out to confirm lack of reactivity with other phospho-epitopes on the given EGFR-related signaling protein. The antibodies may also be tested by Western blotting against cell preparations containing the signaling protein, e.g. cell lines over-expressing the target protein, to confirm reactivity with the desired phosphorylated epitope/target.

Specificity against the desired phosphorylated epitope may also be examined by constructing mutants lacking phosphorylatable residues at positions outside the desired epitope that are known to be phosphorylated, or by mutating the desired phospho-epitope and confirming lack of reactivity. Phosphorylation-site specific antibodies of the invention may exhibit some limited cross-reactivity related epitopes in non-target proteins. This is not unexpected as most antibodies exhibit some degree of cross-reactivity, and anti-peptide antibodies will often cross-react with epitopes having high homology to the immunizing peptide. See, e.g., Czernik, supra. Cross-reactivity with non-target proteins is readily characterized by Western blotting alongside markers of known molecular weight. Amino acid sequences of cross-reacting proteins may be examined to identify sites highly homologous to the EGFR-related signaling protein epitope for which the antibody of the invention is specific.

In certain cases, polyclonal antisera may be exhibit some undesirable general cross-reactivity to phosphotyrosine, which may be removed by further purification of antisera, e.g. over a phosphotyramine column. Antibodies of the invention specifically bind their target protein (i.e. a protein listed in Column A of Table 1) only when phosphorylated (or only when not phosphorylated, as the case may be) at the site disclosed in corresponding Columns D/E, and do not (substantially) bind to the other form (as compared to the form for which the antibody is specific).

Antibodies may be further characterized via immunohistochemical (IHC) staining using normal and diseased tissues to examine EGFR-related phosphorylation and activation status in diseased tissue. IHC may be carried out according to well-known techniques. See, e.g., ANTIBODIES: A LABORATORY MANUAL, Chapter 10, Harlow & Lane Eds., Cold Spring Harbor Laboratory (1988). Briefly, paraffin-embedded tissue (e.g. tumor tissue) is prepared for immunohistochemical staining by deparaffinizing tissue sections with xylene followed by ethanol; hydrating in water then PBS; unmasking antigen by heating slide in sodium citrate buffer; incubating sections in hydrogen peroxide; blocking in blocking solution; incubating slide in primary antibody and secondary antibody; and finally detecting using ABC avidin/biotin method according to manufacturer's instructions.

Antibodies may be further characterized by flow cytometry carried out according to standard methods. See Chow et al., *Cytometry* (*Communications in Clinical Cytometry*) 46: 72-78 (2001). Briefly and by way of example, the following protocol for cytometric analysis may be employed: samples may be centrifuged on Ficoll gradients to remove erythrocytes, and cells may then be fixed with 2% paraformaldehyde for 10 minutes at 37° C. followed by permeabilization in 90% methanol for 30, minutes on ice. Cells may then be stained with the primary phosphorylation-site specific antibody of the invention (which detects an EGFR-related signal transduction protein enumerated in Table 1), washed and labeled with a fluorescent-labeled secondary antibody. Additional fluorochrome-conjugated marker antibodies (e.g. CD45, CD34) may also be added at this time to aid in the subsequent identification of specific hematopoietic cell types. The cells would then be analyzed on a flow cytometer (e.g. a Beckman Coulter FC500) according to the specific protocols of the instrument used.

Antibodies of the invention may also be advantageously conjugated to fluorescent dyes (e.g. Alexa488, PE) for use in multi-parametric analyses along with other signal transduction (phospho-CrkL, phospho-Erk 1/2) and/or cell marker (CD34) antibodies.

Phosphorylation-site specific antibodies of the invention specifically bind to a human EGFR-related signal transduction protein or polypeptide only when phosphorylated at a disclosed site, but are not limited only to binding the human species, per se. The invention includes antibodies that also bind conserved and highly homologous or identical phosphorylation sites in respective EGFR-related proteins from other species (e.g. mouse, rat, monkey, yeast), in addition to binding the human phosphorylation site. Highly homologous or identical sites conserved in other species can readily be identified by standard sequence comparisons, such as using BLAST, with the human EGFR-related signal transduction protein phosphorylation sites disclosed herein.

C. Heavy-Isotope Labeled Peptides (AQUA Peptides).

The novel EGFR-related signaling protein phosphorylation sites disclosed herein now enable the production of corresponding heavy-isotope labeled peptides for the absolute quantification of such signaling proteins (both phosphorylated and not phosphorylated at a disclosed site) in biological samples. The production and use of AQUA peptides for the absolute quantification of proteins (AQUA) in complex mixtures has been described. See WO/03016861, "Absolute Quantification of Proteins and Modified Forms Thereof by Multistage Mass Spectrometry," Gygi et al. and also Gerber et al. *Proc. Natl. Acad. Sci. U.S.A.* 100: 6940-5 (2003) (the teachings of which are hereby incorporated herein by reference, in their entirety).

The AQUA methodology employs the introduction of a known quantity of at least one heavy-isotope labeled peptide standard (which has a unique signature detectable by LC-SRM chromatography) into a digested biological sample in order to determine, by comparison to the peptide standard, the absolute quantity of a peptide with the same sequence and protein modification in the biological sample. Briefly, the AQUA methodology has two stages: peptide internal standard selection and validation and method development; and implementation using validated peptide internal standards to detect and quantify a target protein in sample. The method is a powerful technique for detecting and quantifying a given peptide/protein within a complex biological mixture, such as a cell lysate, and may be employed, e.g., to quantify change in protein phosphorylation as a result of drug treatment, or to quantify differences in the level of a protein in different biological states.

Generally, to develop a suitable internal standard, a particular peptide (or modified peptide) within a target protein sequence is chosen based on its amino acid sequence and the particular protease to be used to digest. The peptide is then generated by solid-phase peptide synthesis such that one residue is replaced with that same residue containing stable isotopes ($^{13}C$, $^{15}N$). The result is a peptide that is chemically identical to its native counterpart formed by proteolysis, but is easily distinguishable by MS via a 7-Da mass shift. A newly synthesized AQUA internal standard peptide is then evaluated by LC-MS/MS. This process provides qualitative information about peptide retention by reverse-phase chromatography, ionization efficiency, and fragmentation via collision-induced dissociation. Informative and abundant fragment ions for sets of native and internal standard peptides are chosen and then specifically monitored in rapid succession as a function of chromatographic retention to form a selected reaction monitoring (LC-SRM) method based on the unique profile of the peptide standard.

The second stage of the AQUA strategy is its implementation to measure the amount of a protein or modified protein from complex mixtures. Whole cell lysates are typically fractionated by SDS-PAGE gel electrophoresis, and regions of the gel consistent with protein migration are excised. This process is followed by in-gel proteolysis in the presence of the AQUA peptides and LC-SRM analysis. (See Gerber et al. supra.) AQUA peptides are spiked in to the complex peptide mixture obtained by digestion of the whole cell lysate with a proteolytic enzyme and subjected to immunoaffinity purification as described above. The retention time and fragmentation pattern of the native peptide formed by digestion (e.g. trypsinization) is identical to that of the AQUA internal standard peptide determined previously; thus, LC-MS/MS analysis using an SRM experiment results in the highly specific and sensitive measurement of both internal standard and analyte directly from extremely complex peptide mixtures. Because an absolute amount of the AQUA peptide is added (e.g. 250 fmol), the ratio of the areas under the curve can be used to determine the precise expression levels of a protein or phosphorylated form of a protein in the original cell lysate. In addition, the internal standard is present during in-gel digestion as native peptides are formed, such that peptide extraction efficiency from gel pieces, absolute losses during sample handling (including vacuum centrifugation), and variability during introduction into the LC-MS system do not affect the determined ratio of native and AQUA peptide abundances.

An AQUA peptide standard is developed for a known phosphorylation site sequence previously identified by the IAP-LC-MS/MS method within in a target protein. One AQUA peptide incorporating the phosphorylated form of the particular residue within the site may be developed, and a second AQUA peptide incorporating the non-phosphorylated form of the residue developed. In this way, the two standards may be used to detect and quantify both the phosphorylated and non-phosphorylated forms of the site in a biological sample.

Peptide internal standards may also be generated by examining the primary amino acid sequence of a protein and determining the boundaries of peptides produced by protease cleavage. Alternatively, a protein may actually be digested with a protease and a particular peptide fragment produced can then sequenced. Suitable proteases include, but are not limited to, serine proteases (e.g. trypsin, hepsin), metallo proteases (e.g. PUMP1), chymotrypsin, cathepsin, pepsin, thermolysin, carboxypeptidases, etc.

A peptide sequence within a target protein is selected according to one or more criteria to optimize the use of the peptide as an internal standard. Preferably, the size of the peptide is selected to minimize the chances that the peptide sequence will be repeated elsewhere in other non-target proteins. Thus, a peptide is preferably at least about 6 amino acids. The size of the peptide is also optimized to maximize ionization frequency. Thus, peptides longer than about 20 amino acids are not preferred. The preferred ranged is about 7 to 15 amino acids. A peptide sequence is also selected that is not likely to be chemically reactive during mass spectrometry, thus sequences comprising cysteine, tryptophan, or methionine are avoided.

A peptide sequence that does not include a modified region of the target region may be selected so that the peptide internal standard can be used to determine the quantity of all forms of the protein. Alternatively, a peptide internal standard encompassing a modified amino acid may be desirable to detect and quantify only the modified form of the target protein. Peptide standards for both modified and unmodified regions can be used together, to determine the extent of a modification in a particular sample (i.e. to determine what fraction of the total amount of protein is represented by the modified form). For example, peptide standards for both the phosphorylated and unphosphorylated form of a protein known to be phosphorylated at a particular site can be used to quantify the amount of phosphorylated form in a sample.

The peptide is labeled using one or more labeled amino acids (i.e. the label is an actual part of the peptide) or less preferably, labels may be attached after synthesis according to standard methods. Preferably, the label is a mass-altering label selected based on the following considerations: The mass should be unique to shift fragments masses produced by MS analysis to regions of the spectrum with low background; the ion mass signature component is the portion of the labeling moiety that preferably exhibits a unique ion mass signature in MS analysis; the sum of the masses of the constituent atoms of the label is preferably uniquely different than the fragments of all the possible amino acids. As a result, the labeled amino acids and peptides are readily distinguished from unlabeled ones by the ion/mass pattern in the resulting mass spectrum. Preferably, the ion mass signature component imparts a mass to a protein fragment that does not match the residue mass for any of the 20 natural amino acids.

The label should be robust under the fragmentation conditions of MS and not undergo unfavorable fragmentation. Labeling chemistry should be efficient under a range of conditions, particularly denaturing conditions, and the labeled tag preferably remains soluble in the MS buffer system of choice. The label preferably does not suppress the ionization efficiency of the protein and is not chemically reactive. The label may contain a mixture of two or more isotopically distinct species to generate a unique mass spectrometric pattern at each labeled fragment position. Stable isotopes, such as $^2H$, $^{13}C$, $^{15}N$, $^{17}O$, $^{18}O$, or $^{34}S$, are among preferred labels. Pairs of peptide internal standards that incorporate a different isotope label may also be prepared. Preferred amino acid residues into which a heavy isotope label may be incorporated include leucine, proline, valine, and phenylalanine.

Peptide internal standards are characterized according to their mass-to-charge (m/z) ratio, and preferably, also according to their retention time on a chromatographic column (e.g. an HPLC column). Internal standards that co-elute with unlabeled peptides of identical sequence are selected as optimal internal standards. The internal standard is then analyzed by fragmenting the peptide by any suitable means, for example by collision-induced dissociation (CID) using, e.g., argon or helium as a collision gas. The fragments are then analyzed, for example by multi-stage mass spectrometry ($MS^n$) to obtain a fragment ion spectrum, to obtain a peptide fragmentation signature. Preferably, peptide fragments have significant differences in m/z ratios to enable peaks corresponding to each fragment to be well separated, and a signature is that is unique for the target peptide is obtained. If a suitable fragment signature is not obtained at the first stage, additional stages of MS are performed until a unique signature is obtained.

Fragment ions in the MS/MS and $MS^3$ spectra are typically highly specific for the peptide of interest, and, in conjunction with LC methods, allow a highly selective means of detecting and quantifying a target peptide/protein in a complex protein mixture, such as a cell lysate, containing many thousands or tens of thousands of proteins. Any biological sample potentially containing a target protein/peptide of interest may be assayed. Crude or partially purified/cell extracts are preferably employed. Generally, the sample has at least 0.01 mg of protein, typically a concentration of 0.1-10 mg/mL, and may be adjusted to a desired buffer concentration and pH.

A known amount of a labeled peptide internal standard, preferably about 10 femtomoles, corresponding to a target protein to be detected/quantified is then added to a biological sample, such as a cell lysate. The spiked sample is then digested with one or more protease(s) for a suitable time period to allow digestion. A separation is then performed (e.g. by HPLC, reverse-phase HPLC, capillary electrophoresis, ion exchange chromatography, etc.) to isolate the labeled internal standard and its corresponding target peptide from other peptides in the sample. Microcapillary LC is a preferred method.

Each isolated peptide is then examined by monitoring of a selected reaction in the MS. This involves using the prior knowledge gained by the characterization of the peptide internal standard and then requiring the MS to continuously monitor a specific ion in the MS/MS or $MS^n$ spectrum for both the peptide of interest and the internal standard. After elution, the area under the curve (AUC) for both peptide standard and target peptide peaks are calculated. The ratio of the two areas provides the absolute quantification that can be normalized for the number of cells used in the analysis and the protein's molecular weight, to provide the precise number of copies of the protein per cell. Further details of the AQUA methodology are described in Gygi et al., and Gerber et al. supra.

In accordance with the present invention, AQUA internal peptide standards (heavy-isotope labeled peptides) may now be produced, as described above, for any of the 168 novel EGFR-related signaling protein phosphorylation sites disclosed herein (see Table 1/FIG. 2). Peptide standards for a given phosphorylation site (e.g. the tyrosine 653 site in IRS-2—see Row 114 of Table 1) may be produced for both the phosphorylated and non-phosphorylated forms of the site (e.g. see IRS-2 site sequence in Column E, Row 114 of Table 1) and such standards employed in the AQUA methodology to detect and quantify both forms of such phosphorylation site in a biological sample.

AQUA peptides of the invention may comprise all, or part of, a phosphorylation site peptide sequence disclosed herein (see Column E of Table 1/FIG. 2). In a preferred embodiment, an AQUA peptide of the invention comprises a phosphorylation site sequence disclosed herein in Table 1/FIG. 2. For example, an AQUA peptide of the invention for detection/quantification of Fyn kinase when phosphorylated at tyrosine Y212 may comprise the sequence KLDNGGyYITTR (y=phosphotyrosine), which comprises phosphorylatable tyrosine 212 (see Row 118, Column E; SEQ ID NO: 117). Heavy-isotope labeled equivalents of an of the peptides enumerated in Table 1/FIG. 2. (both in phosphorylated and unphosphorylated form) can be readily synthesized and their unique MS and LC-SRM signature determined, so that the peptides are validated as AQUA peptides and ready for use in quantification experiments.

The phosphorylation site peptide sequences disclosed herein (see Column E of Table 1/FIG. 2) are particularly well suited for development of corresponding AQUA peptides, since the IAP method by which they were identified (see Part A above and Example 1) inherently confirmed that such peptides are in fact produced by enzymatic digestion (trypsinization) and are in fact suitably fractionated/ionized in MS/MS. Thus, heavy-isotope labeled equivalents of these peptides (both in phosphorylated and unphosphorylated form) can be readily synthesized and their unique MS and LC-SRM signature determined, so that the peptides are validated as AQUA peptides and ready for use in quantification experiments.

Accordingly, the invention provides heavy-isotope labeled peptides (AQUA peptides) for the detection and/or quantification of any of the EGFR-related phosphorylation sites disclosed in Table 1/FIG. 2 (see Column E) and/or their corresponding parent proteins/polypeptides (see Column A). A phosphopeptide sequence comprising any of the phosphorylation sequences listed in Table 1 may be considered a preferred AQUA peptide of the invention. For example, an AQUA peptide comprising the sequence LLGPGVNySGC-QITWAK (SEQ ID NO: 153) (where y may be either phosphotyrosine or tyrosine, and where V=labeled valine (e.g. $^{14}C$)) is provided for the quantification of phosphorylated (or non-phosphorylated) STAT3 (Tyr539) in a biological sample (see Row 154 of Table 1, tyrosine 539 being the phosphorylatable residue within the site). However, it will be appreciated that a larger AQUA peptide comprising a disclosed phosphorylation site sequence (and additional residues/downstream or upstream of it) may also be constructed. Similarly, a smaller AQUA peptide comprising less than all of the residues of a disclosed phosphorylation site sequence (but still comprising the phosphorylatable residue enumerated in Column D of Table 1/FIG. 2) may alternatively be constructed. Such larger or shorter AQUA peptides are within the scope of the present invention, and the selection and production of preferred AQUA peptides may be carried out as described above (see Gygi et al., Gerber et al. supra.).

Certain particularly preferred subsets of AQUA peptides provided by the invention are described above (corresponding to particular protein types/groups in Table 1, for example, Receptor Tyrosine Kinases or Transcription Factor proteins). Example 4 is provided to further illustrate the construction and use, by standard methods described above, of exemplary AQUA peptides provided by the invention. For example, the above-described AQUA peptides corresponding to the both the phosphorylated and non-phosphorylated forms of the disclosed STAT3 tyrosine 593 phosphorylation site (see Row 154 of Table 1/FIG. 2) may be used to quantify the amount of phosphorylated STAT3(Tyr593) in a biological sample, e.g. a tumor cell sample (or a sample before or after treatment with a test drug).

AQUA peptides of the invention may also be employed within a kit that comprises one or multiple AQUA peptide(s) provided herein (for the quantification of an EGFR-related signal transduction protein disclosed in Table 1), and, optionally, a second detecting reagent conjugated to a detectable group. For example, a kit may include AQUA peptides for both the phosphorylation and non-phosphorylated form of a phosphorylation site disclosed herein. The reagents may also include ancillary agents such as buffering agents and protein stabilizing agents, e.g., polysaccharides and the like. The kit may further include, where necessary, other members of the signal-producing system of which system the detectable group is a member (e.g., enzyme substrates), agents for reducing background interference in a test, control reagents, apparatus for conducting a test, and the like. The test kit may be packaged in any suitable manner, typically with all elements in a single container along with a sheet of printed instructions for carrying out the test.

AQUA peptides provided by the invention will be highly useful in the further study of signal transduction anomalies underlying cancer, including EGFR-mediated cancers, and in identifying diagnostic/bio-markers of these diseases, new potential drug targets, and/or in monitoring the effects of test compounds on EGFR-related signal transduction proteins and pathways.

D. Immunoassay Formats

Antibodies provided by the invention may be advantageously employed in a variety of standard immunological assays (the use of AQUA peptides provided by the invention is described separately above). Assays may be homogeneous assays or heterogeneous assays. In a homogeneous assay the immunological reaction usually involves a phosphorylation-site specific antibody of the invention), a labeled analyte, and the sample of interest. The signal arising from the label is modified, directly or indirectly, upon the binding of the antibody to the labeled analyte. Both the immunological reaction and detection of the extent thereof are carried out in a homogeneous solution. Immunochemical labels that may be employed include free radicals, radioisotopes, fluorescent dyes, enzymes, bacteriophages, coenzymes, and so forth.

In a heterogeneous assay approach, the reagents are usually the specimen, a phosphorylation-site specific antibody of the invention, and suitable means for producing a detectable signal. Similar specimens as described above may be used. The antibody is generally immobilized on a support, such as a bead, plate or slide, and contacted with the specimen suspected of containing the antigen in a liquid phase. The support is then separated from the liquid phase and either the support phase or the liquid phase is examined for a detectable signal employing means for producing such signal. The signal is related to the presence of the analyte in the specimen. Means for producing a detectable signal include the use of radioactive labels, fluorescent labels, enzyme labels, and so forth. For example, if the antigen to be detected contains a second binding site, an antibody which binds to that site can be conjugated to a detectable group and added to the liquid phase reaction solution before the separation step. The presence of the detectable group on the solid support indicates the presence of the antigen in the test sample. Examples of suitable immunoassays are the radioimmunoassay, immunofluorescence methods, enzyme-linked immunoassays, and the like.

Immunoassay formats and variations thereof that may be useful for carrying out the methods disclosed herein are well known in the art. See generally E. Maggio, Enzyme-Immunoassay, (1980) (CRC Press, Inc., Boca Raton, Fla.); see also, e.g., U.S. Pat. No. 4,727,022 (Skold et al., "Methods for Modulating Ligand-Receptor Interactions and their Application"); U.S. Pat. No. 4,659,678 (Forrest et al., "Immunoassay of Antigens"); U.S. Pat. No. 4,376,110 (David et al., "Immunometric Assays Using Monoclonal Antibodies"). Conditions suitable for the formation of reagent-antibody complexes are well described. See id. Monoclonal antibodies of the invention may be used in a "two-site" or "sandwich" assay, with a single cell line serving as a source for both the labeled monoclonal antibody and the bound monoclonal antibody. Such assays are described in U.S. Pat. No. 4,376,110. The concentration of detectable reagent should be sufficient such that the binding of a target EGFR-related signal transduction protein is detectable compared to background.

Phosphorylation site-specific antibodies disclosed herein may be conjugated to a solid support suitable for a diagnostic assay (e.g., beads, plates, slides or wells formed from materials such as latex or polystyrene) in accordance with known techniques, such as precipitation. Antibodies, or other target protein or target site-binding reagents, may likewise be conjugated to detectable groups such as radiolabels (e.g., $^{35}$S, $^{125}$I, $^{131}$I), enzyme labels (e.g., horseradish peroxidase, alkaline phosphatase), and fluorescent labels (e.g., fluorescein) in accordance with known techniques.

Antibodies of the invention may also be optimized for use in a flow cytometry assay to determine the activation/phosphorylation status of a target EGFR-related signal transduction protein in patients before, during, and after treatment with a drug targeted at inhibiting phosphorylation at such a protein at the phosphorylation site disclosed herein. For example, bone marrow cells or peripheral blood cells from patients may be analyzed by flow cytometry for target EGFR-related signal transduction protein phosphorylation, as well as for markers identifying various hematopoietic cell types. In this manner, activation status of the malignant cells may be specifically characterized. Flow cytometry may be carried out according to standard methods. See, e.g. Chow et al., *Cytometry (Communications in Clinical Cytometry)* 46: 72-78 (2001). Briefly and by way of example, the following protocol for cytometric analysis may be employed: fixation of the cells with 1% para-formaldehyde for 10 minutes at 37° C. followed by permeabilization in 90% methanol for 30 minutes on ice. Cells may then be stained with the primary antibody (a phospho-specific antibody of the invention), washed and labeled with a fluorescent-labeled secondary antibody. Alternatively, the cells may be stained with a fluorescent-labeled primary antibody. The cells would then be analyzed on a flow cytometer (e.g. a Beckman Coulter EPICS-XL) according to the specific protocols of the instrument used.

Such an analysis would identify the presence of activated EGFR-related signal transduction protein(s) in the malignant cells and reveal the drug response on the targeted protein.

Alternatively, antibodies of the invention may be employed in immunohistochemical (IHC) staining to detect differences in signal transduction or protein activity using normal and diseased tissues. IHC may be carried out according to well-known techniques. See, e.g., ANTIBODIES: A LABORATORY MANUAL, supra. Briefly, paraffin-embedded tissue (e.g. tumor tissue) is prepared for immunohistochemical staining by deparaffinizing tissue sections with xylene followed by ethanol; hydrating in water then PBS; unmasking antigen by heating slide in sodium citrate buffer; incubating sections in hydrogen peroxide; blocking in blocking solution; incubating, slide in primary antibody and secondary antibody; and finally detecting using ABC avidin/biotin method according to manufacturer's instructions.

Antibodies of the invention may be also be optimized for use in other clinically-suitable applications, for example bead-based multiplex-type assays, such as IGEN, Luminex™ and/or Bioplex™ assay formats, or otherwise optimized for antibody arrays formats, such as reversed-phase array applications (see, e.g. Paweletz et al., *Oncogene* 20(16): 1981-89 (2001)). Accordingly, in another embodiment, the invention provides a method for the multiplex detection of EGFR-related protein phosphorylation in a biological sample, the method comprising utilizing at two or more antibodies or AQUA peptides of the invention to detect the presence of two or more phosphorylated EGFR-related signaling proteins enumerated in Column A of Table 1/FIG. 2. In one preferred embodiment, two to five antibodies or AQUA peptides of the invention are employed in the method. In another preferred embodiment, six to ten antibodies or AQUA peptides of the invention are employed, while in another preferred embodiment eleven to twenty such reagents are employed.

Antibodies and/or AQUA peptides of the invention may also be employed within a kit that comprises at least one phosphorylation site-specific antibody or AQUA peptide of the invention (which binds to or detects an EGFR-related signal transduction protein disclosed in Table 1), and, optionally, a second antibody conjugated to a detectable group. In some embodies, the kit is suitable for multiplex assays and comprises two or more antibodies or AQUA peptides of the invention, and in some embodiments, comprises two to five, six to ten, or eleven to twenty reagents of the invention. The kit may also include ancillary agents such as buffering agents and protein stabilizing agents, e.g., polysaccharides and the like. The kit may further include, where necessary, other members of the signal-producing system of which system the detectable group is a member (e.g., enzyme substrates), agents for reducing background interference in a test, control reagents, apparatus for conducting a test, and the like. The test kit may be packaged in any suitable manner, typically with all elements in a single container along with a sheet of printed instructions for carrying out the test.

The following Examples are provided only to further illustrate the invention, and are not intended to limit its scope, except as provided in the claims appended hereto. The present invention encompasses modifications and variations of the methods taught herein which would be obvious to one of ordinary skill in the art.

Example 1

Isolation of Phosphotyrosine-Containing Peptides from Extracts of EGFR-Activated Tumor Cell Lines and Identification of Novel Phosphorylation Sites In order to discover previously unknown EGFR-related signal transduction protein phosphorylation sites, IAP isolation techniques were employed to identify phosphotyrosine-containing peptides in cell extracts from the following human carcinoma tumor cell lines, each of which has activated EGFR kinase: A431, HCT116, HPAC, MIAPACA2, PANC-1, A549, BxPC-3, DU145, HT-29, H460, and LNCaP. Increased expression of EGFR has been demonstrated in a variety of human cancers, including breast, colon, pancreatic, ovarian, lung, esophogeal, and neural. See, e.g., Yeatman, supra. Thus, the cancer cell lines expressing elevated levels of EGFR and stimulated with EGF were chosen to mimic signaling pathway activity in cancers involving activated EGFR.

Tryptic phosphotyrosine peptides were purified and analyzed from extracts of the each of the eleven cell lines mentioned above as follows. Cells were cultured in DMEM medium or RPMI 1640 medium supplemented with 10% fetal bovine serum and penicillin/streptomycin. Cells at about 80% confluency were starved in medium without serum for 16 hours and stimulated with 100 ng/ml EGF for 5 minutes. After complete aspiration of medium from the plates, cells were scraped off the plate in 10 ml lysis buffer per $2 \times 10^8$ cells (20 mM HEPES pH 8.0, 9 M urea, 1 mM sodium vanadate, supplemented with 2.5 mM sodium pyrophosphate, 1 mM β-glycerol-phosphate) and sonicated.

Sonicated cell lysates were cleared by centrifugation at $20,000 \times g$, and proteins were reduced with DTT at a final concentration of 4.1 mM and alkylated with iodoacetamide at 8.3 mM. For digestion with trypsin, protein extracts were diluted in 20 mM HEPES pH 8.0 to a final concentration of 2 M urea and soluble TLCK-trypsin (Worthington) was added at 10-20 µg/mL. Digestion was performed for 1-2 days at room temperature.

Trifluoroacetic acid (TFA) was added to protein digests to a final concentration of 1%, precipitate was removed by centrifugation, and digests were loaded onto Sep-Pak $C_{18}$ columns (Waters) equilibrated with 0.1% TFA. A column volume of 0.7-1.0 ml was used per $2 \times 10^8$ cells. Columns were washed with 15 volumes of 0.1% TFA, followed by 4 volumes of 5% acetonitrile (MeCN) in 0.1% TFA. Peptide fraction I was obtained by eluting columns with 2 volumes each of 8, 12, and 15% MeCN in 0.1% TFA and combining the eluates. Fractions II and III were a combination of eluates after eluting columns with 18, 22, 25% MeCN in 0.1% TFA and with 30, 35, 40% MeCN in 0.1% TFA, respectively. All peptide fractions were lyophilized.

Peptides from each fraction corresponding to $2 \times 10^8$ cells were dissolved in 1 ml of IAP buffer (20 mM Tris/HCl or 50 mM MOPS pH 7.2, 10 mM sodium phosphate, 50 mM NaCl) and insoluble matter (mainly in peptide fractions III) was removed by centrifugation. IAP was performed on each peptide fraction separately. The phosphotyrosine monoclonal antibody P-Tyr-100 (Cell Signaling Technology, Inc., catalog number 9411) was coupled at 4 mg/ml beads to protein G agarose (Roche). Immobilized antibody (15 µl, 60 µg) was added as 1:1 slurry in IAP buffer to 1 ml of each peptide fraction, and the mixture was incubated overnight at 4° C. with gentle rotation. The immobilized antibody beads were washed three times with 1 ml IAP buffer and twice with 1 ml water, all at 4° C. Peptides were eluted from beads by incubation with 75 µl of 0.1% TFA at room temperature for 10 min.

Alternatively, one single peptide fraction was obtained from Sep-Pak C18 columns by elution with 2 volumes each of 10%, 15%, 20%, 25%, 30%, 35% and 40% acetonitrile in 0.1% TFA and combination of all eluates. IAP on this peptide fraction was performed as follows: After lyophilization, peptide was dissolved in 1.4 ml IAP buffer (MOPS pH 7.2, mM sodium phosphate, 50 mM NaCl) and insoluble matter was removed by centrifugation. Immobilized antibody (40 µl, 160 µg) was added as 1:1 slurry in IAP buffer, and the mixture was incubated overnight at 4° C. with gentle shaking. The immobilized antibody beads were washed three times with 1 ml IAP buffer and twice with 1 ml water, all at 4° C. Peptides were eluted from beads by incubation with 55 µl of 0.15% TFA at room temperature for 10 min (eluate 1), followed by a wash of the beads (eluate 2) with 45 µl of 0.15% TFA. Both eluates were combined.

Analysis by LC-MS/MS Mass Spectrometry.

40 µl of IAP eluate were purified by 0.2 µl StageTips or ZipTips. Peptides were eluted from the microcolumns with 1 µl of 40% MeCN, 0.1% TFA (fractions I and II) or 1 µl of 60% MeCN, 0.1% TFA (fraction III) into 7.6 µl of 0.4% acetic acid/0.005% heptafluorobutyric acid. This sample was loaded onto a 10 cm×75 µm PicoFrit capillary column (New Objective) packed with Magic C18 AQ reversed-phase resin (Michrom Bioresources) using a Famos autosampler with an inert sample injection valve (Dionex). The column was then developed with a 45-min linear gradient of acetonitrile delivered at 200 nl/min (Ultimate, Dionex), and tandem mass spectra were collected in a data-dependent manner with an LCQ Deca XP Plus ion trap mass spectrometer essentially as described by Gygi et al., supra.

Database Analysis & Assignments.

MS/MS spectra were evaluated using TurboSequest in the Sequest Browser package (v. 27, rev. 12) supplied as part of BioWorks 3.0 (ThermoFinnigan). Individual MS/MS spectra were extracted from the raw data file using the Sequest Browser program CreateDta, with the following settings: bottom MW, 700; top MW, 4,500; minimum number of ions, 20; minimum TIC, $4 \times 10^5$; and precursor charge state, unspecified. Spectra were extracted from the beginning of the raw data file before sample injection to the end of the eluting gradient. The IonQuest and VuDta programs were not used to further select MS/MS spectra for Sequest analysis. MS/MS spectra were evaluated with the following TurboSequest parameters: peptide mass tolerance, 2.5; fragment ion tolerance, 0.0; maximum number of differential amino acids per modification, 4; mass type parent, average; mass type fragment, average; maximum number of internal cleavage sites, 10; neutral losses of water and ammonia from b and y ions were considered in the correlation analysis. Proteolytic enzyme was specified except for spectra collected from elastase digests.

Searches were performed against the NCBI human protein database (for all other studies) (released on Apr. 29, 2003 and containing 37,490 protein sequences). Cysteine carboxamidomethylation was specified as a static modification, and phosphorylation was allowed as a variable modification on serine, threonine, and tyrosine residues or on tyrosine residues alone. It was determined that restricting phosphorylation to tyrosine residues had little effect on the number of phosphorylation sites assigned.

In proteomics research, it is desirable to validate protein identifications based solely on the observation of a single peptide in one experimental result, in order to indicate that the protein is, in fact, present in a sample. This has led to the development of statistical methods for validating peptide assignments, which are not yet universally accepted, and guidelines for the publication of protein and peptide identification results (see Carr et al., *Mol. Cell. Proteomics* 3: 531-533 (2004)), which were followed in this Example. However, because the immunoaffinity strategy separates phosphorylated peptides from unphosphorylated peptides, observing just one phosphopeptide from a protein is a common result, since many phosphorylated proteins have only one tyrosine-phosphorylated site. For this reason, it is appropriate to use additional criteria to validate phosphopeptide assignments. Assignments are likely to be correct if any of these additional criteria are met: (i) the same sequence is assigned to co-eluting ions with different charge states, since the MS/MS spectrum changes markedly with charge state; (ii) the site is found in more than one peptide sequence context due to sequence overlaps from incomplete proteolysis or use of proteases other than trypsin; (iii) the site is found in more than one peptide sequence context due to homologous but not identical protein isoforms; (iv) the site is found in more than one peptide sequence context due to homologous but not identical proteins among species; and (v) sites validated by MS/MS analysis of synthetic phosphopeptides corresponding to assigned sequences, since the ion trap mass spectrometer produces highly reproducible MS/MS spectra. The last criterion is routinely employed to confirm novel site assignments of particular interest.

All spectra and all sequence assignments made by Sequest were imported into a relational database. Assigned sequences were accepted or rejected following a conservative, two-step process. In the first step, a subset of high-scoring sequence assignments was selected by filtering for XCorr values of at least 1.5 for a charge state of +1, 2.2 for +2, and 3.3 for +3, allowing a maximum RSp value of 10. Assignments in this subset were rejected if any of the following criteria were satisfied: (i) the spectrum contained at least one major peak (at least 10% as intense as the most intense ion in the spectrum) that could not be mapped to the assigned sequence as an a, b, or y ion, as an ion arising from neutral-loss of water or ammonia from a b or y ion, or as a multiply protonated ion; (ii) the spectrum did not contain an series of b or y ions equivalent to at least six uninterrupted residues; or (iii) the sequence was not observed at least five times in all the studies we have conducted (except for overlapping sequences due to incomplete proteolysis or use of proteases other than trypsin). In the second step, assignments with below-threshold scores were accepted if the low-scoring spectrum showed a high degree of similarity to a high-scoring spectrum collected in another study, which simulates a true reference library-searching strategy. All spectra supporting the final list of 168 assigned sequences enumerated in Table 1/FIG. 2 herein were reviewed by at least three people to establish their credibility.

Example 2

Production of Phospho-specific Polyclonal Antibodies for the Detection of EGFR-Related Signaling Protein Phosphorylation Polyclonal antibodies that specifically bind an EGFR-related signal transduction protein only when phosphorylated at the respective phosphorylation site disclosed herein (see Table 1) are produced according to standard methods by first constructing a synthetic peptide antigen comprising the phosphorylation site sequence and then immunizing an animal to raise antibodies against the antigen, as further described below. Production of exemplary polyclonal antibodies is provided below.

A. HER2 (tyrosine 923).

A 15 amino acid phospho-peptide antigen, MTFGAKPy*DGIPAR (where y*=phosphotyrosine) that corresponds to the sequence encompassing the tyrosine 923 phosphorylation site in human HER2 receptor kinase (see Row 124 of Table 1; SEQ ID NO: 123), plus cysteine on the C-terminal for coupling, is constructed according to standard synthesis techniques using, e.g., a Rainin/Protein Technologies, Inc., Symphony peptide synthesizer. See ANTIBODIES: A LABORATORY MANUAL, supra.; Merrifield, supra. This peptide is then coupled to KLH and used to immunize animals to produce (and subsequently screen) phospho-specific HER2 (tyr923) polyclonal antibodies as described in Immunization/Screening below.

B. BRSK1 (Tyrosine 121).

A 13 amino acid phospho-peptide antigen, VYENKKy*LYLVLE (where y*=phosphotyrosine) that corresponds to the sequence encompassing the tyrosine 121 phosphorylation site in human BRSK1 kinase (see Row 112 of Table 1 (SEQ ID NO: 111)), plus cysteine on the C-terminal for coupling, is constructed according to standard synthesis techniques using, e.g., a Rainin/Protein Technologies, Inc., Symphony peptide synthesizer. See ANTIBODIES: A LABORATORY MANUAL, supra.; Merrifield, supra. This peptide is then coupled to KLH and used to immunize animals to produce (and subsequently screen) phospho-specific BRSK1(tyr121) polyclonal antibodies as described in Immunization/Screening below.

C. IRS-2 (Tyrosine 823).

A 15 amino acid phospho-peptide antigen, CGGDSDQy*VLMSSPV (where y*=phosphotyrosine) that corresponds to the sequence encompassing the tyrosine 823 phosphorylation site in human IRS-2 protein (see Row 16 of Table 1 (SEQ ID NO: 15), plus cysteine on the C-terminal for coupling, is constructed according to standard synthesis techniques using, e.g., a Rainin/Protein Technologies, Inc., Symphony peptide synthesizer. See ANTIBODIES: A LABORATORY MANUAL, supra.; Merrifield, supra. This peptide is then coupled to KLH and used to immunize animals to produce (and subsequently screen) phospho-specific IRS-2 (tyr823) antibodies as described in Immunization/Screening below.

Immunization/Screening.

A synthetic phospho-peptide antigen as described in A-C above is coupled to KLH, and rabbits are injected intradermally (ID) on the back with antigen in complete Freunds adjuvant (500 μg antigen per rabbit). The rabbits are boosted with same antigen in incomplete Freund adjuvant (250 μg antigen per rabbit) every three weeks. After the fifth boost, bleeds are collected. The sera are purified by Protein A-affinity chromatography by standard methods (see ANTIBODIES: A LABORATORY MANUAL, Cold Spring Harbor, supra.). The eluted immunoglobulins are further loaded onto a non-phosphorylated synthetic peptide antigen-resin Knotes column to pull out antibodies that bind the non-phosphorylated form of the phosphorylation site. The flow through fraction is collected and applied onto a phospho-synthetic peptide antigen-resin column to isolate antibodies that bind the phosphorylated form of the site. After washing the column extensively, the bound antibodies (i.e. antibodies that bind a phosphorylated peptide described in A-C above, but do not bind the non-phosphorylated form of the peptide, are eluted and kept in antibody storage buffer.

The isolated antibody is then tested for phospho-specificity using Western blot assay using an appropriate cell line the expresses (or overexpresses) target phospho-protein (i.e. phosphorylated HER2, BRSK1, or IRS-2, for example, HT-29, A431 and HCT-116 cells, respectively. Cells are cultured in DMEM supplemented with 10% FCS. Before stimulation, the cells are starved in serum-free DMEM medium for 4 hours. The cells are then stimulated ligand (e.g. EGF 100 ng/ml) for 5 minutes. Cells are collected, washed with PBS and directly lysed in cell lysis buffer. The protein concentration of cell lysates are then measured. The loading buffer is added into cell lysate and the mixture is boiled at 100° C. for 5 minutes. 20 μl (10 μg protein) of sample is then added onto 7.5% SDS-PAGE gel.

A standard Western blot may be performed according to the Immunoblotting Protocol set out in the CELL SIGNALING TECHNOLOGY, INC. 2003-04 Catalogue, p. 390. The isolated phospho-specific antibody is used at dilution 1:1000. Phosphorylation-site specificity of the antibody will be shown by binding of only the phosphorylated form of the target protein. Isolated phospho-specific polyclonal antibody does not recognize the target protein when not phosphorylated at the appropriate phosphorylation site in the non-stimulated cells (e.g. IRS-2 is not bound when not phosphorylated at tyrosine 823).

In order to confirm the specificity of the isolated antibody, different cell lysates containing various phosphorylated signal transduction proteins other than the target protein are prepared. The Western blot assay is preformed again using these cell lysates. The phospho-specific polyclonal antibody isolated as described above is used (1:1000 dilution) to test reactivity with the different phosphorylated non-target proteins on Western blot membrane. The phospho-specific antibody does not significantly cross-react with other phosphorylated signal transduction proteins, although occasionally slight binding with a highly homologous phosphorylation-site on another protein may be observed. In such case the antibody may be further purified using affinity chromatography, or the specific immunoreactivity cloned by rabbit hybridoma technology.

Example 3

Production of Phospho-Specific Monoclonal Antibodies for the Detection of EGFR-Related Signaling Protein Phosphorylation Monoclonal antibodies that specifically bind a EGFR-related signal transduction protein only when phosphorylated at the respective phosphorylation site disclosed herein (see Table 1) are produced according to standard methods by first constructing a synthetic peptide antigen comprising the phosphorylation site sequence and then immunizing an animal to raise antibodies against the antigen, and harvesting spleen cells from such animals to produce fusion hybridomas, as further described below. Production of exemplary monoclonal antibodies is provided below.

A. EphB4 (Tyrosine 574).

A 13 amino acid phospho-peptide antigen, NGREAEy*SDKHGQ (where y*=phosphotyrosine) that corresponds to the sequence encompassing the tyrosine 574 phosphorylation site in human EphB4 kinase (see Row 137 of Table 1 (SEQ ID NO: 136)), plus cysteine on the C-terminal for coupling, is constructed according to standard synthesis techniques using, e.g., a Rainin/Protein Technologies, Inc., Symphony peptide synthesizer. See ANTIBODIES: A LABORATORY MANUAL, supra.; Merrifield, supra. This peptide is then coupled to KLH and used to immunize animals and harvest spleen cells for generation (and subsequent screening) of phospho-specific monoclonal EphB4(tyr574) antibodies as described in Immunization/Fusion/Screening below.

B. MINK (Tyrosine 906).

A 15 amino acid phospho-peptide antigen, LHADSNGy*TNLPDVV (where y*=phosphotyrosine) that corresponds to the sequence encompassing the tyrosine 906 phosphorylation site in human MINK kinase (see Row 116 of Table 1 (SEQ ID NO: 115)), plus cysteine on the C-terminal for coupling, is constructed according to standard synthesis techniques using, e.g., a Rainin/Protein Technologies, Inc., Symphony peptide synthesizer. See ANTIBODIES: A LABORATORY MANUAL, supra.; Merrifield, supra. This peptide is then coupled to KLH and used to immunize animals and harvest spleen cells for generation (and subsequent screening) of phospho-specific monoclonal MINK(tyr906) antibodies as described in Immunization/Fusion/Screening below.

C. PTP-Kappa (Tyrosine 858).

A 14 amino acid phospho-peptide antigen, CEGTESPy*YGNDSD (where y*=phosphotyrosine) that corresponds to the sequence encompassing the tyrosine 858 phosphorylation site in human PTP-kappa phosphatase (see Row 121 of Table 1 (SEQ ID NO: 120)), plus cysteine on the C-terminal for coupling, is constructed according to standard synthesis techniques using, e.g., a Rainin/Protein Technologies, Inc., Symphony peptide synthesizer. See ANTIBODIES: A LABORATORY MANUAL, supra.; Merrifield, supra. This peptide is then coupled to KLH and used to immunize animals and harvest spleen cells for generation (and subsequent screening) of phospho-specific monoclonal PTP-kappa (tyr858) antibodies as described in Immunization/Fusion/Screening below.

Immunization/Fusion/Screening.

A synthetic phospho-peptide antigen as described in A-C above is coupled to KLH, and BALB/C mice are injected intradermally (ID) on the back with antigen in complete Freunds adjuvant (e.g. 50 μg antigen per mouse). The mice are boosted with same antigen in incomplete Freund adjuvant (e.g. 25 μg antigen per mouse) every three weeks. After the fifth boost, the animals are sacrificed and spleens are harvested.

Harvested spleen cells are fused to SP2/0 mouse myeloma fusion partner cells according to the standard protocol of Kohler and Milstein (1975). Colonies originating from the fusion are screened by ELISA for reactivity to the phospho-peptide and non-phospho-peptide forms of the antigen and by Western blot analysis (as described in Example 1 above). Colonies found to be positive by ELISA to the phospho-peptide while negative to the non-phospho-peptide are further characterized by Western blot analysis. Colonies found to be positive by Western blot analysis are subcloned by limited dilution. Mouse ascites are produced from a single clone obtained from subcloning, and tested for phospho-specificity (against the EphB4, MINK, or PTP-delta phospho-peptide antigen, as the case may be) on ELISA. Clones identified as positive on Western blot analysis using cell culture supernatant as having phospho-specificity, as indicated by a strong band in the induced lane and a weak band in the uninduced lane of the blot, are isolated and subcloned as clones producing monoclonal antibodies with the desired specificity.

Ascites fluid from isolated clones may be further tested by Western blot analysis. The ascites fluid should produce similar results on Western blot analysis as observed previously with the cell culture supernatant, indicating phospho-specificity against the phosphorylated target (e.g. MINK phosphorylated at tyrosine 906).

Example 4

Production and Use of AQUA Peptides for the Quantification of EGFR-Related Signaling Protein Phosphorylation Heavy-isotope labeled peptides (AQUA peptides (internal standards)) for the detection and quantification of an EGFR-related signal transduction protein only when phosphorylated at the respective phosphorylation site disclosed herein (see Table 1) are produced according to the standard AQUA methodology (see Gygi et al., Gerber et al., supra.) methods by first constructing a synthetic peptide standard corresponding to the phosphorylation site sequence and incorporating a heavy-isotope label. Subsequently, the $MS^n$ and LC-SRM signature of the peptide standard is validated, and the AQUA peptide is used to quantify native peptide in a biological sample, such as a digested cell extract. Production and use of exemplary AQUA peptides is provided below.

A. Ron (Tyrosine 1238).

An AQUA peptide comprising the sequence, DILDREy*YSVQQHR (y*=phosphotyrosine; sequence incorporating $^{14}C/^{15}N$-labeled leucine (indicated by bold L), which corresponds to the tyrosine 1238 phosphorylation site in human Ron kinase (see Row 142 in Table 1 (SEQ ID NO: 141)), is constructed according to standard synthesis techniques using, e.g., a Rainin/Protein Technologies, Inc., Symphony peptide synthesizer (see Merrifield, supra.) as further described below in Synthesis & MS/MS Signature. The Ron (tyr1238) AQUA peptide is then spiked into a biological sample to quantify the amount of phosphorylated Ron (tyr1238) in the sample, as further described below in Analysis & Quantification.

B. PI3K p85-Beta (Tyrosine 467).

An AQUA peptide comprising the sequence, SREYDQLYEEy*TR (y*=phosphotyrosine; sequence incorporating $^{14}C/^{15}N$-labeled leucine (indicated by bold L), which corresponds to the tyrosine 467 phosphorylation site in human PI3K p85-beta kinase (see Row 100 in Table 1 (SEQ ID NO: 99)), is constructed according to standard synthesis techniques using, e.g., a Rainin/Protein Technologies, Inc., Symphony peptide synthesizer (see Merrifield, supra.) as further described below in Synthesis & MS/MS Signature. The PI3K P85-beta(tyr467) AQUA peptide is then spiked into a biological sample to quantify the amount of phosphorylated PI3K P85-beta(tyr467) in the sample, as further described below in Analysis & Quantification.

C. Annexin A4 (Tyrosine 164)

An AQUA peptide comprising the sequence, VLVSLSAGGRDEGNy*LDDALVR (y*=phosphotyrosine; sequence incorporating $^{14}C/^{15}N$-labeled leucine (indicated by bold L), which corresponds to the tyrosine 164 phosphorylation site in human Annexin A4 protein (see Row 61 in Table 1 (SEQ ID NO: 60)), is constructed according to standard synthesis techniques using, e.g., a Rainin/Protein Technologies, Inc., Symphony peptide synthesizer (see Merrifield, supra.) as further described below in Synthesis & MS/MS Signature. The Annexin A4(tyr164) AQUA peptide is then spiked into a biological sample to quantify the amount of phosphorylated Annexin A4(tyr164) in the sample, as further described below in Analysis & Quantification.

D. Talin 1 (Tyrosine 26).

An AQUA peptide comprising the sequence, TMQFEPSTMVy*DACR (y*=phosphotyrosine; sequence incorporating $^{14}C/^{15}N$-labeled valine (indicated by bold V), which corresponds to THE tyrosine 26 phosphorylation site in human Talin 1 protein (see Row 78 in Table 1 (SEQ ID NO: 77)), is constructed according to standard synthesis techniques using, e.g., a Rainin/Protein Technologies, Inc., Symphony peptide synthesizer (see Merrifield, supra.) as further described below in Synthesis & MS/MS Signature. The Talin 1 (tyr26) AQUA peptide is then spiked into a biological sample to quantify the amount of phosphorylated Talin 1(tyr26) in the sample, as further described below in Analysis & Quantification.

Synthesis & MS/MS Spectra.

Fluorenylmethoxycarbonyl (Fmoc)-derivatized amino acid monomers may be obtained from AnaSpec (San Jose, Calif.). Fmoc-derivatized stable-isotope monomers containing one $^{15}N$ and five to nine $^{13}C$ atoms may be obtained from Cambridge Isotope Laboratories (Andover, Mass.). Pre-loaded Wang resins may be obtained from Applied Biosystems. Synthesis scales may vary from 5 to 25 μmol. Amino acids are activated in situ with 1-H-benzotriazolium, 1-bis (dimethylamino) methylene]-hexafluorophosphate(1-),3-oxide:1-hydroxybenzotriazole hydrate and coupled at a 5-fold molar excess over peptide. Each coupling cycle is followed by capping with acetic anhydride to avoid accumulation of one-residue deletion peptide byproducts. After synthesis peptide-resins are treated with a standard scavenger-containing trifluoroacetic acid (TFA)-water cleavage solution, and the peptides are precipitated by addition to cold ether. Peptides (i.e. a desired AQUA peptide described in A-D above) are purified by reversed-phase C18 HPLC using standard TFA/acetonitrile gradients and characterized by matrix-assisted laser desorption ionization-time of flight (Biflex III, Bruker Daltonics, Billerica, Mass.) and ion-trap (ThermoFinnigan, LCQ DecaXP) MS.

MS/MS spectra for each AQUA peptide should exhibit a strong y-type ion peak as the most intense fragment ion that is suitable for use in an SRM monitoring/analysis. Reverse-phase microcapillary columns (0.1 Å~150-220 mm) are prepared according to standard methods. An Agilent 1100 liquid chromatograph may be used to develop and deliver a solvent gradient [0.4% acetic acid/0.005% heptafluorobutyric acid (HFBA)/7% methanol and 0.4% acetic acid/0.005% HFBA/65% methanol/35% acetonitrile] to the microcapillary column by means of a flow splitter. Samples are then directly loaded onto the microcapillary column by using a FAMOS inert capillary autosampler (LC Packings, San Francisco) after the flow split. Peptides are reconstituted in 6% acetic acid/0.01% TFA before injection.

Analysis & Quantification.

Target protein (e.g. a phosphorylated protein of A-D above) in a biological sample is quantified using a validated AQUA peptide (as described above). The IAP method is then applied to the complex mixture of peptides derived from proteolytic cleavage of crude cell extracts to which the AQUA peptides have been spiked in.

LC-SRM of the entire sample is then carried out. MS/MS may be performed by using a ThermoFinnigan (San Jose, Calif.) mass spectrometer (LCQ DecaXP ion trap or TSQ Quantum triple quadrupole). On the DecaXP, parent ions are isolated at 1.6 m/z width, the ion injection time being limited to 150 ms per microscan, with two microscans per peptide averaged, and with an AGC setting of $1\times10^8$; on the Quantum, Q1 is kept at 0.4 and Q3 at 0.8 m/z with a scan time of 200 ms per peptide. On both instruments, analyte and internal standard are analyzed in alternation within a previously known reverse-phase retention window; well-resolved pairs of internal standard and analyte are analyzed in separate retention segments to improve duty cycle. Data are processed by integrating the appropriate peaks in an extracted ion chromatogram (60.15 m/z from the fragment monitored) for the native and internal standard, followed by calculation of the ratio of peak areas multiplied by the absolute amount of internal standard (e.g., 500 fmol).

What is claimed is:

1. An isolated phosphorylation site-specific antibody specifically binds an EphA2 protein only when phosphorylated at the tyrosine at position 575, located within the phosphorylatable peptide sequence listed in SEQ ID NO: 126, wherein said antibody does not bind said protein when not phosphorylated at said tyrosine.

2. An isolated phosphorylation site-specific antibody specifically binds an EphA2 protein only when phosphorylated at the tyrosine at position 588, located within the phosphorylatable peptide sequence listed in SEQ ID NO: 127, wherein said antibody does not bind said protein when not phosphorylated at said tyrosine.

3. An isolated phosphorylation site-specific antibody specifically binds an EphA2 protein only when phosphorylated at the tyrosine at position 594, located within the phosphorylatable peptide sequence listed in SEQ ID NO: 128, wherein said antibody does not bind said protein when not phosphorylated at said tyrosine.

4. An isolated phosphorylation site-specific antibody specifically binds an EGFR protein only when phosphorylated at the tyrosine at position 998, located within the phosphorylatable peptide sequence listed in SEQ ID NO: 122, wherein said antibody does not bind said protein when not phosphorylated at said tyrosine.

5. The antibody of claim 1, 2, 3 or 4 wherein said antibody is selected from the group consisting of a monoclonal antibody and a polyclonal antibody.

6. The antibody of claim 1, 2, 3 or 4 wherein said antibody is conjugated to a fluorescent dye.

* * * * *

SEQUENCE LISTING

```
<160> NUMBER OF SEQ ID NOS: 168

<210> SEQ ID NO 1
<211> LENGTH: 25
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: PHOSPHORYLATION; tyrosine at position 4 is
      phosphorylated

<400> SEQUENCE: 1

Asp Leu Gln Tyr Ile Thr Val Ser Lys Glu Glu Leu Ser Ser Gly Asp
1               5                   10                  15

Ser Leu Ser Pro Asp Pro Trp Lys Arg
            20                  25

<210> SEQ ID NO 2
<211> LENGTH: 29
<212> TYPE: PRT
<213> ORGANISM: Homo sapiens
<220> FEATURE:
<221> NAME/KEY: MOD_RES
<222> LOCATION: (23)..(23)
<223> OTHER INFORMATION: PHOSPHORYLATION; tyrosine at position 23 is
      phosphorylated

<400> SEQUENCE: 2

Thr Val Gln Pro Val Ala Met Gly Pro Asp Gly Leu Pro Val Asp Ala
1               5                   10                  15

Ser Ser Val Ser Asn Asn Tyr Ile Gln Thr Leu Gly Arg
            20                  25

<210> SEQ ID NO 3
<211> LENGTH: 11
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: PHOSPHORYLATION; tyrosine at position 9 is
      phosphorylated

<400> SEQUENCE: 3

Asn Phe His Tyr Pro Pro Asp Gly Tyr Ser Arg
1               5                   10

<210> SEQ ID NO 4
<211> LENGTH: 9
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 4

Tyr Arg Pro Ser Met Glu Gly Tyr Arg
```

<210> SEQ ID NO 5
<211> LENGTH: 25
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: PHOSPHORYLATION; tyrosine at position 2 is
    phosphorylated

<400> SEQUENCE: 5

Ser Tyr Glu Asp Met Ile Gly Glu Glu Val Pro Ser Asp Gln Tyr Tyr
1               5                   10                  15

Trp Ala Pro Leu Ala Gln His Glu Arg
            20                  25

<210> SEQ ID NO 6
<211> LENGTH: 25
<212> TYPE: PRT
<213> ORGANISM: Homo sapiens
<220> FEATURE:
<221> NAME/KEY: MOD_RES
<222> LOCATION: (16)..(16)
<223> OTHER INFORMATION: PHOSPHORYLATION; tyrosine at position 16 is
    phosphorylated

<400> SEQUENCE: 6

Ser Tyr Glu Asp Met Ile Gly Glu Glu Val Pro Ser Asp Gln Tyr Tyr
1               5                   10                  15

Trp Ala Pro Leu Ala Gln His Glu Arg
            20                  25

<210> SEQ ID NO 7
<211> LENGTH: 16
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: PHOSPHORYLATION; tysosine at position 10 is
    phosphorylated

<400> SEQUENCE: 7

Thr Gln Asp Gln Ile Ser Asn Ile Lys Tyr His Glu Glu Phe Glu Lys
1               5                   10                  15

<210> SEQ ID NO 8
<211> LENGTH: 14
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: PHOSPHORYLATION; tyrosine at position 1 is
    phosphorylated

<400> SEQUENCE: 8

Tyr Val Asp Ser Glu Gly His Leu Tyr Thr Val Pro Ile Arg
1               5                   10

<210> SEQ ID NO 9
<211> LENGTH: 27
<212> TYPE: PRT
<213> ORGANISM: Homo sapiens
<220> FEATURE:
<221> NAME/KEY: MOD_RES

```
<222> LOCATION: (11)..(11)
<223> OTHER INFORMATION: PHOSPHORYLATION; tyrosine at position 11 is
      phosphorylated

<400> SEQUENCE: 9

Gln Gly Ala Glu Gly Ala Pro Ser Pro Asn Tyr Asp Asp Asp Asp
1               5                   10                  15

Glu Arg Ala Asp Asp Thr Leu Phe Met Met Lys
            20                  25

<210> SEQ ID NO 10
<211> LENGTH: 16
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: PHOSPHORYLATION; tyrosine at position 10 is
      phosphorylated

<400> SEQUENCE: 10

Arg Asp Asn Glu Val Asp Gly Gln Asp Tyr His Phe Val Val Ser Arg
1               5                   10                  15

<210> SEQ ID NO 11
<211> LENGTH: 37
<212> TYPE: PRT
<213> ORGANISM: Homo sapiens
<220> FEATURE:
<221> NAME/KEY: MOD_RES
<222> LOCATION: (17)..(17)
<223> OTHER INFORMATION: PHOSPHORYLATION; tyrosine at position 17 is
      phosphorylated

<400> SEQUENCE: 11

Ala Glu Pro Met Pro Ser Ala Ser Ala Pro Pro Ala Ser Ser Leu
1               5                   10                  15

Tyr Ser Ser Pro Val Asn Ser Ser Ala Pro Leu Ala Glu Asp Ile Asp
            20                  25                  30

Pro Glu Leu Ala Arg
        35

<210> SEQ ID NO 12
<211> LENGTH: 26
<212> TYPE: PRT
<213> ORGANISM: Homo sapiens
<220> FEATURE:
<221> NAME/KEY: MOD_RES
<222> LOCATION: (16)..(16)
<223> OTHER INFORMATION: PHOSPHORYLATION; tyrosine at position 16 is
      phosphorylated

<400> SEQUENCE: 12

Gly Ser Gln Asp His Ser Gly Asp Pro Thr Ser Gly Asp Arg Gly Tyr
1               5                   10                  15

Thr Asp Pro Cys Val Ala Thr Ser Leu Lys
            20                  25

<210> SEQ ID NO 13
<211> LENGTH: 30
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: PHOSPHORYLATION; tyrosine at position 12 is
      phosphorylated
```

-continued

```
<400> SEQUENCE: 13

Ser Ser Ser Ser Asn Leu Gly Ala Asp Asp Gly Tyr Met Pro Met Thr
1               5                   10                  15

Pro Gly Ala Ala Leu Ala Gly Ser Gly Ser Gly Ser Cys Arg
            20                  25                  30

<210> SEQ ID NO 14
<211> LENGTH: 16
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: PHOSPHORYLATION; tyrosine at position 4 is
      phosphorylated

<400> SEQUENCE: 14

Ser Asp Asp Tyr Met Pro Met Ser Pro Ala Ser Val Ser Ala Pro Lys
1               5                   10                  15

<210> SEQ ID NO 15
<211> LENGTH: 24
<212> TYPE: PRT
<213> ORGANISM: Homo sapiens
<220> FEATURE:
<221> NAME/KEY: MOD_RES
<222> LOCATION: (15)..(15)
<223> OTHER INFORMATION: PHOSPHORYLATION; tyrosine at position 15 is
      phosphorylated

<400> SEQUENCE: 15

Ser Tyr Lys Ala Pro Tyr Thr Cys Gly Gly Asp Ser Asp Gln Tyr Val
1               5                   10                  15

Leu Met Ser Ser Pro Val Gly Arg
            20

<210> SEQ ID NO 16
<211> LENGTH: 30
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION; tyrosine at position 7 is
      phosphorylated

<400> SEQUENCE: 16

Lys Gly Lys Asp Gly Glu Tyr Glu Glu Leu Leu Asn Ser Ser Ser Ile
1               5                   10                  15

Ser Ser Leu Leu Asp Ala Gln Gly Phe Ser Asp Leu Glu Lys
            20                  25                  30

<210> SEQ ID NO 17
<211> LENGTH: 20
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: PHOSPHORYLATION; tyrosine at position 12 is
      phosphorylated

<400> SEQUENCE: 17

Gly Leu Leu Pro Ser Gln Tyr Gly Gln Glu Val Tyr Asp Thr Pro Pro
1               5                   10                  15
```

Met Ala Val Lys
            20

<210> SEQ ID NO 18
<211> LENGTH: 12
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 18

Arg Pro Gly Pro Gly Thr Leu Tyr Asp Val Pro Arg
1               5                   10

<210> SEQ ID NO 19
<211> LENGTH: 15
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: PHOSPHORYLATION; tyrosine at position 12 is
      phosphorylated

<400> SEQUENCE: 19

Phe Pro Val Leu Val Thr Ser Asp Leu Asp His Tyr Leu Arg Arg
1               5                   10                  15

<210> SEQ ID NO 20
<211> LENGTH: 12
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: PHOSPHORYLATION; tyrosine at position 10 is
      phosphorylated

<400> SEQUENCE: 20

Gln Ala Gly Pro Gln Asp Thr Val Val Tyr Thr Arg
1               5                   10

<210> SEQ ID NO 21
<211> LENGTH: 11
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: PHOSPHORYLATION; tyrosine at position 6 is
      phosphorylated

<400> SEQUENCE: 21

Tyr Ile Gln Thr Val Tyr Ser Thr Ser Asp Arg
1               5                   10

<210> SEQ ID NO 22
<211> LENGTH: 17
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: PHOSPHORYLATION; tyrosine at position 5 is
      phosphorylated

<400> SEQUENCE: 22

```
Thr Lys Ser Gln Tyr His Asp Leu Gln Ala Pro Asp Asn Gln Gln Thr
1               5                   10                  15

Lys

<210> SEQ ID NO 23
<211> LENGTH: 17
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: PHOSPHORYLATION; tyrosine at position 9 is
      phosphorylated

<400> SEQUENCE: 23

Ala Gly Lys Gly Glu Ser Ala Gly Tyr Met Glu Pro Tyr Glu Ala Gln
1               5                   10                  15

Arg

<210> SEQ ID NO 24
<211> LENGTH: 20
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: PHOSPHORYLATION; tyrosine at position 12 is
      phosphorylated

<400> SEQUENCE: 24

Leu Pro Gln Asp Asp Arg Pro Ala Asp Glu Tyr Asp Gln Pro Trp
1               5                   10                  15

Glu Trp Asn Arg
            20

<210> SEQ ID NO 25
<211> LENGTH: 25
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: PHOSPHORYLATION; tyrosine at position 10 is
      phosphorylated

<400> SEQUENCE: 25

Gln Gln Ser Thr Thr Leu Ser Thr Leu Tyr Pro Ser Thr Ser Ser Leu
1               5                   10                  15

Leu Thr Asn His Gln His Glu Gly Arg
            20                  25

<210> SEQ ID NO 26
<211> LENGTH: 13
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: PHOSPHORYLATION; tyrosine at position 3 is
      phosphorylated

<400> SEQUENCE: 26

Ser Leu Tyr Pro Ser Ser Glu Ile Gln Leu Asn Asn Lys
1               5                   10
```

-continued

```
<210> SEQ ID NO 27
<211> LENGTH: 34
<212> TYPE: PRT
<213> ORGANISM: Homo sapiens
<220> FEATURE:
<221> NAME/KEY: MOD_RES
<222> LOCATION: (32)..(32)
<223> OTHER INFORMATION: PHOSPHORYLATION; tyrosine at position 32 is
      phosphorylated

<400> SEQUENCE: 27

Val Ile Gln Ala Gln Thr Ala Phe Ser Ala Asn Pro Ala Asn Pro Ala
1               5                   10                  15

Ile Leu Ser Glu Ala Ser Ala Pro Ile Pro His Asp Gly Asn Leu Tyr
            20                  25                  30

Pro Arg

<210> SEQ ID NO 28
<211> LENGTH: 27
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: PHOSPHORYLATION; tyrosine at position 4 is
      phosphorylated

<400> SEQUENCE: 28

Trp Asp Ser Tyr Glu Asn Leu Ser Ala Asp Gly Glu Val Leu His Thr
1               5                   10                  15

Gln Gly Pro Val Asp Gly Ser Leu Tyr Ala Lys
            20                  25

<210> SEQ ID NO 29
<211> LENGTH: 27
<212> TYPE: PRT
<213> ORGANISM: Homo sapiens
<220> FEATURE:
<221> NAME/KEY: MOD_RES
<222> LOCATION: (25)..(25)
<223> OTHER INFORMATION: PHOSPHORYLATION; tyrosine at position 25 is
      phosphorylated

<400> SEQUENCE: 29

Trp Asp Ser Tyr Glu Asn Leu Ser Ala Asp Gly Glu Val Leu His Thr
1               5                   10                  15

Gln Gly Pro Val Asp Gly Ser Leu Tyr Ala Lys
            20                  25

<210> SEQ ID NO 30
<211> LENGTH: 23
<212> TYPE: PRT
<213> ORGANISM: Homo sapiens
<220> FEATURE:
<221> NAME/KEY: MOD_RES
<222> LOCATION: (16)..(16)
<223> OTHER INFORMATION: PHOSPHORYLATION; tyrosine at position 16 is
      phosphorylated

<400> SEQUENCE: 30

Lys Pro Ser Val Ser Ala Gln Met Gln Ala Tyr Gly Gln Ser Ser Tyr
1               5                   10                  15

Ser Thr Gln Thr Trp Val Arg
            20

<210> SEQ ID NO 31
```

```
<211> LENGTH: 19
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: PHOSPHORYLATION; tyrosine at position 10 is
      phosphorylated

<400> SEQUENCE: 31

Gln Gln Gln Met Val Val Ala His Gln Tyr Ser Phe Ala Pro Asp Gly
1               5                   10                  15

Glu Ala Arg

<210> SEQ ID NO 32
<211> LENGTH: 19
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION; tyrosine at position 7 is
      phosphorylated

<400> SEQUENCE: 32

Lys Leu Ser Leu Gly Gln Tyr Asp Asn Asp Ala Gly Gly Gln Leu Pro
1               5                   10                  15

Phe Ser Lys

<210> SEQ ID NO 33
<211> LENGTH: 19
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: PHOSPHORYLATION; tyrosine at position 5 is
      phosphorylated

<400> SEQUENCE: 33

Ala Gly Val Asp Tyr Ala Pro Asn Leu Pro Pro Phe Pro Ser Pro Ala
1               5                   10                  15

Asp Val Lys

<210> SEQ ID NO 34
<211> LENGTH: 12
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: PHOSPHORYLATION; tyrosine at position 6 is
      phosphorylated

<400> SEQUENCE: 34

Tyr Glu Ser Ser Ser Tyr Thr Asp Gln Phe Ser Arg
1               5                   10

<210> SEQ ID NO 35
<211> LENGTH: 15
<212> TYPE: PRT
<213> ORGANISM: Homo sapiens
<220> FEATURE:
<221> NAME/KEY: MOD_RES
<222> LOCATION: (13)..(13)
<223> OTHER INFORMATION: PHOSPHORYLATION; tyrosine at position 13 is
      phosphorylated
```

```
<400> SEQUENCE: 35

Ser Asn His Tyr Asp Pro Glu Glu Asp Glu Tyr Tyr Arg Lys
1               5                   10                  15

<210> SEQ ID NO 36
<211> LENGTH: 17
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: PHOSPHORYLATION; tyrosine at position 11 is
      phosphorylated

<400> SEQUENCE: 36

Met Ser Tyr Leu Thr Ala Met Gly Ala Asp Tyr Leu Ser Cys Asp Ser
1               5                   10                  15

Arg

<210> SEQ ID NO 37
<211> LENGTH: 17
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 37

Ser Thr His Ala Ser Asn Asp Tyr Val Glu Arg Pro Pro Ala Pro Cys
1               5                   10                  15

Lys

<210> SEQ ID NO 38
<211> LENGTH: 28
<212> TYPE: PRT
<213> ORGANISM: Homo sapiens
<220> FEATURE:
<221> NAME/KEY: MOD_RES
<222> LOCATION: (13)..(13)
<223> OTHER INFORMATION: PHOSPHORYLATION; tyrosine at position 13 is
      phosphorylated

<400> SEQUENCE: 38

Glu Val Thr Thr Val Leu Gln Ala Asp Ser Ala Glu Tyr Ala Gln Pro
1               5                   10                  15

Leu Val Gly Gly Ile Val Gly Thr Leu His Gln Arg
            20                  25

<210> SEQ ID NO 39
<211> LENGTH: 28
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: PHOSPHORYLATION; tyrosine at position 14 is
      phosphorylated

<400> SEQUENCE: 39

Ala Gly Lys Pro Gly Leu Pro Ala Pro Asp Glu Leu Val Tyr Gln Val
1               5                   10                  15

Pro Gln Ser Thr Gln Glu Val Ser Gly Ala Gly Arg
            20                  25
```

```
<210> SEQ ID NO 40
<211> LENGTH: 31
<212> TYPE: PRT
<213> ORGANISM: Homo sapiens
<220> FEATURE:
<221> NAME/KEY: MOD_RES
<222> LOCATION: (15)..(15)
<223> OTHER INFORMATION: PHOSPHORYLATION; tyrosine at position 15 is
      phosphorylated

<400> SEQUENCE: 40

Ser His Ser Ile Thr Asn Met Glu Ile Gly Gly Leu Lys Ile Tyr Asp
1               5                   10                  15

Ile Leu Ser Asp Asn Gly Pro Gln Gln Pro Ser Thr Thr Val Lys
            20                  25                  30

<210> SEQ ID NO 41
<211> LENGTH: 17
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: PHOSPHORYLATION; tyrosine at position 9 is
      phosphorylated

<400> SEQUENCE: 41

Asp Thr Tyr His Pro Met Ser Glu Tyr Pro Thr Tyr His Thr His Gly
1               5                   10                  15

Arg

<210> SEQ ID NO 42
<211> LENGTH: 17
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: PHOSPHORYLATION; tyrosine at position 12 is
      phosphorylated

<400> SEQUENCE: 42

Asp Thr Tyr His Pro Met Ser Glu Tyr Pro Thr Tyr His Thr His Gly
1               5                   10                  15

Arg

<210> SEQ ID NO 43
<211> LENGTH: 24
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: PHOSPHORYLATION; tyrosine at position 12 is
      phosphorylated

<400> SEQUENCE: 43

Val Ser Ala Gly Asn Gly Gly Ser Ser Leu Ser Tyr Thr Asn Pro Ala
1               5                   10                  15

Val Ala Ala Thr Ser Ala Asn Leu
            20

<210> SEQ ID NO 44
<211> LENGTH: 18
<212> TYPE: PRT
<213> ORGANISM: Homo sapiens
```

```
<220> FEATURE:
<221> NAME/KEY: MOD_RES
<222> LOCATION: (9)..(9)
<223> OTHER INFORMATION: PHOSPHORYLATION; tyrosine at position 9 is
      phosphorylated

<400> SEQUENCE: 44

Tyr Asp Glu Asp Ala Lys Arg Pro Tyr Phe Thr Val Asp Glu Ala Glu
1               5                   10                  15

Ala Arg

<210> SEQ ID NO 45
<211> LENGTH: 13
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 45

Ala His Tyr Thr His Ser Asp Tyr Gln Tyr Ser Gln Arg
1               5                   10

<210> SEQ ID NO 46
<211> LENGTH: 13
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: PHOSPHORYLATION; tyrosine at position 10 is
      phosphorylated

<400> SEQUENCE: 46

Ala His Tyr Thr His Ser Asp Tyr Gln Tyr Ser Gln Arg
1               5                   10

<210> SEQ ID NO 47
<211> LENGTH: 25
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION; tyrosine at position 7 is
      phosphorylated

<400> SEQUENCE: 47

Ala Ala Ser Val Leu Leu Tyr Ser Leu Trp Ala His Thr Glu Leu His
1               5                   10                  15

His Ala Tyr Lys Lys Ala Gln Phe Lys
            20                  25

<210> SEQ ID NO 48
<211> LENGTH: 9
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: PHOSPHORYLATION; tyrosine at position 3 is
      phosphorylated

<400> SEQUENCE: 48

Ala Asp Tyr Asp Thr Leu Ser Leu Arg
1               5
```

<210> SEQ ID NO 49
<211> LENGTH: 26
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: PHOSPHORYLATION; tyrosine at position 10 is
      phosphorylated

<400> SEQUENCE: 49

Leu Gly Pro Gly Gly Leu Asp Asp Arg Tyr Ser Leu Val Ser Glu Gln
1               5                   10                  15

Leu Glu Pro Ala Ala Thr Ser Thr Tyr Arg
            20                  25

<210> SEQ ID NO 50
<211> LENGTH: 12
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: PHOSPHORYLATION; tyrosine at position 5 is
      phosphorylated

<400> SEQUENCE: 50

Ser Thr Thr Asn Tyr Val Asp Phe Tyr Ser Thr Lys
1               5                   10

<210> SEQ ID NO 51
<211> LENGTH: 27
<212> TYPE: PRT
<213> ORGANISM: Homo sapiens
<220> FEATURE:
<221> NAME/KEY: MOD_RES
<222> LOCATION: (13)..(13)
<223> OTHER INFORMATION: PHOSPHORYLATION; tyrosine at position 13 is
      phosphorylated

<400> SEQUENCE: 51

Ser Ser Thr Gln Met Asn Ser Tyr Ser Asp Ser Gly Tyr Gln Glu Ala
1               5                   10                  15

Gly Ser Phe His Asn Ser Gln Asn Val Ser Lys
            20                  25

<210> SEQ ID NO 52
<211> LENGTH: 18
<212> TYPE: PRT
<213> ORGANISM: Homo sapiens
<220> FEATURE:
<221> NAME/KEY: MOD_RES
<222> LOCATION: (16)..(16)
<223> OTHER INFORMATION: PHOSPHORYLATION; tyrosine at position 16 is
      phosphorylated

<400> SEQUENCE: 52

Thr Val His Asp Met Glu Gln Phe Gly Gln Gln Gln Tyr Asp Ile Tyr
1               5                   10                  15

Glu Arg

<210> SEQ ID NO 53
<211> LENGTH: 21
<212> TYPE: PRT
<213> ORGANISM: Homo sapiens
<220> FEATURE:

```
<221> NAME/KEY: MOD_RES
<222> LOCATION: (3)..(3)
<223> OTHER INFORMATION: PHOSPHORYLATION; tyrosine at position 3 is
      phosphorylated

<400> SEQUENCE: 53

Asn Asn Tyr Ala Leu Asn Thr Thr Ala Thr Tyr Ala Glu Pro Tyr Arg
1               5                   10                  15

Pro Ile Gln Tyr Arg
            20

<210> SEQ ID NO 54
<211> LENGTH: 14
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: PHOSPHORYLATION; tyrosine at position 6 is
      phosphorylated

<400> SEQUENCE: 54

Thr Ala Ser Gly Asp Tyr Ile Asp Ser Ser Trp Glu Leu Arg
1               5                   10

<210> SEQ ID NO 55
<211> LENGTH: 25
<212> TYPE: PRT
<213> ORGANISM: Homo sapiens
<220> FEATURE:
<221> NAME/KEY: MOD_RES
<222> LOCATION: (21)..(21)
<223> OTHER INFORMATION: PHOSPHORYLATION; tyrosine at position 21 is
      phosphorylated

<400> SEQUENCE: 55

Leu Gly His Pro Glu Ala Leu Ser Ala Gly Thr Gly Ser Pro Gln Pro
1               5                   10                  15

Pro Ser Phe Thr Tyr Ala Gln Gln Arg
            20                  25

<210> SEQ ID NO 56
<211> LENGTH: 27
<212> TYPE: PRT
<213> ORGANISM: Homo sapiens
<220> FEATURE:
<221> NAME/KEY: MOD_RES
<222> LOCATION: (23)..(23)
<223> OTHER INFORMATION: PHOSPHORYLATION; tyrosine at position 23 is
      phosphorylated

<400> SEQUENCE: 56

Val Ile Gln Pro His Gly Gly Gly Ser Asn Pro Leu Glu Gly Thr Gln
1               5                   10                  15

His Leu Gln Asp Val Pro Tyr Val Met Val Arg
            20                  25

<210> SEQ ID NO 57
<211> LENGTH: 30
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: PHOSPHORYLATION; tyrosine at position 12 is
      phosphorylated

<400> SEQUENCE: 57
```

```
Glu Pro Ser Ala Pro Ser Ile Pro Thr Pro Ala Tyr Gln Ser Ser Pro
1               5                   10                  15

Ala Gly Gly His Ala Pro Thr Pro Pro Thr Pro Ala Pro Arg
                20                  25                  30

<210> SEQ ID NO 58
<211> LENGTH: 17
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: PHOSPHORYLATION; tyrosine at position 9 is
      phosphorylated

<400> SEQUENCE: 58

Ala Asn Leu His Ala Glu Pro Asp Tyr Leu Glu Val Leu Glu Gln Gln
1               5                   10                  15

Thr

<210> SEQ ID NO 59
<211> LENGTH: 19
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: PHOSPHORYLATION; tyrosine at position 2 is
      phosphorylated

<400> SEQUENCE: 59

Ala Tyr Thr Asn Phe Asp Ala Glu Arg Asp Ala Leu Asn Ile Glu Thr
1               5                   10                  15

Ala Ile Lys

<210> SEQ ID NO 60
<211> LENGTH: 22
<212> TYPE: PRT
<213> ORGANISM: Homo sapiens
<220> FEATURE:
<221> NAME/KEY: MOD_RES
<222> LOCATION: (15)..(15)
<223> OTHER INFORMATION: PHOSPHORYLATION; tyrosine at position 15 is
      phosphorylated

<400> SEQUENCE: 60

Val Leu Val Ser Leu Ser Ala Gly Gly Arg Asp Glu Gly Asn Tyr Leu
1               5                   10                  15

Asp Asp Ala Leu Val Arg
                20

<210> SEQ ID NO 61
<211> LENGTH: 21
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: PHOSPHORYLATION; tyrosine at position 10 is
      phosphorylated

<400> SEQUENCE: 61

Asn Glu Lys Ala Pro Val Asp Phe Gly Tyr Val Gly Ile Asp Ser Ile
1               5                   10                  15

Leu Glu Gln Met Arg
```

-continued

```
<210> SEQ ID NO 62
<211> LENGTH: 32
<212> TYPE: PRT
<213> ORGANISM: Homo sapiens
<220> FEATURE:
<221> NAME/KEY: MOD_RES
<222> LOCATION: (19)..(19)
<223> OTHER INFORMATION: PHOSPHORYLATION; tyrosine at position 19 is
      phosphorylated

<400> SEQUENCE: 62

Leu Ala Thr Glu Glu Pro Pro Arg Ser Pro Pro Glu Ser Glu Ser
1               5                   10                  15

Glu Pro Tyr Thr Phe Ser His Pro Asn Asn Gly Asp Val Ser Ser Lys
            20                  25                  30

<210> SEQ ID NO 63
<211> LENGTH: 16
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: PHOSPHORYLATION; tyrosine at position 14 is
      phosphorylated

<400> SEQUENCE: 63

Ser Arg Leu Arg Asp Pro Ile Lys Pro Gly Met Phe Gly Tyr Gly Arg
1               5                   10                  15

<210> SEQ ID NO 64
<211> LENGTH: 25
<212> TYPE: PRT
<213> ORGANISM: Homo sapiens
<220> FEATURE:
<221> NAME/KEY: MOD_RES
<222> LOCATION: (20)..(20)
<223> OTHER INFORMATION: PHOSPHORYLATION; tyrosine at position 20 is
      phosphorylated

<400> SEQUENCE: 64

Tyr Gly Ala Phe Val Lys Pro Ala Val Val Thr Val Gly Asp Phe Pro
1               5                   10                  15

Glu Glu Asp Tyr Gly Leu Asp Glu Ile
            20                  25

<210> SEQ ID NO 65
<211> LENGTH: 18
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: PHOSPHORYLATION; tyrosine at position 10 is
      phosphorylated

<400> SEQUENCE: 65

Ala Ile Met Thr Tyr Val Ser Ser Phe Tyr His Ala Phe Ser Gly Ala
1               5                   10                  15

Gln Lys

<210> SEQ ID NO 66
<211> LENGTH: 14
<212> TYPE: PRT
<213> ORGANISM: Homo sapiens
```

```
<220> FEATURE:
<221> NAME/KEY: MOD_RES
<222> LOCATION: (12)..(12)
<223> OTHER INFORMATION: PHOSPHORYLATION; tyrosine at position 12 is
      phosphorylated

<400> SEQUENCE: 66

Ser Thr Gly Pro Gly Ala Ser Leu Gly Thr Gly Tyr Asp Arg
1               5                   10

<210> SEQ ID NO 67
<211> LENGTH: 8
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION; tyrosine at position 7 is
      phosphorylated

<400> SEQUENCE: 67

Ser Ala Ala Ala Ser Asn Tyr Val
1               5

<210> SEQ ID NO 68
<211> LENGTH: 31
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: PHOSPHORYLATION; tyrosine at position 10 is
      phosphorylated

<400> SEQUENCE: 68

Ser Leu Gly Ser Val Gln Ala Pro Ser Tyr Gly Ala Arg Pro Val Ser
1               5                   10                  15

Ser Ala Ala Ser Val Tyr Ala Gly Ala Gly Gly Ser Gly Ser Arg
            20                  25                  30

<210> SEQ ID NO 69
<211> LENGTH: 17
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: PHOSPHORYLATION; tyrosine at position 10 is
      phosphorylated

<400> SEQUENCE: 69

Ser Leu Leu Glu Gly Gln Glu Asp His Tyr Asn Asn Leu Ser Ala Ser
1               5                   10                  15

Lys

<210> SEQ ID NO 70
<211> LENGTH: 23
<212> TYPE: PRT
<213> ORGANISM: Homo sapiens
<220> FEATURE:
<221> NAME/KEY: MOD_RES
<222> LOCATION: (15)..(15)
<223> OTHER INFORMATION: PHOSPHORYLATION; tyrosine at position 15 is
      phosphorylated

<400> SEQUENCE: 70

Leu Ser Ser Ala Arg Pro Gly Gly Leu Gly Ser Ser Ser Leu Tyr Gly
1               5                   10                  15
```

Leu Gly Ala Ser Arg Pro Arg
            20

<210> SEQ ID NO 71
<211> LENGTH: 40
<212> TYPE: PRT
<213> ORGANISM: Homo sapiens
<220> FEATURE:
<221> NAME/KEY: MOD_RES
<222> LOCATION: (23)..(23)
<223> OTHER INFORMATION: PHOSPHORYLATION; tyrosine at position 23 is
      phosphorylated

<400> SEQUENCE: 71

Thr Thr Ser Gly Tyr Ala Gly Gly Leu Ser Ser Ala Tyr Gly Gly Leu
1               5                   10                  15

Thr Ser Pro Gly Leu Ser Tyr Ser Leu Gly Ser Ser Phe Gly Ser Gly
            20                  25                  30

Ala Gly Ser Ser Ser Phe Ser Arg
        35                  40

<210> SEQ ID NO 72
<211> LENGTH: 19
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: PHOSPHORYLATION; tyrosine at position 12 is
      phosphorylated

<400> SEQUENCE: 72

Ala Ser Ala Ser Gly Asp Asp Ser His Phe Asp Tyr Val His Asp Gln
1               5                   10                  15

Asn Gln Lys

<210> SEQ ID NO 73
<211> LENGTH: 17
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: PHOSPHORYLATION; tyrosine at position 14 is
      phosphorylated

<400> SEQUENCE: 73

Glu Val Cys Asp Gly Trp Ser Leu Pro Asn Pro Glu Tyr Tyr Thr Leu
1               5                   10                  15

Arg

<210> SEQ ID NO 74
<211> LENGTH: 9
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: PHOSPHORYLATION; tyrosine at position 3 is
      phosphorylated

<400> SEQUENCE: 74

Ala Gln Tyr Asp Asp Ile Val Thr Arg
1               5

```
<210> SEQ ID NO 75
<211> LENGTH: 18
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: PHOSPHORYLATION; tyrosine at position 2 is
      phosphorylated

<400> SEQUENCE: 75

Gly Tyr Tyr Ser Pro Tyr Ser Val Ser Gly Ser Gly Ser Thr Ala Gly
1               5                   10                  15

Ser Arg

<210> SEQ ID NO 76
<211> LENGTH: 14
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: PHOSPHORYLATION; tyrosine at position 10 is
      phosphorylated

<400> SEQUENCE: 76

Gly Ala Ser Gln Ala Gly Met Thr Gly Tyr Gly Met Pro Arg
1               5                   10

<210> SEQ ID NO 77
<211> LENGTH: 15
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: PHOSPHORYLATION; tyrosine at position 11 is
      phosphorylated.

<400> SEQUENCE: 77

Thr Met Gln Phe Glu Pro Ser Thr Met Val Tyr Asp Ala Cys Arg
1               5                   10                  15

<210> SEQ ID NO 78
<211> LENGTH: 14
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION; tyrosine at position 7 is
      phosphorylated

<400> SEQUENCE: 78

His Ala Ser Gln Lys Asp Tyr Ser Ser Gly Phe Gly Gly Lys
1               5                   10

<210> SEQ ID NO 79
<211> LENGTH: 28
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 79

Val Thr Glu Trp Gln Gln Thr Tyr Thr Tyr Asp Ser Gly Ile His Ser
```

```
                    1               5                  10                 15
Gly Ala Asn Thr Cys Val Pro Ser Val Ser Ser Lys
                20                  25

<210> SEQ ID NO 80
<211> LENGTH: 25
<212> TYPE: PRT
<213> ORGANISM: Homo sapiens
<220> FEATURE:
<221> NAME/KEY: MOD_RES
<222> LOCATION: (18)..(18)
<223> OTHER INFORMATION: PHOSPHORYLATION; tyrosine at position 18 is
      phosphorylated

<400> SEQUENCE: 80

Lys Thr Thr Thr Tyr Thr Gln Gly Val Pro Pro Ser Gln Gly Asp Leu
1               5                  10                 15
Glu Tyr Gln Met Ser Thr Thr Ala Arg
                20                  25

<210> SEQ ID NO 81
<211> LENGTH: 21
<212> TYPE: PRT
<213> ORGANISM: Homo sapiens
<220> FEATURE:
<221> NAME/KEY: MOD_RES
<222> LOCATION: (17)..(17)
<223> OTHER INFORMATION: PHOSPHORYLATION; tyrosine at position 17 is
      phosphorylated

<400> SEQUENCE: 81

Glu Leu Pro Gln Lys Ile Val Gly Glu Asn Ser Leu Glu Tyr Ser Glu
1               5                  10                 15
Tyr Met Thr Gly Lys
                20

<210> SEQ ID NO 82
<211> LENGTH: 23
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 82

Gly Ile Leu Phe Val Lys Glu Tyr Val Asn Ala Ser Glu Val Ser Ser
1               5                  10                 15
Gly Lys Pro Val Ser Ala Arg
                20

<210> SEQ ID NO 83
<211> LENGTH: 29
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: PHOSPHORYLATION; tyrosine at position 6 is
      phosphorylated

<400> SEQUENCE: 83

Thr Ala Leu Glu Lys Tyr His Asp Gly Ile Glu Lys Ala Ala Glu Asp
1               5                  10                 15
Ser Tyr Ala Lys Ile Asp Glu Lys Thr Ala Glu Leu Lys
```

```
<210> SEQ ID NO 84
<211> LENGTH: 12
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: PHOSPHORYLATION; tyrosine at position 1 is
      phosphorylated

<400> SEQUENCE: 84

Tyr Lys Gln Asp Val Glu Arg Phe Tyr Glu Arg Lys
1               5                   10

<210> SEQ ID NO 85
<211> LENGTH: 16
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 85

Asn Ser Tyr Val Ala Gly Gln Tyr Asp Asp Ala Ala Ser Tyr Gln Arg
1               5                   10                  15

<210> SEQ ID NO 86
<211> LENGTH: 11
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: PHOSPHORYLATION; tyrosine at position 6 is
      phosphorylated

<400> SEQUENCE: 86

Arg Val Gly Phe Gln Tyr Glu Gly Thr Tyr Lys
1               5                   10

<210> SEQ ID NO 87
<211> LENGTH: 10
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: PHOSPHORYLATION; tyrosine at position 9 is
      phosphorylated

<400> SEQUENCE: 87

Val Gly Phe Gln Tyr Glu Gly Thr Tyr Lys
1               5                   10

<210> SEQ ID NO 88
<211> LENGTH: 22
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION; tyrosine at position 7 is
      phosphorylated

<400> SEQUENCE: 88
```

```
Lys Val Ser Ser Thr His Tyr Tyr Leu Leu Pro Glu Arg Pro Pro Tyr
1               5                   10                  15

Leu Asp Lys Tyr Glu Lys
            20
```

<210> SEQ ID NO 89
<211> LENGTH: 21
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION; tyrosine at position 7 is
      phosphorylated

<400> SEQUENCE: 89

```
Val Ser Ser Thr His Tyr Tyr Leu Leu Pro Glu Arg Pro Pro Tyr Leu
1               5                   10                  15

Asp Lys Tyr Glu Lys
            20
```

<210> SEQ ID NO 90
<211> LENGTH: 16
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION; tyrosine at position 7 is
      phosphorylated

<400> SEQUENCE: 90

```
Gly Tyr Ser Asp Glu Ile Tyr Val Val Pro Asp Asp Ser Gln Asn Arg
1               5                   10                  15
```

<210> SEQ ID NO 91
<211> LENGTH: 19
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: PHOSPHORYLATION; tyrosine at position 9 is
      phosphorylated

<400> SEQUENCE: 91

```
Leu Ile Asn Ser Ser Gln Leu Leu Tyr Gln Glu Tyr Ser Asp Val Val
1               5                   10                  15

Leu Asn Lys
```

<210> SEQ ID NO 92
<211> LENGTH: 14
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: PHOSPHORYLATION; tyrosine at position 6 is
      phosphorylated

<400> SEQUENCE: 92

```
Cys Leu Glu Glu His Tyr Gly Thr Ser Pro Gly Gln Ala Arg
1               5                   10
```

<210> SEQ ID NO 93
<211> LENGTH: 20
<212> TYPE: PRT

```
<213> ORGANISM: Homo sapiens
<220> FEATURE:
<221> NAME/KEY: MOD_RES
<222> LOCATION: (9)..(9)
<223> OTHER INFORMATION: PHOSPHORYLATION; tyrosine at position 9 is
      phosphorylated

<400> SEQUENCE: 93

Phe Met Pro Leu Ser Asp Val Leu Tyr Gly Arg Val Ala Asp Phe Leu
1               5                   10                  15

Ser Trp Cys Arg
            20

<210> SEQ ID NO 94
<211> LENGTH: 14
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: PHOSPHORYLATION; tyrosine at position 5 is
      phosphorylated

<400> SEQUENCE: 94

Gly Ile Val Val Tyr Thr Gly Asp Arg Thr Val Met Gly Arg
1               5                   10

<210> SEQ ID NO 95
<211> LENGTH: 34
<212> TYPE: PRT
<213> ORGANISM: Homo sapiens
<220> FEATURE:
<221> NAME/KEY: MOD_RES
<222> LOCATION: (29)..(29)
<223> OTHER INFORMATION: PHOSPHORYLATION; tyrosine at position 29 is
      phosphorylated

<400> SEQUENCE: 95

Gly Pro Ala Ser Asp Tyr Gly Pro Glu Pro Thr Pro Pro Gly Pro Ala
1               5                   10                  15

Ala Pro Ala Gly Thr Asp Thr Thr Ser Gln Leu Ser Tyr Glu Asn Tyr
            20                  25                  30

Glu Lys

<210> SEQ ID NO 96
<211> LENGTH: 34
<212> TYPE: PRT
<213> ORGANISM: Homo sapiens
<220> FEATURE:
<221> NAME/KEY: MOD_RES
<222> LOCATION: (32)..(32)
<223> OTHER INFORMATION: PHOSPHORYLATION; tyrosine at position 32 is
      phosphorylated

<400> SEQUENCE: 96

Gly Pro Ala Ser Asp Tyr Gly Pro Glu Pro Thr Pro Pro Gly Pro Ala
1               5                   10                  15

Ala Pro Ala Gly Thr Asp Thr Thr Ser Gln Leu Ser Tyr Glu Asn Tyr
            20                  25                  30

Glu Lys

<210> SEQ ID NO 97
<211> LENGTH: 23
<212> TYPE: PRT
<213> ORGANISM: Homo sapiens
<220> FEATURE:
```

```
<221> NAME/KEY: MOD_RES
<222> LOCATION: (15)..(15)
<223> OTHER INFORMATION: PHOSPHORYLATION; tyrosine at position 15 is
      phosphorylated

<400> SEQUENCE: 97

Glu Thr Pro Asn Ile Cys Pro His Ser Gly Glu Asn Thr Glu Tyr Asp
1               5                   10                  15

Thr Ile Pro His Thr Asn Arg
            20

<210> SEQ ID NO 98
<211> LENGTH: 16
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION; tyrosine at position 7 is
      phosphorylated

<400> SEQUENCE: 98

Leu Leu Gly Ser Val Asp Tyr Asp Gly Ile Asn Asp Ala Ile Thr Arg
1               5                   10                  15

<210> SEQ ID NO 99
<211> LENGTH: 13
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: PHOSPHORYLATION; tyrosine at position 11 is
      phosphorylated

<400> SEQUENCE: 99

Ser Arg Glu Tyr Asp Gln Leu Tyr Glu Glu Tyr Thr Arg
1               5                   10

<210> SEQ ID NO 100
<211> LENGTH: 22
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION; tyrosine at position 7 is
      phosphorylated

<400> SEQUENCE: 100

Asn Glu Thr Glu Asp Gln Tyr Ala Leu Met Glu Asp Glu Asp Asp Leu
1               5                   10                  15

Pro His His Glu Glu Arg
            20

<210> SEQ ID NO 101
<211> LENGTH: 12
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: PHOSPHORYLATION; tyrosine at position 6 is
      phosphorylated

<400> SEQUENCE: 101

Thr Thr Glu Asn Asn Tyr Cys Pro His Tyr Glu Lys
1               5                   10
```

```
<210> SEQ ID NO 102
<211> LENGTH: 12
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: PHOSPHORYLATION; tyrosine at position 10 is
      phosphorylated

<400> SEQUENCE: 102

Thr Thr Glu Asn Asn Tyr Cys Pro His Tyr Glu Lys
1               5                   10

<210> SEQ ID NO 103
<211> LENGTH: 32
<212> TYPE: PRT
<213> ORGANISM: Homo sapiens
<220> FEATURE:
<221> NAME/KEY: MOD_RES
<222> LOCATION: (21)..(21)
<223> OTHER INFORMATION: PHOSPHORYLATION; tyrosine at position 21 is
      phosphorylated

<400> SEQUENCE: 103

Leu Asn Ser Leu Pro Ser Glu Tyr Glu Ser Gly Ser Ala Cys Pro Ala
1               5                   10                  15

Gln Thr Val His Tyr Arg Pro Ile Asn Leu Ser Ser Ser Glu Asn Lys
            20                  25                  30

<210> SEQ ID NO 104
<211> LENGTH: 10
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: PHOSPHORYLATION; tyrosine at position 5 is
      phosphorylated

<400> SEQUENCE: 104

Gly Val Ile Ser Tyr Gln Thr Leu Pro Arg
1               5                   10

<210> SEQ ID NO 105
<211> LENGTH: 14
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: PHOSPHORYLATION; tyrosine at position 5 is
      phosphorylated

<400> SEQUENCE: 105

Ser Glu Asp Ile Tyr Ala Asp Pro Ala Ala Tyr Val Met Arg
1               5                   10

<210> SEQ ID NO 106
<211> LENGTH: 26
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: PHOSPHORYLATION; tyrosine at position 5 is
      phosphorylated
```

```
<400> SEQUENCE: 106

Ser Val Thr Asp Tyr Asp Phe Ala Pro Phe Leu Asn Asn Ser Pro Gln
1               5                   10                  15

Gln Asn Pro Ala Ala Gln Ile Pro Ala Arg
            20                  25

<210> SEQ ID NO 107
<211> LENGTH: 16
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: PHOSPHORYLATION; tyrosine at position 10 is
      phosphorylated

<400> SEQUENCE: 107

Ile Pro Phe Ile Arg Pro Ala Asp Gln Tyr Lys Asp Pro Gln Ser Lys
1               5                   10                  15

<210> SEQ ID NO 108
<211> LENGTH: 19
<212> TYPE: PRT
<213> ORGANISM: Homo sapiens
<220> FEATURE:
<221> NAME/KEY: MOD_RES
<222> LOCATION: (19)..(19)
<223> OTHER INFORMATION: PHOSPHORYLATION; tyrosine at position 19 is
      phosphorylated

<400> SEQUENCE: 108

Ala Cys Asn Val Leu Gln Ser Ser His Leu Glu Asp Tyr Pro Phe Asp
1               5                   10                  15

Ala Glu Tyr

<210> SEQ ID NO 109
<211> LENGTH: 23
<212> TYPE: PRT
<213> ORGANISM: Homo sapiens
<220> FEATURE:
<221> NAME/KEY: MOD_RES
<222> LOCATION: (19)..(19)
<223> OTHER INFORMATION: PHOSPHORYLATION; tyrosine at position 19 is
      phosphorylated

<400> SEQUENCE: 109

Val Ser Ser Gln Gly Asn Leu Ile Pro Ala Arg Pro Ala Pro Ala Pro
1               5                   10                  15

Pro Leu Tyr Ser Ser Leu Thr
            20

<210> SEQ ID NO 110
<211> LENGTH: 16
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: PHOSPHORYLATION; tyrosine at position 3 is
      phosphorylated

<400> SEQUENCE: 110

Leu Leu Tyr Ala Leu Glu Ile Ile Glu Ala Leu Gly Lys Pro Asn Arg
1               5                   10                  15

<210> SEQ ID NO 111
```

```
<211> LENGTH: 22
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: PHOSPHORYLATION; tyrosine at position 2 is
      phosphorylated

<400> SEQUENCE: 111

Lys Tyr Leu Tyr Leu Val Leu Glu His Val Ser Gly Gly Glu Leu Phe
1               5                   10                  15

Asp Tyr Leu Val Lys Lys
            20

<210> SEQ ID NO 112
<211> LENGTH: 22
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: PHOSPHORYLATION; tyrosine at position 4 is
      phosphorylated

<400> SEQUENCE: 112

Lys Tyr Leu Tyr Leu Val Leu Glu His Val Ser Gly Gly Glu Leu Phe
1               5                   10                  15

Asp Tyr Leu Val Lys Lys
            20

<210> SEQ ID NO 113
<211> LENGTH: 13
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: PHOSPHORYLATION; tyrosine at position 9 is
      phosphorylated

<400> SEQUENCE: 113

His Ala Asp Ala Glu Met Thr Gly Tyr Val Val Thr Arg
1               5                   10

<210> SEQ ID NO 114
<211> LENGTH: 28
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: PHOSPHORYLATION; tyrosine at position 3 is
      phosphorylated

<400> SEQUENCE: 114

Asp Ala Tyr Glu Leu Gln Glu Val Ile Gly Ser Gly Ala Thr Ala Val
1               5                   10                  15

Val Gln Ala Ala Leu Cys Lys Pro Arg Gln Glu Arg
            20                  25

<210> SEQ ID NO 115
<211> LENGTH: 28
<212> TYPE: PRT
<213> ORGANISM: Homo sapiens
<220> FEATURE:
<221> NAME/KEY: MOD_RES
<222> LOCATION: (10)..(10)
```

```
<223> OTHER INFORMATION: PHOSPHORYLATION; tyrosine at position 10 is
      phosphorylated

<400> SEQUENCE: 115

Asn Leu Leu His Ala Asp Ser Asn Gly Tyr Thr Asn Leu Pro Asp Val
1               5                   10                  15

Val Gln Pro Ser His Ser Pro Thr Glu Asn Ser Lys
            20                  25

<210> SEQ ID NO 116
<211> LENGTH: 14
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: PHOSPHORYLATION; tyrosine at position 4 is
      phosphorylated

<400> SEQUENCE: 116

His Gly His Tyr Phe Val Ala Leu Phe Asp Tyr Gln Ala Arg
1               5                   10

<210> SEQ ID NO 117
<211> LENGTH: 12
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION; tyrosine at position 7 is
      phosphorylated

<400> SEQUENCE: 117

Lys Leu Asp Asn Gly Gly Tyr Tyr Ile Thr Thr Arg
1               5                   10

<210> SEQ ID NO 118
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 118

Ile Gln Asn Thr Gly Asp Tyr Tyr Asp Leu Tyr Gly Gly Glu Lys
1               5                   10                  15

<210> SEQ ID NO 119
<211> LENGTH: 24
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 119

Gln Leu Ile Ile Glu Asp Pro Tyr Tyr Gly Asn Asp Ser Asp Phe Glu
1               5                   10                  15

Thr Val Tyr Gln Gln Cys Val Arg
            20
```

<210> SEQ ID NO 120
<211> LENGTH: 20
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: PHOSPHORYLATION; tyrosine at position 10 is
      phosphorylated

<400> SEQUENCE: 120

Tyr Leu Cys Glu Gly Thr Glu Ser Pro Tyr Gln Thr Gly Gln Leu His
1               5                   10                  15

Pro Ala Ile Arg
            20

<210> SEQ ID NO 121
<211> LENGTH: 35
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: PHOSPHORYLATION; tyrosine at position 12 is
      phosphorylated

<400> SEQUENCE: 121

Ala Lys Val Lys Lys Leu Thr Leu Gly Met Asp Tyr Met Phe Gln Val
1               5                   10                  15

Lys Lys Val Lys Gly Lys Gly Tyr Ser Val Ser Val Met Lys Lys Val
                20                  25                  30

Pro Ile Lys
        35

<210> SEQ ID NO 122
<211> LENGTH: 13
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: PHOSPHORYLATION; tyrosine at position 12 is
      phosphorylated

<400> SEQUENCE: 122

Met His Leu Pro Ser Pro Thr Asp Ser Asn Phe Tyr Arg
1               5                   10

<210> SEQ ID NO 123
<211> LENGTH: 31
<212> TYPE: PRT
<213> ORGANISM: Homo sapiens
<220> FEATURE:
<221> NAME/KEY: MOD_RES
<222> LOCATION: (25)..(25)
<223> OTHER INFORMATION: PHOSPHORYLATION; tyrosine at position 25 is
      phosphorylated

<400> SEQUENCE: 123

Phe Thr His Gln Ser Asp Val Trp Ser Tyr Gly Val Thr Val Trp Glu
1               5                   10                  15

Leu Met Thr Phe Gly Ala Lys Pro Tyr Asp Gly Ile Pro Ala Arg
                20                  25                  30

<210> SEQ ID NO 124
<211> LENGTH: 16
<212> TYPE: PRT

```
<213> ORGANISM: Homo sapiens
<220> FEATURE:
<221> NAME/KEY: MOD_RES
<222> LOCATION: (14)..(14)
<223> OTHER INFORMATION: PHOSPHORYLATION; tyrosine at position 14 is
      phosphorylated

<400> SEQUENCE: 124

Ala Phe Gln Gly Pro Gly His Gln Ala Pro His Val His Tyr Ala Arg
1               5                   10                  15

<210> SEQ ID NO 125
<211> LENGTH: 18
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: PHOSPHORYLATION; tyrosine at position 14 is
      phosphorylated

<400> SEQUENCE: 125

Ser Leu Glu Ala Thr Asp Ser Ala Phe Asp Asn Pro Asp Tyr Trp His
1               5                   10                  15

Ser Arg

<210> SEQ ID NO 126
<211> LENGTH: 18
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION; tyrosine at position 7 is
      phosphorylated

<400> SEQUENCE: 126

Gln Ser Pro Glu Asp Val Tyr Phe Ser Lys Ser Glu Gln Leu Lys Pro
1               5                   10                  15

Leu Lys

<210> SEQ ID NO 127
<211> LENGTH: 25
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: PHOSPHORYLATION; tyrosine at position 10 is
      phosphorylated

<400> SEQUENCE: 127

Ser Glu Gln Leu Lys Pro Leu Lys Thr Tyr Val Asp Pro His Thr Tyr
1               5                   10                  15

Glu Asp Pro Asn Gln Ala Val Leu Lys
            20                  25

<210> SEQ ID NO 128
<211> LENGTH: 25
<212> TYPE: PRT
<213> ORGANISM: Homo sapiens
<220> FEATURE:
<221> NAME/KEY: MOD_RES
<222> LOCATION: (16)..(16)
<223> OTHER INFORMATION: PHOSPHORYLATION; tyrosine at position 16 is
      phosphorylated

<400> SEQUENCE: 128
```

Ser Glu Gln Leu Lys Pro Leu Lys Thr Tyr Val Asp Pro His Thr Tyr
1               5                   10                  15

Glu Asp Pro Asn Gln Ala Val Leu Lys
            20                  25

<210> SEQ ID NO 129
<211> LENGTH: 16
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: PHOSPHORYLATION; tyrosine at position 2 is
      phosphorylated

<400> SEQUENCE: 129

Thr Tyr Val Asp Pro Phe Thr Tyr Glu Asp Pro Asn Gln Ala Val Arg
1               5                   10                  15

<210> SEQ ID NO 130
<211> LENGTH: 16
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 130

Thr Tyr Val Asp Pro Phe Thr Tyr Glu Asp Pro Asn Gln Ala Val Arg
1               5                   10                  15

<210> SEQ ID NO 131
<211> LENGTH: 20
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: PHOSPHORYLATION; tyrosine at position 2 is
      phosphorylated

<400> SEQUENCE: 131

Thr Tyr Ile Asp Pro His Thr Tyr Glu Asp Pro Asn Gln Ala Val His
1               5                   10                  15

Glu Phe Ala Lys
            20

<210> SEQ ID NO 132
<211> LENGTH: 20
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 132

Thr Tyr Ile Asp Pro His Thr Tyr Glu Asp Pro Asn Gln Ala Val His
1               5                   10                  15

Glu Phe Ala Lys
            20

<210> SEQ ID NO 133

```
<211> LENGTH: 13
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 133

Thr Tyr Ile Asp Pro Glu Thr Tyr Glu Asp Pro Asn Arg
1               5                   10

<210> SEQ ID NO 134
<211> LENGTH: 26
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: PHOSPHORYLATION; tyrosine at position 12 is
      phosphorylated

<400> SEQUENCE: 134

Leu Gln Gln Tyr Ile Ala Pro Gly Met Lys Val Tyr Ile Asp Pro Phe
1               5                   10                  15

Thr Tyr Glu Asp Pro Asn Glu Ala Val Arg
            20                  25

<210> SEQ ID NO 135
<211> LENGTH: 18
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: PHOSPHORYLATION; tyrosine at position 11 is
      phosphorylated

<400> SEQUENCE: 135

Phe Leu Glu Asp Asp Pro Ser Asp Pro Thr Tyr Thr Ser Ser Leu Gly
1               5                   10                  15

Gly Lys

<210> SEQ ID NO 136
<211> LENGTH: 18
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: PHOSPHORYLATION; tyrosine at position 4 is
      phosphorylated

<400> SEQUENCE: 136

Glu Ala Glu Tyr Ser Asp Lys His Gly Gln Tyr Leu Ile Gly His Gly
1               5                   10                  15

Thr Lys

<210> SEQ ID NO 137
<211> LENGTH: 27
<212> TYPE: PRT
<213> ORGANISM: Homo sapiens
<220> FEATURE:
<221> NAME/KEY: MOD_RES
<222> LOCATION: (13)..(13)
<223> OTHER INFORMATION: PHOSPHORYLATION; tyrosine at position 13 is
      phosphorylated
```

```
<400> SEQUENCE: 137

His Gly Gln Tyr Leu Ile Gly His Gly Thr Lys Val Tyr Ile Asp Pro
1               5                   10                  15

Phe Thr Tyr Glu Asp Pro Asn Glu Ala Val Arg
            20                  25

<210> SEQ ID NO 138
<211> LENGTH: 27
<212> TYPE: PRT
<213> ORGANISM: Homo sapiens
<220> FEATURE:
<221> NAME/KEY: MOD_RES
<222> LOCATION: (19)..(19)
<223> OTHER INFORMATION: PHOSPHORYLATION; tyrosine at position 19 is
      phosphorylated

<400> SEQUENCE: 138

His Gly Gln Tyr Leu Ile Gly His Gly Thr Lys Val Tyr Ile Asp Pro
1               5                   10                  15

Phe Thr Tyr Glu Asp Pro Asn Glu Ala Val Arg
            20                  25

<210> SEQ ID NO 139
<211> LENGTH: 18
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: PHOSPHORYLATION; tyrosine at position 11 is
      phosphorylated

<400> SEQUENCE: 139

Phe Leu Glu Glu Asn Ser Ser Asp Pro Thr Tyr Thr Ser Ser Leu Gly
1               5                   10                  15

Gly Lys

<210> SEQ ID NO 140
<211> LENGTH: 18
<212> TYPE: PRT
<213> ORGANISM: Homo sapiens
<220> FEATURE:
<221> NAME/KEY: MOD_RES
<222> LOCATION: (18)..(18)
<223> OTHER INFORMATION: PHOSPHORYLATION; tyrosine at position 18 is
      phosphorylated

<400> SEQUENCE: 140

Ser Gln Ala Lys Pro Gly Thr Pro Gly Gly Thr Gly Gly Pro Ala Pro
1               5                   10                  15

Gln Tyr

<210> SEQ ID NO 141
<211> LENGTH: 14
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION; tyrosine at position 7 is
      phosphorylated

<400> SEQUENCE: 141

Asp Ile Leu Asp Arg Glu Tyr Tyr Ser Val Gln Gln His Arg
1               5                   10
```

```
<210> SEQ ID NO 142
<211> LENGTH: 35
<212> TYPE: PRT
<213> ORGANISM: Homo sapiens
<220> FEATURE:
<221> NAME/KEY: MOD_RES
<222> LOCATION: (19)..(19)
<223> OTHER INFORMATION: PHOSPHORYLATION; tyrosine at position 19 is
      phosphorylated

<400> SEQUENCE: 142

Ala Tyr Ser Gln Glu Glu Ile Thr Gln Gly Phe Glu Glu Thr Gly Asp
1               5                   10                  15

Thr Leu Tyr Ala Pro Tyr Ser Thr His Phe Gln Leu Gln Asn Gln Pro
            20                  25                  30

Pro Gln Lys
        35

<210> SEQ ID NO 143
<211> LENGTH: 35
<212> TYPE: PRT
<213> ORGANISM: Homo sapiens
<220> FEATURE:
<221> NAME/KEY: MOD_RES
<222> LOCATION: (22)..(22)
<223> OTHER INFORMATION: PHOSPHORYLATION; tyrosine at position 22 is
      phosphorylated

<400> SEQUENCE: 143

Ala Tyr Ser Gln Glu Glu Ile Thr Gln Gly Phe Glu Glu Thr Gly Asp
1               5                   10                  15

Thr Leu Tyr Ala Pro Tyr Ser Thr His Phe Gln Leu Gln Asn Gln Pro
            20                  25                  30

Pro Gln Lys
        35

<210> SEQ ID NO 144
<211> LENGTH: 21
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: PHOSPHORYLATION; tyrosine at position 3 is
      phosphorylated

<400> SEQUENCE: 144

Ser Gln Tyr Leu Ser Ala Glu Glu Asn Tyr Glu Ser Cys Pro Pro Ser
1               5                   10                  15

Pro Tyr Thr Glu Arg
            20

<210> SEQ ID NO 145
<211> LENGTH: 19
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: PHOSPHORYLATION; tyrosine at position 12 is
      phosphorylated

<400> SEQUENCE: 145

Val Cys Ala Tyr Gly Ala Gln Gly Glu Gly Pro Tyr Ser Ser Leu Val
1               5                   10                  15
```

Ser Cys Arg

<210> SEQ ID NO 146
<211> LENGTH: 12
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: PHOSPHORYLATION; tyrosine at position 6 is
      phosphorylated

<400> SEQUENCE: 146

Met Gln Asn His Gly Tyr Glu Asn Pro Thr Tyr Lys
1               5                   10

<210> SEQ ID NO 147
<211> LENGTH: 12
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: PHOSPHORYLATION; tyrosine at position 11 is
      phosphorylated

<400> SEQUENCE: 147

Met Gln Gln Asn Gly Tyr Glu Asn Pro Thr Tyr Lys
1               5                   10

<210> SEQ ID NO 148
<211> LENGTH: 25
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: PHOSPHORYLATION; tyrosine at position 11 is
      phosphorylated

<400> SEQUENCE: 148

Asn Met Gly Gly Pro Tyr Gly Gly Asn Tyr Gly Pro Gly Gly Ser
1               5                   10                  15

Gly Gly Ser Gly Gly Tyr Gly Gly Arg
            20                  25

<210> SEQ ID NO 149
<211> LENGTH: 13
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: PHOSPHORYLATION; tyrosine at position 4 is
      phosphorylated

<400> SEQUENCE: 149

Asp Asp Gly Tyr Ser Thr Lys Asp Ser Tyr Ser Ser Arg
1               5                   10

<210> SEQ ID NO 150
<211> LENGTH: 36
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: PHOSPHORYLATION; tyrosine at position 9 is phosphorylated

<400> SEQUENCE: 150

Ala Gly Leu Gln Thr Ala Asp Lys Tyr Ala Ala Leu Ala Asn Leu Asp
1               5                   10                  15

Asn Ile Phe Ser Ala Gly Gln Gly Gly Asp Gln Gly Ser Gly Phe Gly
                20                  25                  30

Thr Thr Gly Lys
        35

<210> SEQ ID NO 151
<211> LENGTH: 15
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: PHOSPHORYLATION; tyrosine at position 10 is
      phosphorylated

<400> SEQUENCE: 151

Ser Ser Ser Ala Gly Gly Gln Gly Ser Tyr Val Pro Leu Leu Arg
1               5                   10                  15

<210> SEQ ID NO 152
<211> LENGTH: 10
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: PHOSPHORYLATION; tyrosine at position 6 is
      phosphorylated

<400> SEQUENCE: 152

Ser Arg Asp Pro His Tyr Asp Asp Phe Arg
1               5                   10

<210> SEQ ID NO 153
<211> LENGTH: 17
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 153

Leu Leu Gly Pro Gly Val Asn Tyr Ser Gly Cys Gln Ile Thr Trp Ala
1               5                   10                  15

Lys

<210> SEQ ID NO 154
<211> LENGTH: 14
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: PHOSPHORYLATION; tyrosine at position 4 is
      phosphorylated

<400> SEQUENCE: 154

Asn Ser Asn Tyr Phe Ser Met Asp Ser Met Glu Gly Lys Arg
1               5                   10

```
<210> SEQ ID NO 155
<211> LENGTH: 25
<212> TYPE: PRT
<213> ORGANISM: Homo sapiens
<220> FEATURE:
<221> NAME/KEY: MOD_RES
<222> LOCATION: (18)..(18)
<223> OTHER INFORMATION: PHOSPHORYLATION; tyrosine at position 18 is
      phosphorylated

<400> SEQUENCE: 155

Gln Lys Ser Asn Leu Phe Gln His Gln Lys Met His Thr Lys Glu Lys
1               5                   10                  15

Pro Tyr Gln Cys Lys Thr Cys Gly Lys
            20                  25

<210> SEQ ID NO 156
<211> LENGTH: 12
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: PHOSPHORYLATION; tyrosine at position 3 is
      phosphorylated

<400> SEQUENCE: 156

Gln Ala Tyr Glu Pro Pro Pro Pro Pro Ala Tyr Arg
1               5                   10

<210> SEQ ID NO 157
<211> LENGTH: 24
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: PHOSPHORYLATION; tyrosine at position 10 is
      phosphorylated

<400> SEQUENCE: 157

Glu Ala Gly Ile Asp His Leu Val Ser Tyr Pro Thr Ile Pro Pro Gly
1               5                   10                  15

Ile Thr Val Tyr Asn Arg Thr Lys
            20

<210> SEQ ID NO 158
<211> LENGTH: 24
<212> TYPE: PRT
<213> ORGANISM: Homo sapiens
<220> FEATURE:
<221> NAME/KEY: MOD_RES
<222> LOCATION: (15)..(15)
<223> OTHER INFORMATION: PHOSPHORYLATION; tyrosine at position 15 is
      phosphorylated

<400> SEQUENCE: 158

Tyr His Glu Met Val Gly Val Ile Phe Ser Asp Thr Phe Ser Tyr Arg
1               5                   10                  15

Leu Lys Phe Asn Trp Gly Tyr Arg
            20

<210> SEQ ID NO 159
<211> LENGTH: 24
<212> TYPE: PRT
<213> ORGANISM: Homo sapiens
<220> FEATURE:
```

```
<221> NAME/KEY: MOD_RES
<222> LOCATION: (23)..(23)
<223> OTHER INFORMATION: PHOSPHORYLATION; tyrosine at position 23 is
      phosphorylated

<400> SEQUENCE: 159

Tyr His Glu Met Val Gly Val Ile Phe Ser Asp Thr Phe Ser Tyr Arg
1               5                   10                  15

Leu Lys Phe Asn Trp Gly Tyr Arg
            20

<210> SEQ ID NO 160
<211> LENGTH: 19
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: PHOSPHORYLATION; tyrosine at position 5 is
      phosphorylated

<400> SEQUENCE: 160

Glu Leu Glu Arg Tyr Gln Lys His Leu Glu Asn Ala Lys Glu Ile Gly
1               5                   10                  15

Ile Lys Lys

<210> SEQ ID NO 161
<211> LENGTH: 18
<212> TYPE: PRT
<213> ORGANISM: Homo sapiens
<220> FEATURE:
<221> NAME/KEY: MOD_RES
<222> LOCATION: (17)..(17)
<223> OTHER INFORMATION: PHOSPHORYLATION; tyrosine at position 17 is
      phosphorylated

<400> SEQUENCE: 161

Ile His Ile Asp Arg Gly Pro Glu Glu Lys Pro Ala Gln Glu Ser Asn
1               5                   10                  15

Tyr Arg

<210> SEQ ID NO 162
<211> LENGTH: 26
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: PHOSPHORYLATION; tyrosine at position 3 is
      phosphorylated

<400> SEQUENCE: 162

Asn Ile Tyr Ser Asp Ile Pro Pro Gln Val Pro Val Arg Pro Ile Ser
1               5                   10                  15

Tyr Thr Pro Ser Ile Pro Ser Asp Ser Arg
            20                  25

<210> SEQ ID NO 163
<211> LENGTH: 21
<212> TYPE: PRT
<213> ORGANISM: Homo sapiens
<220> FEATURE:
<221> NAME/KEY: MOD_RES
<222> LOCATION: (16)..(16)
<223> OTHER INFORMATION: PHOSPHORYLATION; tyrosine at position 16 is
      phosphorylated
```

```
<400> SEQUENCE: 163

Asn Ser Gln Glu Ala Glu Val Ser Cys Pro Phe Ile Asp Asn Thr Tyr
1               5                   10                  15

Ser Cys Ser Gly Lys
            20

<210> SEQ ID NO 164
<211> LENGTH: 18
<212> TYPE: PRT
<213> ORGANISM: Homo sapiens
<220> FEATURE:
<221> NAME/KEY: MOD_RES
<222> LOCATION: (16)..(16)
<223> OTHER INFORMATION: PHOSPHORYLATION; tyrosine at position 16 is
      phosphorylated

<400> SEQUENCE: 164

Gly Ser Ser Gln Pro Asn Leu Ser Thr Ser His Ser Glu Gln Glu Tyr
1               5                   10                  15

Gly Lys

<210> SEQ ID NO 165
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 165

Ala Gly Gly Ser Pro Ala Ser Tyr His Gly Ser Thr Ser Pro Arg
1               5                   10                  15

<210> SEQ ID NO 166
<211> LENGTH: 26
<212> TYPE: PRT
<213> ORGANISM: Homo sapiens
<220> FEATURE:
<221> NAME/KEY: MOD_RES
<222> LOCATION: (21)..(21)
<223> OTHER INFORMATION: PHOSPHORYLATION; tyrosine at position 21 is
      phosphorylated

<400> SEQUENCE: 166

Met Pro Asn Val Pro Asn Thr Gln Pro Ala Ile Met Lys Pro Thr Glu
1               5                   10                  15

Glu His Pro Ala Tyr Thr Gln Ile Ala Lys
            20                  25

<210> SEQ ID NO 167
<211> LENGTH: 20
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: PHOSPHORYLATION; tyrosine at position 2 is
      phosphorylated

<400> SEQUENCE: 167

Asn Tyr Gly Ser Tyr Ser Thr Gln Ala Ser Ala Ala Ala Thr Ala
1               5                   10                  15

Glu Leu Leu Lys
            20
```

```
<210> SEQ ID NO 168
<211> LENGTH: 19
<212> TYPE: PRT
<213> ORGANISM: Homo sapiens
<220> FEATURE:
<221> NAME/KEY: MOD_RES
<222> LOCATION: (13)..(13)
<223> OTHER INFORMATION: PHOSPHORYLATION; tyrosine at position 13 is
      phosphorylated

<400> SEQUENCE: 168

Ala Ile Glu Pro Gln Lys Glu Glu Ala Asp Glu Asn Tyr Asn Ser Val
1               5                   10                  15

Asn Thr Arg
```